(12) United States Patent
Mazitschek et al.

(10) Patent No.: US 8,980,926 B2
(45) Date of Patent: Mar. 17, 2015

(54) 2-AMINOINDOLE COMPOUNDS AND METHODS FOR THE TREATMENT OF MALARIA

(75) Inventors: Ralph Mazitschek, Arlington, MA (US); Jon C. Clardy, Jamaica Plain, MA (US); Dyann Wirth, Boston, MA (US); Roger Wiegand, Wayland, MA (US); Sameer Urgaonkar, Arlington, NC (US); Mary Lynn Baniecki, Raleigh, NC (US); Joseph Cortese, Quincy, MA (US); Cassandra Celatka, Hull, MA (US); Yibin Xiang, Acton, MA (US); Renato Skerlj, Newton, MA (US); Elyse M. J. Bourque, Watertown, MA (US)

(73) Assignees: Genzyme Corporation, Cambridge, MA (US); President and Fellows of Harvard College, Cambridge, MA (US); Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 13/504,635

(22) PCT Filed: Oct. 28, 2010

(86) PCT No.: PCT/US2010/054473
§ 371 (c)(1),
(2), (4) Date: Apr. 27, 2012

(87) PCT Pub. No.: WO2011/053697
PCT Pub. Date: May 5, 2011

(65) Prior Publication Data
US 2012/0232063 A1    Sep. 13, 2012

Related U.S. Application Data

(60) Provisional application No. 61/256,879, filed on Oct. 30, 2009.

(51) Int. Cl.
| | | |
|---|---|---|
| A61K 31/404 | (2006.01) |
| A61K 31/4439 | (2006.01) |
| C07D 209/40 | (2006.01) |
| C07D 213/69 | (2006.01) |
| A61K 31/40 | (2006.01) |
| C07D 401/04 | (2006.01) |
| C07D 403/10 | (2006.01) |
| C07D 401/10 | (2006.01) |
| C07D 403/04 | (2006.01) |
| C07D 403/06 | (2006.01) |
| C07D 405/04 | (2006.01) |
| C07D 405/06 | (2006.01) |
| C07D 405/12 | (2006.01) |
| C07D 409/04 | (2006.01) |
| C07D 409/06 | (2006.01) |
| C07D 417/04 | (2006.01) |
| C07D 471/04 | (2006.01) |
| C07D 491/056 | (2006.01) |

(52) U.S. Cl.
CPC .............. *A61K 31/40* (2013.01); *C07D 213/69* (2013.01); *A61K 31/4439* (2013.01); *C07D 209/40* (2013.01); *C07D 401/04* (2013.01); *C07D 403/10* (2013.01); *C07D 401/10* (2013.01); *C07D 403/04* (2013.01); *C07D 403/06* (2013.01); *C07D 405/04* (2013.01); *C07D 405/06* (2013.01); *C07D 405/12* (2013.01); *C07D 409/04* (2013.01); *C07D 409/06* (2013.01); *C07D 417/04* (2013.01); *C07D 471/04* (2013.01); *C07D 491/056* (2013.01)
USPC .......................................... 514/339; 514/418

(58) Field of Classification Search
None
See application file for complete search history.

(56) References Cited

U.S. PATENT DOCUMENTS 3,576,001 A * 4/1971 Bell et al. ....................... 548/483
3,577,435 A    5/1971 Bell et al.
3,586,693 A    6/1971 Bell et al.
(Continued)

FOREIGN PATENT DOCUMENTS

FR    2 921 061 A1    3/2009
JP    55-79366    6/1980
(Continued)

OTHER PUBLICATIONS

Witulski, et al., "Palladium-Catalyzed Synthesis of 2-Aminoindoles by a Heteroannulation Reaction," *Angewandte Chemie International Edition*, 42(35): 4257-4260 (2003). Abstract only.
(Continued)

*Primary Examiner* — Alicia L Otton
(74) *Attorney, Agent, or Firm* — Hamilton, Brook, Smith & Reynolds, P.C.

(57) ABSTRACT

The present invention relates to methods of treating a subject with malaria comprising administering a 2-aminoindole compound represented by Formula: (I)—The values and preferred values of the variables in Structural Formula I are defined herein.

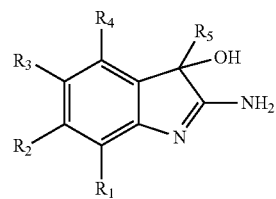

12 Claims, 3 Drawing Sheets

(56) References Cited

U.S. PATENT DOCUMENTS

| | | | |
|---|---|---|---|
| 3,686,210 | A | 8/1972 | Bell et al. |
| 3,714,188 | A | 1/1973 | Bell et al. |
| 3,801,593 | A | 4/1974 | Bell et al. |
| 3,931,226 | A | 1/1976 | White et al. |
| 6,605,634 | B2 | 8/2003 | Zablocki et al. |
| 8,431,538 | B2 | 4/2013 | Kozikowski et al. |
| 2005/0101654 | A1 | 5/2005 | Welberth et al. |

FOREIGN PATENT DOCUMENTS

| | | |
|---|---|---|
| JP | 55-133346 | 10/1980 |
| JP | 57-002271 | 1/1982 |
| JP | 58-015990 | 1/1983 |

OTHER PUBLICATIONS

Notification of Transmittal of the International Search Report and the Written Opinion of the International Searching Authority, or The Declaration for PCT/US2010/054473, titled "2-Aminoindole Compounds and Methods for the Treatment of Malaria"; Date of Mailing: Jan. 27, 2011 (10 pgs.).

International Preliminary Report on Patentability from counterpart International Application No. PCT/US2010/054473, "2-Aminoindole Compounds and Methods for the Treatment of Malaria", Dated: May 10, 2012.

Supplementary Search Report and Opinion in European International Application No. 10827467.1, Title: "2-Aminoindole Compounds and Methods for the Treatment of Malaria", dated: Mar. 26, 2013.

Database Caplus [Online] Chemcial Abstracts Service, Columbus, OH; Asahi Chemical Industry: "2-aminoindolenine derivatives", XP002693790, retrieved from STN, Database accession No. 1982:455687; & JP 57 002271 A (Asahi Chemical Industry Co., Ltd., Japan) (Jan. 7, 1982).

Ishizumi, K., et al., Quinazolines. II: Oxidation of 2-Aminoindoles and Related Compounds:, *Journal of Organic Chemistry*, vol. 39(17):2581-2587 (1974).

Benincori, T. and Sannicolo, F., "New Access to 2-(Arylazo)-, 2-(Arythydrazo)-, and 2-Aminoindoles, -benzofurans, and -thianaphtenes", *Journal of Organic Chemistry*, vol. 53(6):1309-1312 (1988).

Urgaonkar, S., et al., "A Concise Silylamine Approach to 2-Amino-3-hydroxy-indoles with Potent in vivo Antimalaria Activity", *Organic Letters*, vol. 12(18):3998-4001 (2010).

Plouffe, D., et al., "In silico activity profiling reveals the mechanism of action of antimalarials discovered in a high-throughput screen," *Proc., Natl. Acad. Sci. USA*, 105:9059-64 (2008).

Kocken, C.H., et al., "*Plasmodium knowlesi* Provides a Rapid In Vitro and In Vivo Transfection System That Enables Double-Crossover Gene Knockout Studies" *Infect. Immun.*, 70(2):655-660 (2002).

Sakiyama, F., et al., "Chemical Interconversion of Tryptophan and N'-Formylkynurenine," *Chemistry Letters*, pp. 1109-1112 (1979).

Sakiyama, F., et al., "Conversion of 3-Alkylindole to 3-Alkyl-2-Amino-3H-Indo1-3-Ol via Alkyl 2-Formamidophenyl Ketone," *Chemistry Letters*, pp. 587-590 (1979).

Waterhouse, I., et al., "Synthesis of Carbon-14 Labelled Indolic $5HT_1$ Receptor Agonists," *J. of Labelled Components and Radiopharmaceuticlas*, XXXVIII(11):1021-1030 (1996).

Belley, M., et al., "Synthesis and Reactivity of N-Hydroxy-2-Amino-3-Arylindoles," *Synlett*, 19:2991-2994 (2007).

Baniecki, M.L., et al., "High-Throughput *Plasmodium falciparum* Growth Assay for Malaria Drug Discovery," *Antimicrobial Agents and Chemotherapy*, 51(2):716-723 (2007).

Nakazawa, T., et al., "Chemical Conversion of kynurenine to tryptophan", *Peptide Chemistry*, vol. 16, pp. 11-16 (1979).

Golubeva, G.A., et al., "Indole chemistry. XXXV. Synthesis of 2-amino-3-alkylindoles", *Chemistry of Heterocyclic Compounds*, Issue 4, pp. 511-516 (1973).

Bell, S., et al., "Ring closure reactions with nitriles. III. Formation of 2-amino- and 2-oxo-3-hydroxyindoles from the reaction of 2'-aroylacylanilides with cyanide", *Journal of Heterocyclic Chemistry*, 6(5):599-604 (1969).

Wittig, G., et al, "o-Benzidine rearrangement of 3-methyl-4-phenylhydrazo-5-phenylisoxazole", *Justus Liebigs Annalen der chemie*, vol. 469, pp. 1-16 (1929).

\* cited by examiner

*P. berghei*, 4 days
QD dosing

US 8,980,926 B2

2-AMINOINDOLE COMPOUNDS AND METHODS FOR THE TREATMENT OF MALARIA

RELATED APPLICATION

This application is the U.S. National Stage of International Application No. PCT/US2010/054473, filed Oct. 28, 2010, which designates the U.S., published in English, and claims the benefit of U.S. Provisional Application No. 61/256,879, filed Oct. 30, 2009. The entire teachings of the above applications are incorporated herein by reference.

GOVERNMENT SUPPORT

This invention was made with government support under Grant Nos. CA078048 and NS053660 and NS50767 awarded by the National Institutes of Health. The Government has certain rights in the invention.

BACKGROUND OF THE INVENTION

Malaria is a vector-borne infectious disease caused by protozoan parasites and is widespread in tropical and subtropical regions, including parts of the Americas, Asia and Africa. Of the five *Plasmodium* parasite species that can infect humans (*P. falciparum, P. vivax, P. ovale, P. malariae* and *P. knowlesi*), the most serious forms of the disease are caused by *P. falciparum* and *P. vivax*. Of the approximately 515 million people infected yearly, between one and three million people, the majority of whom are young children in Sub-Saharan Africa, die from the disease. The current armament of approved anti-malarial drugs, such as chloroquine, atovaquone, pyrimethamine, and sulfadoxine, is limited to only a few targets within the human malaria parasite, and growing widespread resistance to current drugs is prompting the development of new antimalarial agents that have new biological targets.

SUMMARY OF THE INVENTION

It has now been found that a novel class of compounds based on a 2-aminoindole scaffold (referred to herein as "2-aminoindoles") has efficacy in the treatment of malaria. Representative compounds disclosed herein exhibit potent anti-malaria activity in vitro and in vivo and likely act via a mechanism that has not been utilized in malaria drug development. Some representatives of the class have been shown to cure malaria in a rodent model.

Accordingly, in one embodiment, the present invention relates to methods of treating a subject with malaria, comprising administering to the subject in need thereof an effective amount of a 2-aminoindole compound of the invention.

In another embodiment, the invention relates to 2-aminoindole compounds described herein.

In a further embodiment, the invention relates to compositions (e.g., pharmaceutical compositions) comprising a 2-aminoindole compound described herein.

In an additional embodiment, the invention relates to methods of preparing 2-aminoindole compounds described herein.

BRIEF DESCRIPTION OF THE DRAWINGS

FIG. 3D: At day 5, 0% of the Control group were without parasites while 100/mg/kg/day treatment with Compound 142 resulted in 20% without parasites and 200/mg/kg/day treatment with Compound 142 resulted in 80% without parasites. At day 30, 60% of the group treated with 200/mg/kg/day Compound 142 were without parasites.

DETAILED DESCRIPTION OF THE INVENTION

Figure 1:
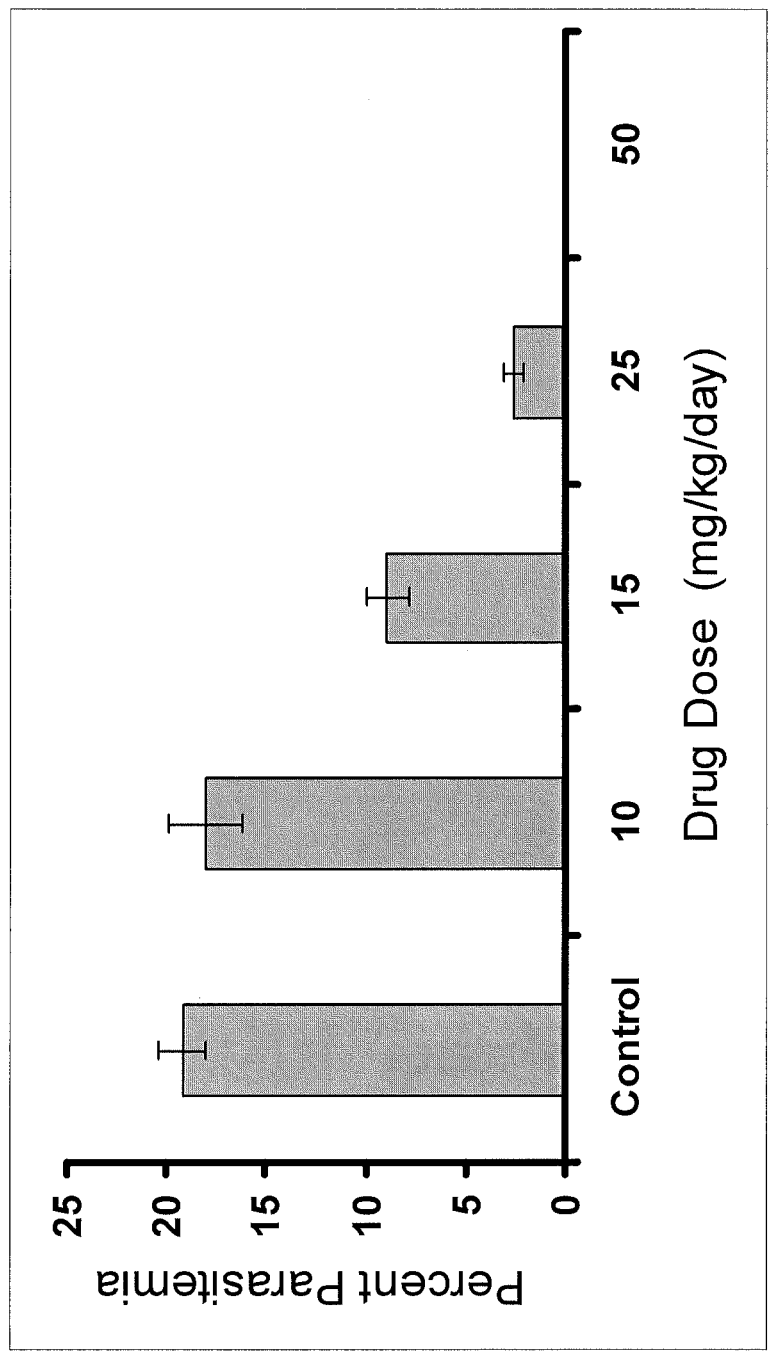
FIG. 1 is a graph depicting the in vivo efficacy of Compound 1 following IP administration for four days at various doses in an animal (rodent) model of malaria. A dose-response relationship was observed. A 50 mg/kg dose effectively treated malaria in the animal model.
Figure 2B:
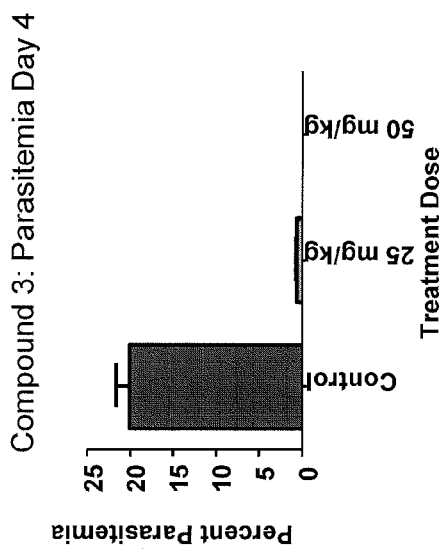
FIGS. 2A and 2B are graphs depicting the in vivo efficacy of the enantiomers of Compound 1 (i.e., Compounds 2 and 3). While both Compounds were efficacious for reducing parasitemia at a 50 mg/kg dose, a 50 mg/kg dose of Compound 3 effectively treated malaria in the animal model.
Figure 2A:
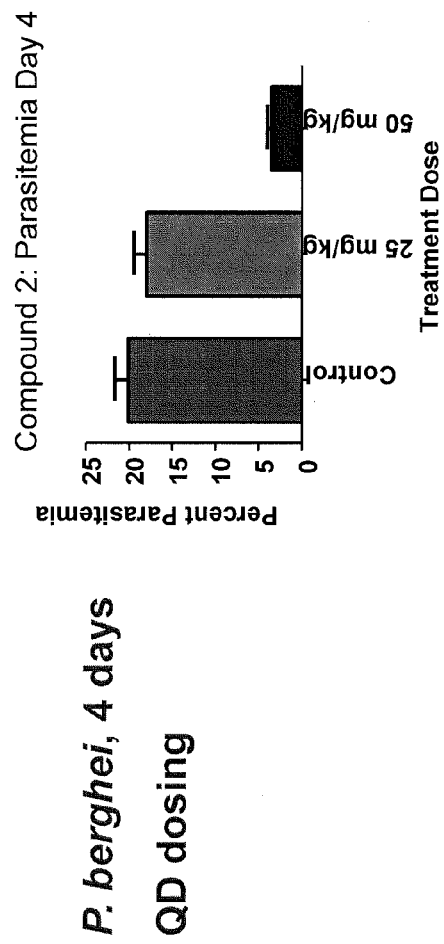
Figure 3A:
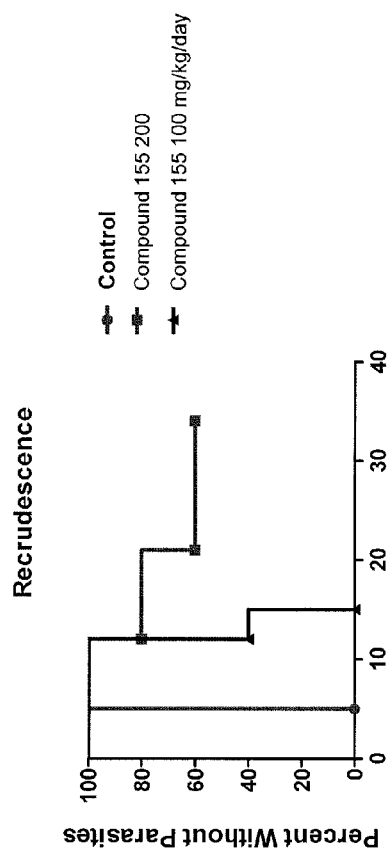
FIGS. 3A-D are graphs showing in vivo efficacy data (parasitemia and recrudescence) in a mouse malaria model for Compounds 155 (FIGS. 3A and 3B) and 142 (FIGS. 3C and 3D).
Figure 3B:
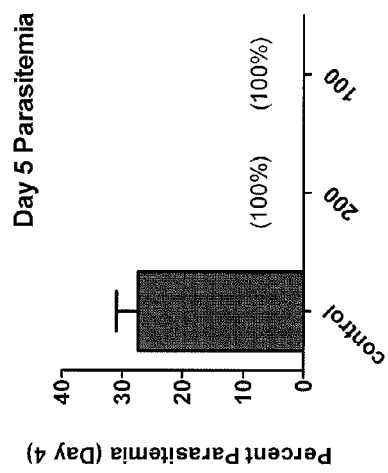
Figure 3C:
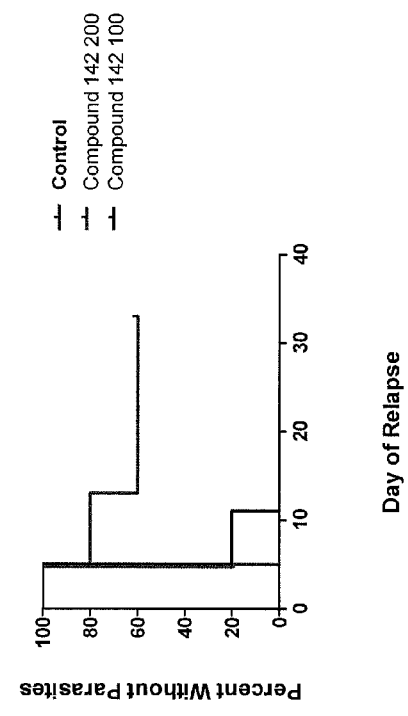
Figure 3D:
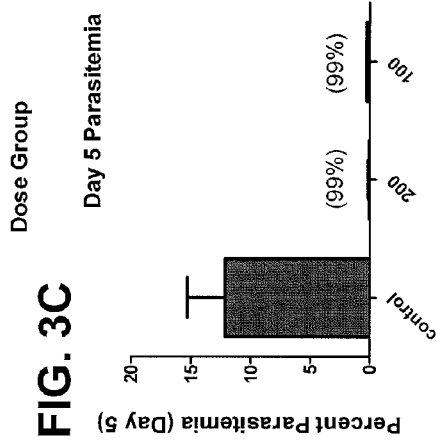

In a first embodiment, the present invention is a method of treating a subject with malaria, comprising administering to the subject in need thereof an effective amount of a compound of Formula I:

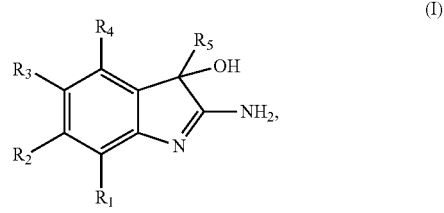

or a pharmaceutically acceptable salt thereof,
wherein
$R_1$, $R_2$, $R_3$ and $R_4$ are independently hydrogen, halogen (e.g., fluorine, chlorine, bromine, iodine), nitro, cyano, hydroxy, $(C_1-C_6)$alkyl, $(C_1-C_6)$alkenyl, $(C_1-C_6)$alkynyl, $(C_1-C_6)$alkoxy, aryl, heteroaryl, cycloalkyl, heterocyclyl, aryl$(C_1-C_3)$alkyl, heteroaryl$(C_1-C_3)$alkyl, cycloalkyl$(C_1-C_3)$alkyl, heterocyclyl$(C_1-C_3)$alkyl, hydroxy$(C_1-C_3)$alkyl, $N(R_7)_2$, $C(=NOH)NH_2$, $NR_7CON(R_7)_2$, $CON(R_7)_2$, $CO_2R_7$, $COR_8$, $OC(O)R_7$, $SO_2N(R_7)_2$, $SO_2R_8$, $NR_7COR_8$, $NR_7CO_2R_8$, $NR_7SO_2R_8$ and $OC(=O)N(R_7)_2$, each optionally substituted with one or more groups represented by $R_6$;
wherein $R_2$ and $R_3$, along with the carbons to which they are attached, can form a heterocyclyl or heteroaryl, wherein the heterocyclyl or heteroaryl formed is optionally substituted by one or more groups represented by $R_6$;
$R_5$ is aryl, heteroaryl, cycloalkyl, heterocyclyl, aryl$(C_1-C_3)$alkyl, aryl$(C_3-C_{10})$heterocyclyl, aryl$(C_1-C_3)$alkoxy, heteroaryl$(C_1-C_3)$alkyl, cycloalkyl$(C_1-C_3)$alkyl, heterocyclyl$(C_1-C_3)$alkyl, alkylheteroaryl, $(C_1-C_6)$alkyl, $(C_1-C_4)$alkoxy, each optionally substituted with one to three groups represented by $R_6$;
Each $R_6$ is independently selected from halogen (e.g., fluorine, chlorine, bromine, iodine), nitro, cyano, hydroxy, $(C_1-C_4)$alkyl, halo$(C_1-C_3)$alkyl, hydroxy$(C_1-C_4)$alkyl, $(C_1-C_4)$alkoxy, halo$(C_1-C_4)$alkoxy, aryl, haloaryl, cycloalkyl, aryl$(C_1-C_3)$alkyl, aryl$(C_1-C_4)$alkoxy, heterocyclyl, $N(R_7)_2$, $C(=NOH)NH_2$, $NR_7CON(R_7)_2$, $CON(R_7)_2$, $CO_2R_7$, $COR_8$, $OC(O)R_8$, $S$, $SO_2N(R_8)_2$, $SO_2R_8$, $SR_8$, $S(C_1-C_3)$alkylcycloalkyl, $NR_7COR_8$, $NR_7CO_2R_8$, $NR_8SO_2R_8$, $S(=O)R_8$, —O-cycloalkyl, —O-heterocyclyl, adamantyl, $OC(=O)N(R_7)_2$,

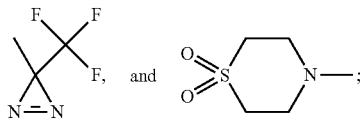

Each $R_7$ is independently selected from hydrogen, $(C_1-C_{10})$alkyl, aryl, or aryl$(C_1-C_3)$alkyl, each optionally substituted with halogen (e.g., fluorine, chlorine, bromine, iodine), $(C_1-C_3)$alkoxy, $(C_1-C_3)$alkyl, halo$(C_1-C_3)$alkyl, halo$(C_1-C_3)$alkoxy, cyano or nitro; and Each $R_8$ is independently selected from hydrogen, halogen (e.g., fluorine, chlorine, bromine, iodine), $(C_1-C_{10})$alkyl, $(C_1-C_{10})$alkoxy, aryl, aryl$(C_1-C_3)$alkyl, cycloalkyl or aryl$(C_1-C_3)$alkoxy, each optionally substituted with halogen (e.g., fluorine, chlorine, bromine, iodine), $(C_1-C_3)$alkoxy, $(C_1-C_3)$alkyl, halo$(C_1-C_3)$alkyl, halo$(C_1-C_3)$alkoxy, cyano or nitro.

In a second embodiment, the present invention is a compound of Formula IIa:

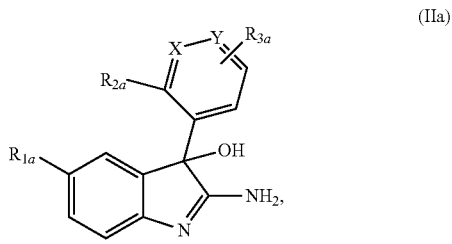

(IIa)

or a pharmaceutically acceptable salt thereof,
wherein
X is carbon or nitrogen;
Y is carbon or nitrogen;
$R_{1a}$ is hydrogen, halogen (e.g., fluorine, chlorine, bromine, iodine), nitro, cyano, hydroxy, $(C_1-C_6)$alkyl, $(C_1-C_6)$alkenyl, $(C_1-C_6)$alkynyl, $(C_1-C_6)$alkoxy, aryl, heteroaryl, cycloalkyl, heterocyclyl, aryl$(C_1-C_3)$alkyl, heteroaryl$(C_1-C_3)$alkyl, cycloalkyl$(C_1-C_3)$alkyl, heterocyclyl$(C_1-C_3)$alkyl, hydroxy$(C_1-C_3)$alkyl, $N(R_{5a})_2$, $C(=NOH)NH_2$, $NR_{5a}CON(R_{5a})_2$, $CON(R_{5a})_2$, $CO_2R_{5a}$, $COR_{6a}$, $OC(O)R_{5a}$, $SO_2N(R_{5a})_2$, $SO_2R_{6a}$, $NR_{5a}COR_{6a}$, $NR_{5a}CO_2R_{6a}$, $NR_{5a}SO_2R_{6a}$ and $OC(=O)N(R_{5a})_2$, each optionally substituted with one or more groups represented by $R_{4a}$;

$R_{2a}$ is $(C_1-C_6)$alkyl, $(C_1-C_6)$alkoxy, $S(C_1-C_6)$alkyl, $SO(C_1-C_6)$alkyl or $SO_2(C_1-C_6)$alkyl or optionally substituted with one or more groups represented by $R_{4a}$;

$R_{3a}$ is halogen (e.g., fluorine, chlorine, bromine, iodine), $(C_1-C_6)$alkyl or $(C_1-C_6)$alkoxy, each optionally substituted with one or more groups represented by $R_{4a}$;

Each $R_{4a}$ is independently selected from halogen (e.g., fluorine, chlorine, bromine, iodine), nitro, cyano, hydroxy, $(C_1-C_4)$alkyl, halo$(C_1-C_3)$alkyl, hydroxy$(C_1-C_4)$alkyl, $(C_1-C_4)$alkoxy, halo$(C_1-C_4)$alkoxy, aryl, haloaryl, cycloalkyl, aryl$(C_1-C_3)$alkyl, aryl$(C_1-C_4)$alkoxy, heterocyclyl, $N(R_{5a})_2$, $C(=NOH)NH_2$, $NR_{5a}CON(R_{5a})_2$, $CON(R_{5a})_2$, $CO_2R_{5a}$, $COR_{6a}$, $OC(O)R_{5a}$, S, $SO_2N(R_{5a})_2$, $SO_2R_{6a}$, $SR_{6a}$, $S(C_1-C_3)$alkylcycloalkyl, $NR_{5a}COR_{6a}$, $NR_5CO_2R_{6a}$, $NR_{5a}SO_2R_{6a}$, $S(=O)R_{6a}$, —O-cycloalkyl, —O-heterocyclyl, adamantyl, $OC(=O)N(R_{5a})_2$,

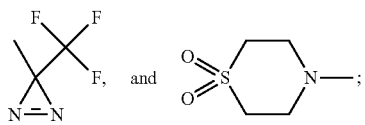

Each $R_{5a}$ is independently selected from hydrogen, $(C_1-C_{10})$alkyl, aryl or aryl$(C_1-C_6)$alkyl, each optionally substituted with halogen (e.g., fluorine, chlorine, bromine, iodine), $(C_1-C_3)$alkoxy, $(C_1-C_3)$alkyl, halo$(C_1-C_3)$alkyl, halo$(C_1-C_3)$alkoxy, cyano or nitro; and Each $R_{6a}$ is independently selected hydrogen, halogen (e.g., fluorine, chlorine, bromine, iodine), $(C_1-C_{10})$alkyl, $(C_1-C_{10})$alkoxy, aryl$(C_1-C_3)$alkyl, cycloalkyl or aryl$(C_1-C_3)$alkoxy, each optionally substituted with halogen (e.g., fluorine, chlorine, bromine, iodine), $(C_1-C_3)$alkoxy, $(C_1-C_3)$alkyl, halo$(C_1-C_3)$alkyl, halo$(C_1-C_3)$alkoxy, cyano or nitro.

In a third embodiment, the present invention is a pharmaceutical composition comprising the compound of Formula IIa, or a pharmaceutically acceptable salt thereof, and a pharmaceutically acceptable carrier.

In a fourth embodiment, the present invention is a compound of Formula VI:

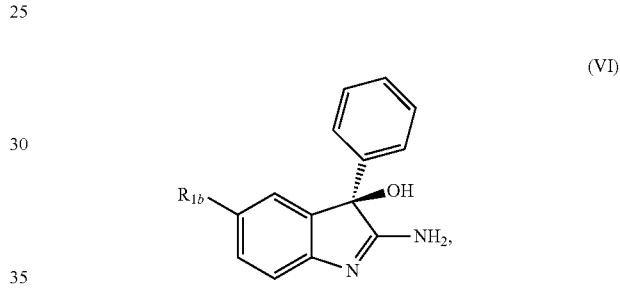

(VI)

or a pharmaceutically acceptable salt thereof,
wherein
$R_{1b}$ is hydrogen, halogen (e.g., fluorine, chlorine, bromine, iodine), nitro, cyano, hydroxy, $(C_1-C_6)$alkyl, $(C_1-C_6)$alkenyl, $(C_1-C_6)$alkynyl, $(C_1-C_6)$alkoxy, aryl, heteroaryl, cycloalkyl, heterocyclyl, aryl$(C_1-C_3)$alkyl, heteroaryl$(C_1-C_3)$alkyl, cycloalkyl$(C_1-C_3)$alkyl, heterocyclyl$(C_1-C_3)$alkyl, hydroxy$(C_1-C_3)$alkyl, $N(R_{3b})_2$, $C(=NOH)NH_2$, $NR_3CON(R_{3b})_2$, $CON(R_{3b})_2$, $CO_2R_{3b}$, $COR_{4b}$, $OC(O)R_{3b}$, $SO_2N(R_{3b})_2$, $SO_2R_{4b}$, $NR_3COR_{4b}$, $NR_{3a}CO_2R_{4b}$, $NR_{3b}SO_2R_{4b}$ and $OC(=O)N(R_{3b})_2$, each optionally substituted with one or more groups represented by $R_{2b}$;

Each $R_{2b}$ is independently selected from halogen (e.g., fluorine, chlorine, bromine, iodine), nitro, cyano, hydroxy, $(C_1-C_4)$alkyl, halo$(C_1-C_3)$alkyl, hydroxy$(C_1-C_4)$alkyl, $(C_1-C_4)$alkoxy, halo$(C_1-C_4)$alkoxy, aryl, haloaryl, cycloalkyl, aryl$(C_1-C_3)$alkyl, aryl$(C_1-C_4)$alkoxy, heterocyclyl, $N(R_{3b})_2$, $C(=NOH)NH_2$, $NR_{3b}CON(R_{3b})_2$, $CON(R_{3b})_2$, $CO_2R_{3b}$, $COR_{4b}$, $OC(O)R_{3b}$, S, $SO_2N(R_{3b})_2$, $SO_2R_{4b}$, $SR_{4b}$, $S(C_1-C_3)$alkylcycloalkyl, $NR_{3b}COR_{4b}$, $NR_{3b}CO_2R_{4b}$, $NR_{3b}SO_2R_{4b}$, $S(=O)R_{3b}$, —O-cycloalkyl, —O-heterocyclyl, adamantyl, $OC(=O)N(R_{3b})_2$,

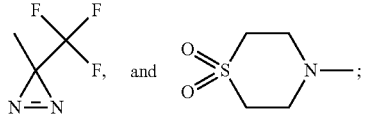

Each $R_{3b}$ is independently selected from hydrogen, $(C_1-C_{10})$alkyl, aryl or aryl$(C_1-C_3)$alkyl, each optionally substituted with halogen (e.g., fluorine, chlorine, bromine, iodine), $(C_1-C_3)$alkoxy, $(C_1-C_3)$alkyl, halo$(C_1-C_3)$alkyl, halo$(C_1-C_3)$alkoxy, cyano or nitro; and Each $R_{4b}$ is independently selected from hydrogen, halogen (e.g., fluorine, chlorine, bromine, iodine), $(C_1-C_{10})$alkyl, $(C_1-C_{10})$alkoxy, aryl, aryl$(C_1-C_3)$alkyl, cycloalkyl or aryl$(C_1-C_3)$alkoxy, each optionally substituted with halogen (e.g., fluorine, chlorine, bromine, iodine), $(C_1-C_3)$alkoxy, $(C_1-C_3)$alkyl, halo$(C_1-C_3)$alkyl, halo$(C_1-C_3)$alkoxy, cyano or nitro.

Values and alternative values for the variables in Structural Formula I are provided in the following paragraphs:

$R_1$ is hydrogen, halogen (e.g., fluorine, chlorine, bromine, iodine), nitro, cyano, hydroxy, $(C_1-C_6)$alkyl, $(C_1-C_6)$alkenyl, $(C_1-C_6)$alkynyl, $(C_1-C_6)$alkoxy, aryl, heteroaryl, cycloalkyl, heterocyclyl, aryl$(C_1-C_3)$alkyl, heteroaryl$(C_1-C_3)$alkyl, cycloalkyl$(C_1-C_3)$alkyl, heterocyclyl$(C_1-C_3)$alkyl, hydroxy$(C_1-C_3)$alkyl, $N(R_7)_2$, $C(=NOH)NH_2$, $NR_7CON(R_7)_2$, $CON(R_7)_2$, $CO_2R_7$, $COR_8$, $OC(O)R_7$, $SO_2N(R_7)_2$, $SO_2R_8$, $NR_7COR_8$, $NR_7CO_2R_8$, $NR_7SO_2R_8$ and $OC(=O)N(R_7)_2$, each optionally substituted with one or more groups represented by $R_6$. Alternatively, $R_1$ is hydrogen, halogen (e.g., fluorine, chlorine, bromine, iodine), $(C_1-C_4)$alkyl, or $(C_1-C_4)$alkoxy. Alternatively, $R_1$ is chlorine.

$R_2$ is hydrogen, halogen (e.g., fluorine, chlorine, bromine, iodine), nitro, cyano, hydroxy, $(C_1-C_6)$alkyl, $(C_1-C_6)$alkenyl, $(C_1-C_6)$alkynyl, $(C_1-C_6)$alkoxy, aryl, heteroaryl, cycloalkyl, heterocyclyl, aryl$(C_1-C_3)$alkyl, heteroaryl$(C_1-C_3)$alkyl, cycloalkyl$(C_1-C_3)$alkyl, heterocyclyl$(C_1-C_3)$alkyl, hydroxy$(C_1-C_3)$alkyl, $N(R_7)_2$, $C(=NOH)NH_2$, $NR_7CON(R_7)_2$, $CON(R_7)_2$, $CO_2R_7$, $COR_8$, $OC(O)R_7$, $SO_2N(R_7)_2$, $SO_2R_8$, $NR_7COR_8$, $NR_7CO_2R_8$, $NR_7SO_2R_8$ and $OC(=O)N(R_7)_2$, each optionally substituted with one or more groups represented by $R_6$. Alternatively, $R_2$ is hydrogen, halogen (e.g., fluorine, chlorine, bromine, iodine), $(C_1-C_4)$alkyl, or $(C_1-C_4)$alkoxy. Alternatively, $R_2$ is ethoxy. Alternatively, $R_2$ is methoxy. Alternatively $R_2$ is hydroxy.

$R_3$ is hydrogen, halogen (e.g., fluorine, chlorine, bromine, iodine), nitro, cyano, hydroxy, $(C_1-C_6)$alkyl, $(C_1-C_6)$alkenyl, $(C_1-C_6)$alkynyl, $(C_1-C_6)$alkoxy, aryl, heteroaryl, cycloalkyl, heterocyclyl, aryl$(C_1-C_3)$alkyl, heteroaryl$(C_1-C_3)$alkyl, cycloalkyl$(C_1-C_3)$alkyl, heterocyclyl$(C_1-C_3)$alkyl, hydroxy$(C_1-C_3)$alkyl, $N(R_7)_2$, $C(=NOH)NH_2$, $NR_7CON(R_7)_2$, $CON(R_7)_2$, $CO_2R_7$, $COR_8$, $OC(O)R_7$, $SO_2N(R_7)_2$, $SO_2R_8$, $NR_7COR_8$, $NR_7CO_2R_8$, $NR_7SO_2R_8$ and $OC(=O)N(R_7)_2$, each optionally substituted with one or more groups represented by $R_6$. Alternatively, $R_3$ is hydrogen, halogen (e.g., fluorine, chlorine, bromine, iodine), $(C_1-C_4)$alkyl, or $(C_1-C_4)$alkoxy. Alternatively, $R_3$ is chlorine. Alternatively, $R_3$ is fluorine. Alternatively, $R_3$ is methoxy.

Alternatively, $R_2$ and $R_3$, along with the carbons to which they are attached, form a heterocyclyl or heteroaryl, wherein the heterocyclyl or heteroaryl formed is optionally substituted by one or more groups represented by $R_6$.

$R_4$ is hydrogen, halogen (e.g., fluorine, chlorine, bromine, iodine), nitro, cyano, hydroxy, $(C_1-C_6)$alkyl, $(C_1-C_6)$alkenyl, $(C_1-C_6)$alkynyl, $(C_1-C_6)$alkoxy, aryl, heteroaryl, cycloalkyl, heterocyclyl, aryl$(C_1-C_3)$alkyl, heteroaryl$(C_1-C_3)$alkyl, cycloalkyl$(C_1-C_3)$alkyl, heterocyclyl$(C_1-C_3)$alkyl, hydroxy$(C_1-C_3)$alkyl, $N(R_7)_2$, $C(=NOH)NH_2$, $NR_7CON(R_7)_2$, $CON(R_7)_2$, $CO_2R_7$, $COR_8$, $OC(O)R_7$, $SO_2N(R_7)_2$, $SO_2R_8$, $NR_7COR_8$, $NR_7CO_2R_8$, $NR_7SO_2R_8$ and $OC(=O)N(R_7)_2$, each optionally substituted with one or more groups represented by $R_6$. Alternatively, $R_4$ is hydrogen, halogen (e.g., fluorine, chlorine, bromine, iodine), $(C_1-C_4)$alkyl, or $(C_1-C_4)$alkoxy.

$R_5$ is aryl, heteroaryl, cycloalkyl, heterocyclyl, aryl$(C_1-C_3)$alkyl, aryl$(C_3-C_{10})$heterocyclyl, aryl$(C_1-C_3)$alkoxy, heteroaryl$(C_1-C_3)$alkyl, cycloalkyl$(C_1-C_3)$alkyl, heterocyclyl$(C_1-C_3)$alkyl, alkylheteroaryl, $(C_1-C_6)$alkyl, $(C_1-C_4)$alkoxy, each optionally substituted with one to three groups represented by $R_6$.

Each $R_6$ is independently selected from halogen (e.g., fluorine, chlorine, bromine, iodine), nitro, cyano, hydroxy, $(C_1-C_4)$alkyl, halo$(C_1-C_3)$alkyl, hydroxy$(C_1-C_4)$alkyl, $(C_1-C_4)$alkoxy, halo$(C_1-C_4)$alkoxy, aryl, haloaryl, cycloalkyl, aryl$(C_1-C_3)$alkyl, aryl$(C_1-C_4)$alkoxy, heterocyclyl, $N(R_7)_2$, $C(=NOH)NH_2$, $NR_7CON(R_7)_2$, $CON(R_7)_2$, $CO_2R_7$, $COR_8$, $OC(O)R_8$, S, $SO_2N(R_8)_2$, $SO_2R_8$, $SR_8$, $S(C_1-C_3)$alkylcycloalkyl, $NR_7COR_8$, $NR_7CO_2R_8$, $NR_8SO_2R_8$, $S(=O)R_8$, —O-cycloalkyl, —O-heterocyclyl, adamantyl, $OC(=O)N(R_7)_2$,

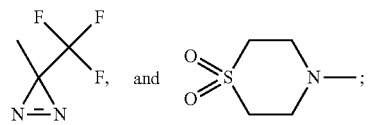

and

Each $R_7$ is independently selected from hydrogen, $(C_1-C_{10})$alkyl, aryl, or aryl$(C_1-C_3)$alkyl, each optionally substituted with halogen (e.g., fluorine, chlorine, bromine, iodine), $(C_1-C_3)$alkoxy, $(C_1-C_3)$alkyl, halo$(C_1-C_3)$alkyl, halo$(C_1-C_3)$alkoxy, cyano or nitro; and Each $R_8$ is independently selected from hydrogen, halogen (e.g., fluorine, chlorine, bromine, iodine), $(C_1-C_{10})$alkyl, $(C_1-C_{10})$alkoxy, aryl, aryl$(C_1-C_3)$alkyl, cycloalkyl or aryl$(C_1-C_3)$alkoxy, each optionally substituted with halogen (e.g., fluorine, chlorine, bromine, iodine), $(C_1-C_3)$alkoxy, $(C_1-C_3)$alkyl, halo$(C_1-C_3)$alkyl, halo$(C_1-C_3)$alkoxy, cyano or nitro.

In another embodiment, the present invention is a method of treating a subject with malaria, comprising administering to the subject in need thereof an effective amount of a compound of Formula II:

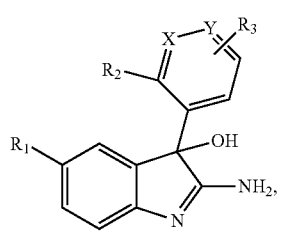

(II)

or a pharmaceutically acceptable salt thereof, wherein values and alternative values for $R_1$, $R_2$, and $R_3$ are as defined above for Structural Formula I, X is carbon or nitrogen and Y is carbon or nitrogen. Alternatively, X is carbon and Y is carbon. Alternatively, X is nitrogen and Y is carbon.

In another embodiment, the present invention is a method of treating a subject with malaria, comprising administering to the subject in need thereof an effective amount of a compound of Formula III:

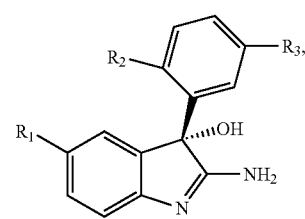

(III)

or a pharmaceutically acceptable salt thereof, wherein values and alternative values for $R_1$, $R_2$, and $R_3$ are as defined above for Structural Formula I.

In another embodiment, the present invention is a method of treating a subject with malaria, comprising administering to the subject in need thereof an effective amount of a compound of Formula (XXIII)

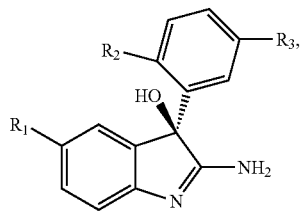

(XXIII)

or a pharmaceutically acceptable salt thereof, wherein values and alternative values for $R_1$, $R_2$, and $R_3$ are as defined above for Structural Formula I.

In another embodiment, the present invention is a method of treating a subject with malaria, comprising administering to the subject in need thereof an effective amount of a compound of Formula IV:

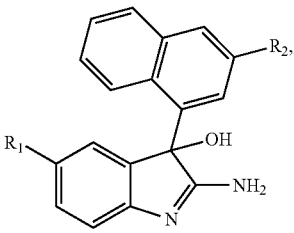

(IV)

or a pharmaceutically acceptable salt thereof, wherein values and alternative values for $R_1$ and $R_2$ are as defined above for Structural Formula I.

In another embodiment, the present invention is a method of treating a subject with malaria, comprising administering to the subject in need thereof an effective amount of a compound of Formula V:

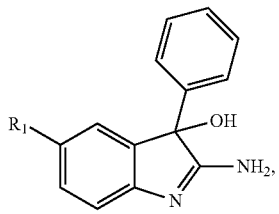

(V)

or a pharmaceutically acceptable salt thereof, wherein values and alternative values for $R_1$ are as defined above for Structural Formula I.

Values and alternative values for the variables in Structural Formula IIa are provided in the following paragraphs:

X is carbon or nitrogen. Alternatively, X is carbon.
Y is carbon or nitrogen. Alternatively, Y is carbon.
$R_{1a}$ is hydrogen, halogen (e.g., fluorine, chlorine, bromine, iodine), nitro, cyano, hydroxy, $(C_1-C_6)$alkyl, $(C_1-C_6)$alkenyl, $(C_1-C_6)$alkynyl, $(C_1-C_6)$alkoxy, aryl, heteroaryl, cycloalkyl, heterocyclyl, aryl$(C_1-C_3)$alkyl, heteroaryl$(C_1-C_3)$alkyl, cycloalkyl$(C_1-C_3)$alkyl, heterocyclyl$(C_1-C_3)$alkyl, hydroxy$(C_1-C_3)$alkyl, $N(R_{5a})_2$, $C(=NOH)NH_2$, $NR_{5a}CON(R_{5a})_2$, $CON(R_{5a})_2$, $CO_2R_{5a}$, $COR_{6a}$, $OC(O)R_{5a}$, $SO_2N(R_{5a})_2$, $SO_2R_{6a}$, $NR_{5a}COR_{6a}$, $NR_{5a}CO_2R_{6a}$, $NR_{5a}SO_2R_{6a}$ and $OC(=O)N(R_{5a})_2$, each optionally substituted with one or more groups represented by $R_{4a}$. Alternatively, $R_{1a}$ is halogen (e.g., fluorine, chlorine, bromine, iodine), $(C_1-C_4)$alkyl or $(C_1-C_4)$alkoxy. Alternatively, $R_{1a}$ is chlorine.

$R_{2a}$ is $(C_1-C_6)$alkyl, $(C_1-C_6)$alkoxy, $S(C_1-C_6)$alkyl, $SO(C_1-C_6)$alkyl, $SO_2(C_1-C_6)$alkyl, optionally substituted with one or more groups represented by $R_{4a}$. Alternatively, $R_{2a}$ is $(C_1-C_6)$alkoxy. Alternatively, $R_{2a}$ is ethoxy.

$R_{3a}$ is halogen (e.g., fluorine, chlorine, bromine, iodine), $(C_1-C_6)$alkyl or $(C_1-C_6)$alkoxy, each optionally substituted with one or more groups represented by $R_{4a}$. Alternatively $R_{3a}$ is halogen. Alternatively, $R_{3a}$ is fluorine.

Each $R_{4a}$ is independently selected from halogen (e.g., fluorine, chlorine, bromine, iodine), nitro, cyano, hydroxy, $(C_1-C_4)$alkyl, halo$(C_1-C_3)$alkyl, hydroxy$(C_1-C_4)$alkyl, $(C_1-C_4)$alkoxy, halo$(C_1-C_4)$alkoxy, aryl, haloaryl, cycloalkyl, aryl$(C_1-C_3)$alkyl, aryl$(C_1-C_4)$alkoxy, heterocyclyl, $N(R_{5a})_2$, $C(=NOH)NH_2$, $NR_{5a}CON(R_{5a})_2$, $CON(R_{5a})_2$, $CO_2R_{5a}$, $COR_{6a}$, $OC(O)R_{5a}$, S, $SO_2N(R_{5a})_2$, $SO_2R_{6a}$, $SR_{6a}$, $S(C_1-C_3)$alkylcycloalkyl, $NR_{5a}COR_{6a}$, $NR_5CO_2R_{6a}$, $NR_{5a}SO_2R_{6a}$, $S(=O)R_{6a}$, —O-cycloalkyl, —O-heterocyclyl, adamantyl, $OC(=O)N(R_{5a})_2$,

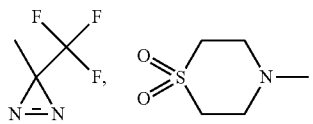

and $(C_1-C_3)$alkylC(=O)NH$(C_1-C_3)$alkyl-O—$(C_1-C_3)$alkyl-O—$(C_1-C_3)$alkylNHR$_{7a}$.

Each $R_{5a}$ is independently selected from hydrogen, $(C_1-C_{10})$alkyl, aryl or aryl$(C_1-C_6)$alkyl, each optionally substituted with halogen (e.g., fluorine, chlorine, bromine, iodine), $(C_1-C_3)$alkoxy, $(C_1-C_3)$alkyl, halo$(C_1-C_3)$alkyl, halo$(C_1-C_3)$alkoxy, cyano or nitro.

Each $R_{6a}$ is independently selected hydrogen, halogen (e.g., fluorine, chlorine, bromine, iodine), $(C_1-C_{10})$alkyl, $(C_1-C_{10})$alkoxy, aryl$(C_1-C_3)$alkyl, cycloalkyl or aryl$(C_1-C_3)$alkoxy, each optionally substituted with halogen (e.g., fluorine, chlorine, bromine, iodine), $(C_1-C_3)$alkoxy, $(C_1-C_3)$alkyl, halo$(C_1-C_3)$alkyl, halo$(C_1-C_3)$alkoxy, cyano or nitro.

In another embodiment, the present invention is a compound of Formula IIIa:

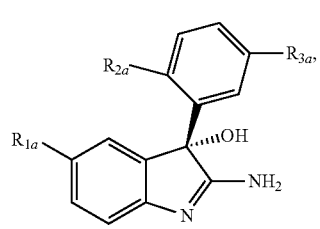

(IIIa)

or a pharmaceutically acceptable salt thereof, wherein values and alternative values for $R_{1a}$, $R_{2a}$ and $R_{3a}$ and are as defined above for Formula IIa.

In another embodiment, the present invention is a compound of Formula XXIIIa:

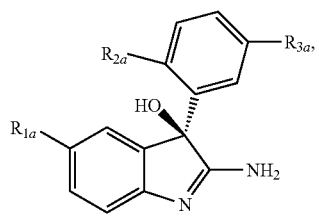

(XXIIIa)

or a pharmaceutically acceptable salt thereof, wherein values and alternative values for $R_{1a}$, $R_{2a}$ and $R_{3a}$ and are as defined above for Formula IIa.

In another embodiment, $R_1$, $R_2$, $R_3$ and $R_4$ are independently hydrogen, halogen (e.g., fluorine, chlorine, bromine, iodine), $(C_1-C_4)$alkyl, or $(C_1-C_4)$alkoxy and the remainder of variables are as defined above for Formula I.

In another embodiment, $R_3$ is chlorine and the remainder of variables are as defined above for Formula I.

In another embodiment, $R_1$ is chlorine, $R_2$ is ethoxy, $R_3$ is fluorine, X is carbon, Y is carbon and the remainder of variables are as defined above for Formula II.

In another embodiment, $R_1$ is chlorine, $R_2$ and $R_3$ are methoxy, X is nitrogen, Y is carbon and the remainder of variables are as defined above for Formula II.

In another embodiment, $R_1$ is chlorine, $R_2$ is hydroxyl, $R_3$ is fluorine and the remainder of variables are as defined above for Formula II.

In another embodiment, $R_1$ is chlorine, $R_2$ is hydroxyl, $R_3$ is fluorine, X is carbon, Y is carbon and the remainder of variables are as defined above for Formula II.

In another embodiment, $R_1$ is chlorine, $R_2$ ethoxy and $R_3$ is fluorine and the remainder of variables are as defined above for Formula III.

In another embodiment, $R_1$ is chlorine and the remainder of variables are as defined above for Formula V.

In another embodiment, $R_{1a}$ is halogen (e.g., fluorine, chlorine, bromine, iodine), $(C_1-C_4)$alkyl or $(C_1-C_4)$alkoxy and the remainder of variables are as defined above for Formula IIa.

In another embodiment, $R_{1a}$ $(C_1-C_4)$alkoxy and the remainder of variables are as defined above for Formula IIa.

In another embodiment, $R_{1a}$ is halogen and the remainder of variables are as defined above for Formula IIa.

In another embodiment, $R_{1a}$ is chlorine, $R_{2a}$ and $R_{3a}$ are methoxy, X is nitrogen, Y is carbon and the remainder of variables are as defined above for Formula IIa.

In another embodiment, $R_{1b}$ is halogen, (C1-C6)alkyl or (C1-C6)alkoxy and the remainder of variables are as defined above for Formula VI.

In another embodiment, $R_{1b}$ is halogen and the remainder of variables are as defined above for Formula VI.

In another embodiment, $R_{1b}$ is chlorine and the remainder of variables are as defined above for Formula VI.

In another embodiment, $R_{1b}$ is methyl and the remainder of variables are as defined above for Formula VI.

In another embodiment, $R_{1b}$ is methoxy and the remainder of variables are as defined above for Formula VI.

Specific examples of compounds of the invention, and their respective $IC_{50}$ values, are presented in Table 1. Compounds disclosed in Table 1 are encompassed by the scope of the invention.

TABLE 1

Compounds encompassed by the invention with $IC_{50}$ values indicated (see table legend)

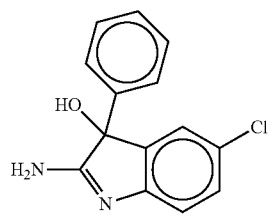

Compound 1 ****

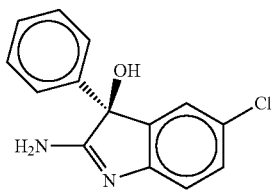

Compound 2 ****

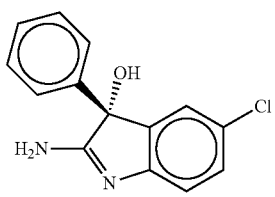

Compound 3 ****

TABLE 1-continued
Compounds encompassed by the invention
with IC$_{50}$ values indicated (see table legend)
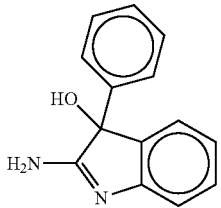 Compound 4 ****
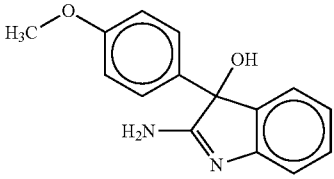 Compound 5 ****
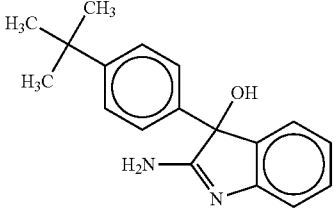 Compound 6 ***
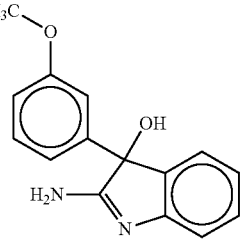 Compound 7 ****
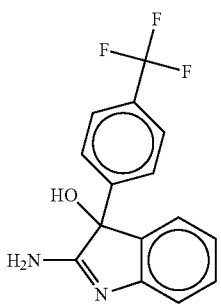 Compound 8 ****
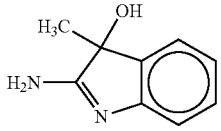 Compound 9 **
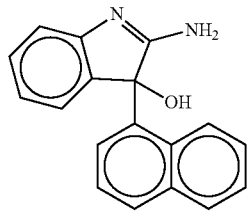 Compound 10 *****

TABLE 1-continued
Compounds encompassed by the invention
with IC$_{50}$ values indicated (see table legend)
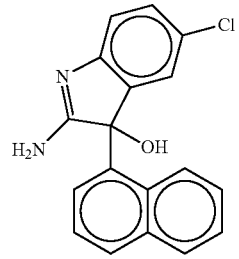
Compound 11 *****
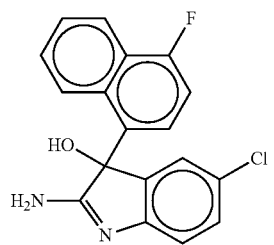
Compound 12 *****
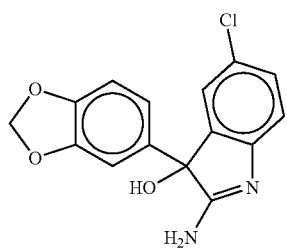
Compound 13 ****
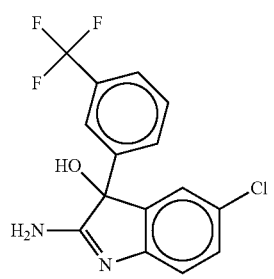
Compound 14 ****
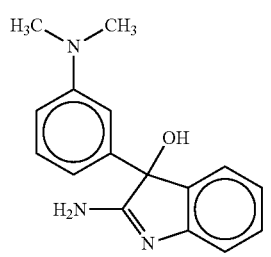
Compound 15 ****

TABLE 1-continued
Compounds encompassed by the invention
with IC$_{50}$ values indicated (see table legend)
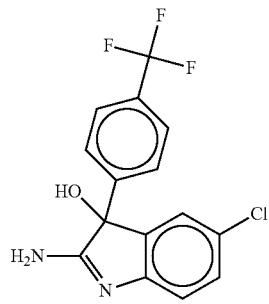 Compound 16 ****
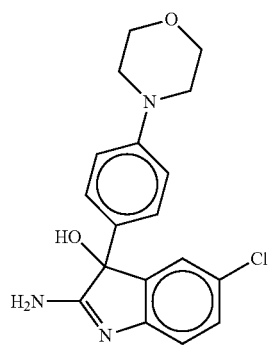 Compound 17 ***
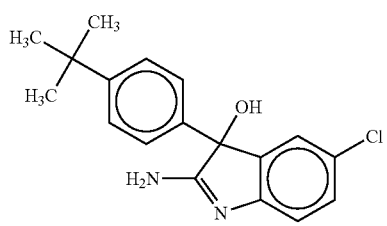 Compound 18 ****
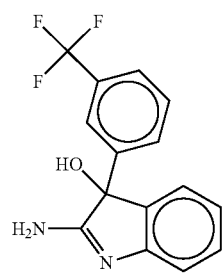 Compound 19 ****
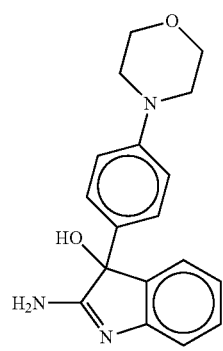 Compound 20 ***

TABLE 1-continued
Compounds encompassed by the invention
with $IC_{50}$ values indicated (see table legend)
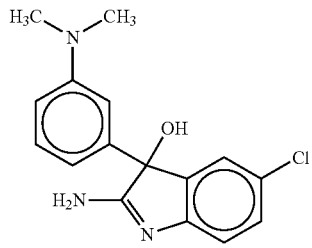  Compound 21 ****
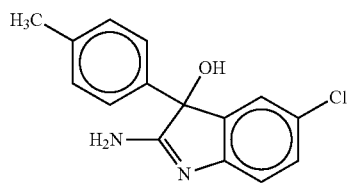  Compound 22 ***
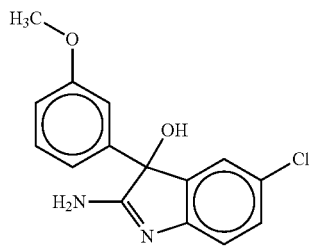  Compound 23 ****
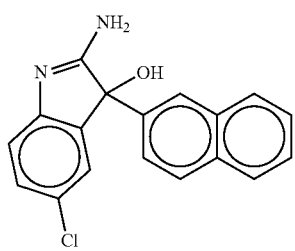  Compound 24 ****
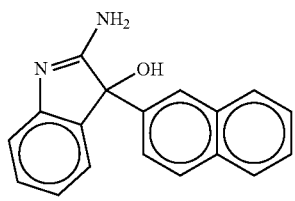  Compound 25 ****
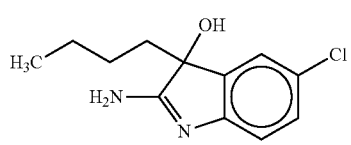  Compound 26 ****
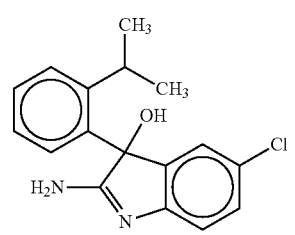  Compound 27 *****

TABLE 1-continued
Compounds encompassed by the invention
with IC$_{50}$ values indicated (see table legend)
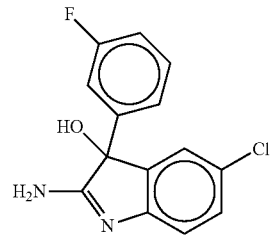
Compound 28 ****
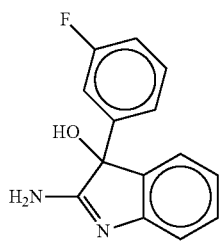
Compound 29
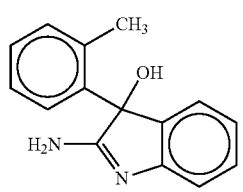
Compound 30 ****
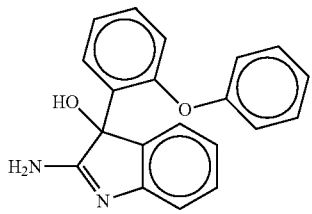
Compound 31
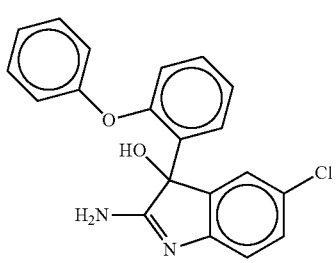
Compound 32
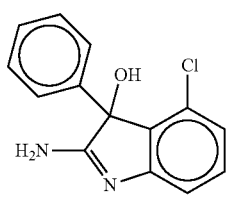
Compound 33 ****
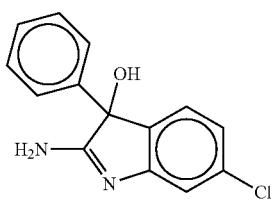
Compound 34 ***

TABLE 1-continued
Compounds encompassed by the invention
with IC$_{50}$ values indicated (see table legend)
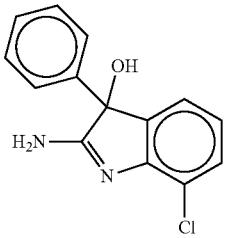 Compound 35 **
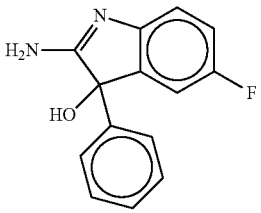 Compound 36 ****
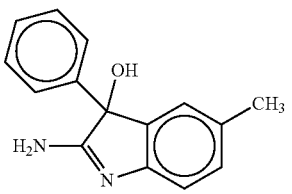 Compound 37 *****
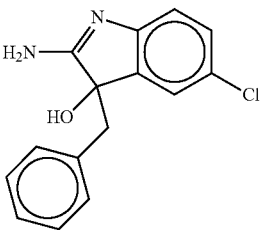 Compound 38 *****
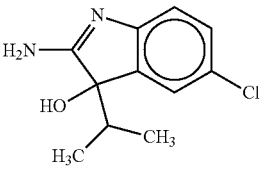 Compound 39 ****
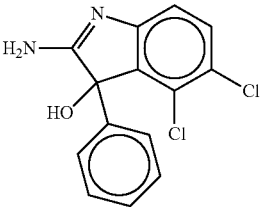 Compound 40 ****
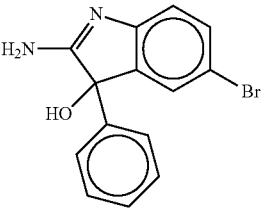 Compound 41 *****

TABLE 1-continued
Compounds encompassed by the invention
with IC$_{50}$ values indicated (see table legend)
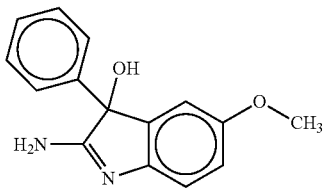
Compound 42 ****
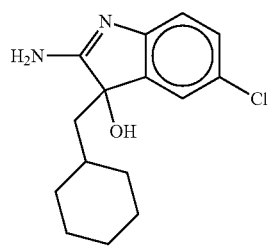
Compound 43 *****
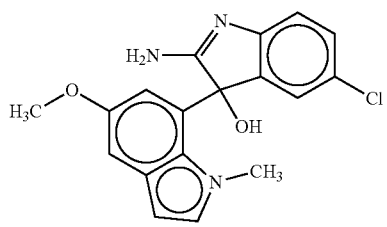
Compound 44 *
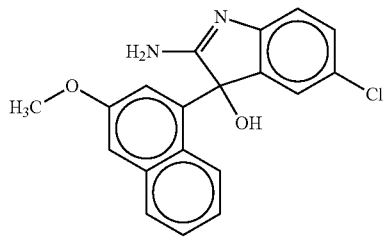
Compound 45 *
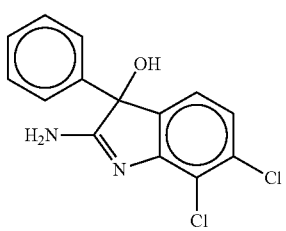
Compound 46 **
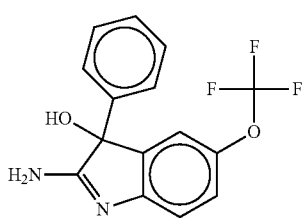
Compound 47 **
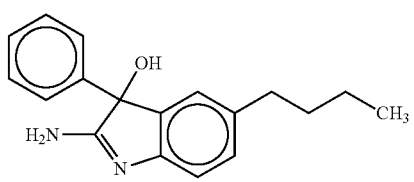
Compound 48 ***

TABLE 1-continued
Compounds encompassed by the invention
with IC$_{50}$ values indicated (see table legend)
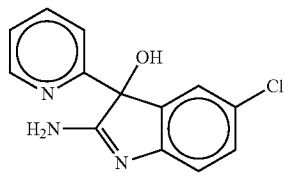
Compound 49 **
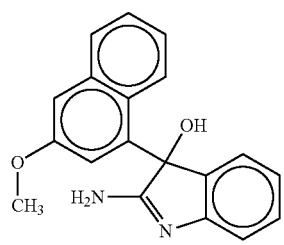
Compound 50
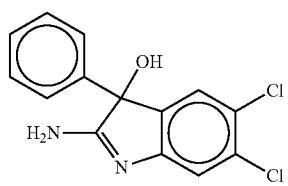
Compound 51 ***
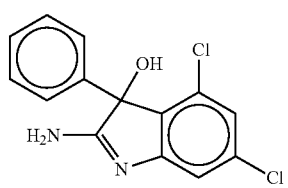
Compound 52 **
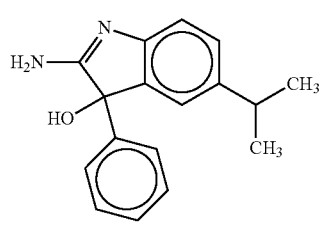
Compound 53 ***
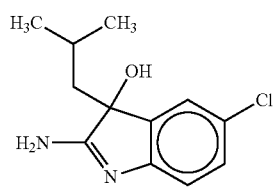
Compound 54 ****
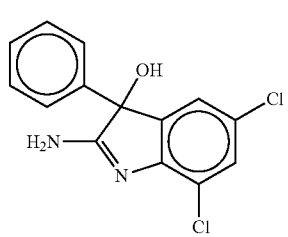
Compound 55 **

TABLE 1-continued
Compounds encompassed by the invention
with IC$_{50}$ values indicated (see table legend)
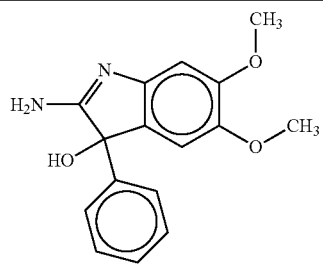 Compound 56 ****
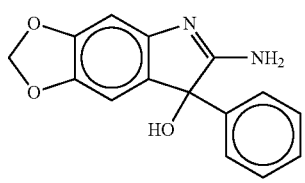 Compound 57 ****
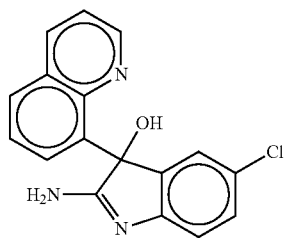 Compound 58 ****
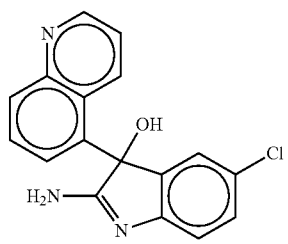 Compound 59 ****
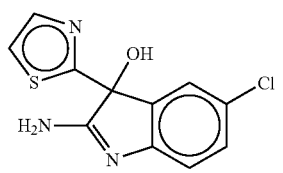 Compound 60 **
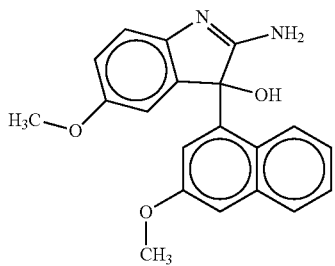 Compound 61 *
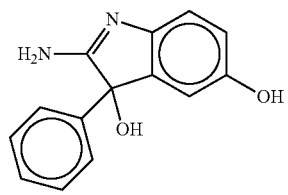 Compound 62 *

TABLE 1-continued
Compounds encompassed by the invention
with IC$_{50}$ values indicated (see table legend)
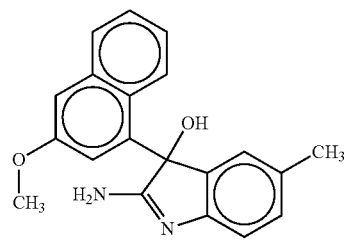
Compound 63 *
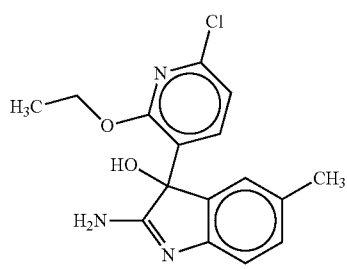
Compound 64 *
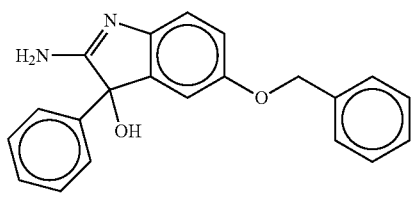
Compound 65 *
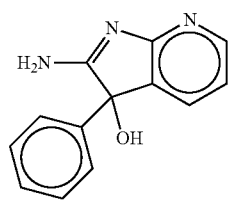
Compound 66 *
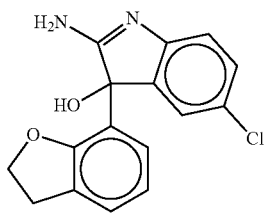
Compound 67 *****
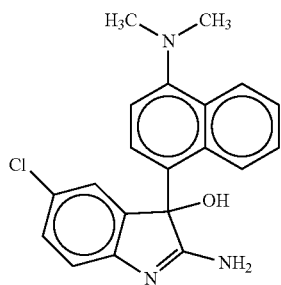
Compound 68 *****

TABLE 1-continued
Compounds encompassed by the invention
with IC$_{50}$ values indicated (see table legend)
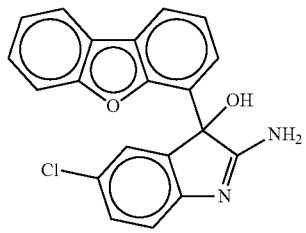  Compound 69 ****
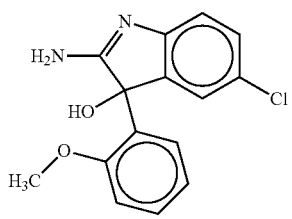  Compound 70 *****
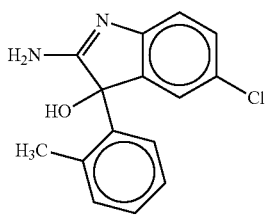  Compound 71 *****
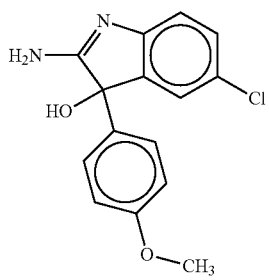  Compound 72 ***
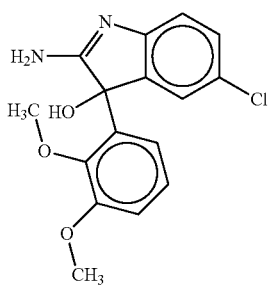  Compound 73 *****
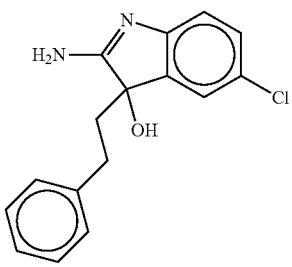  Compound 74 ****

TABLE 1-continued
Compounds encompassed by the invention
with IC$_{50}$ values indicated (see table legend)
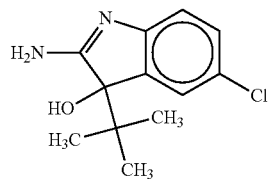  Compound 75 ****
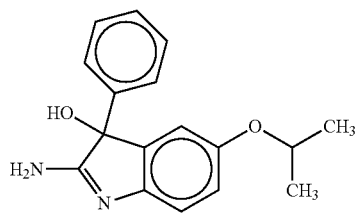  Compound 76 ****
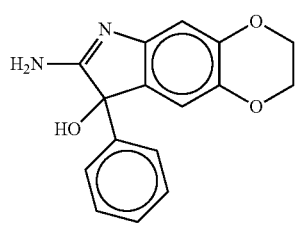  Compound 77 ****
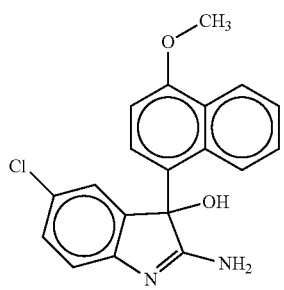  Compound 78 *****
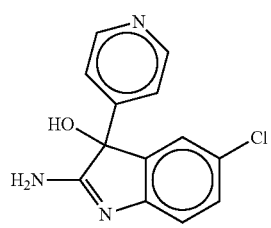  Compound 79 **
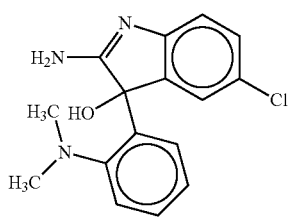  Compound 80 *****

TABLE 1-continued
Compounds encompassed by the invention
with IC$_{50}$ values indicated (see table legend)
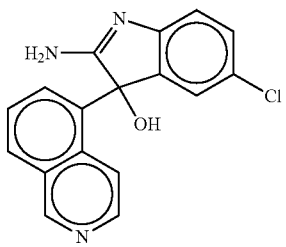 Compound 81 ****
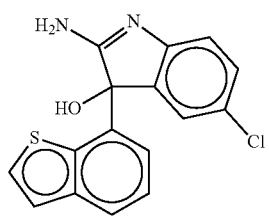 Compound 82 *****
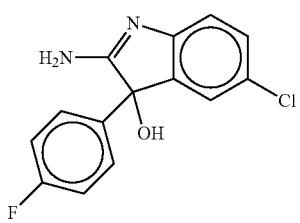 Compound 83 ****
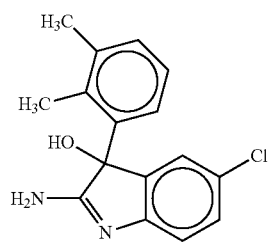 Compound 84 ****
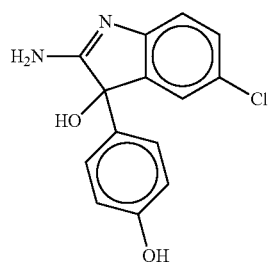 Compound 85 *
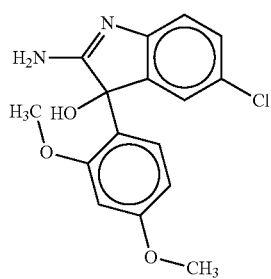 Compound 86 *****

TABLE 1-continued
Compounds encompassed by the invention
with IC$_{50}$ values indicated (see table legend)
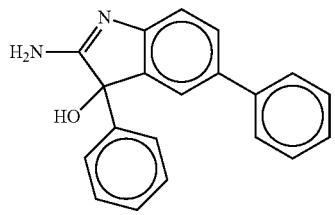
Compound 87 ****
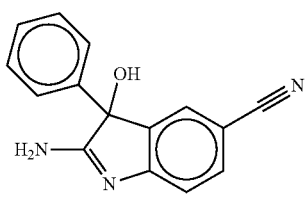
Compound 88 **
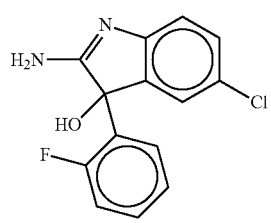
Compound 89 ****
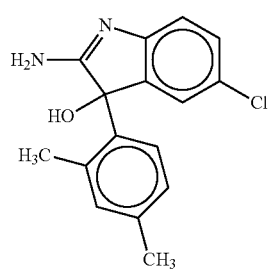
Compound 90 ****
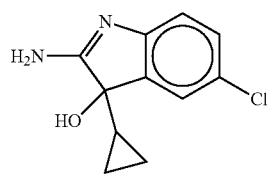
Compound 91 ****
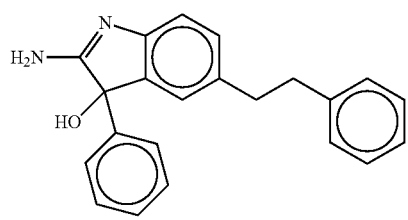
Compound 92 ****
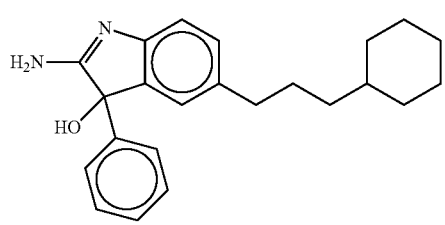
Compound 93 ****

TABLE 1-continued
Compounds encompassed by the invention
with IC$_{50}$ values indicated (see table legend)
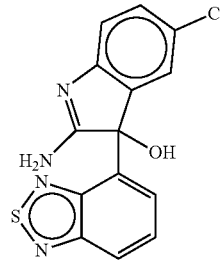
Compound 94 **
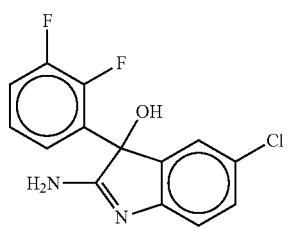
Compound 95 ****
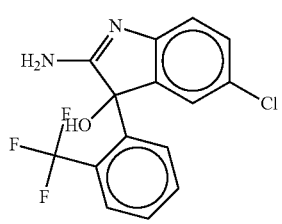
Compound 96 *****
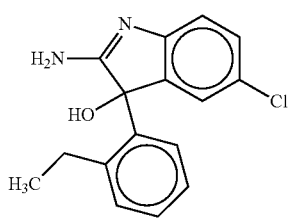
Compound 97 *****
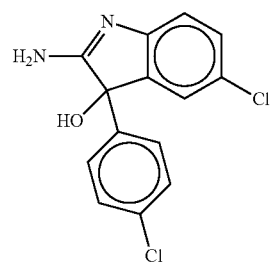
Compound 98 ****
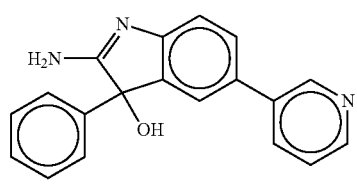
Compound 99 *
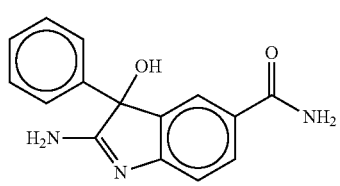
Compound 100 *

TABLE 1-continued
Compounds encompassed by the invention
with IC$_{50}$ values indicated (see table legend)
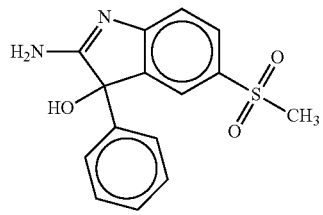 Compound 101 *
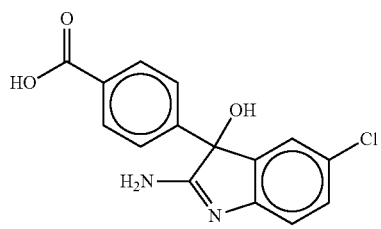 Compound 102 *
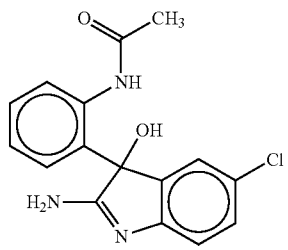 Compound 103 *
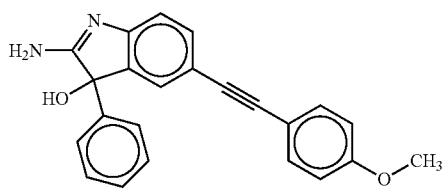 Compound 104 ****
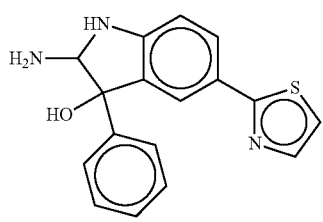 Compound 105 ****
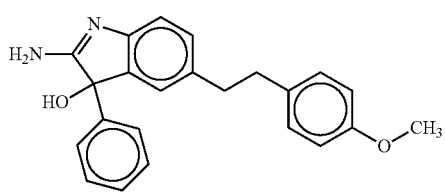 Compound 106 ****
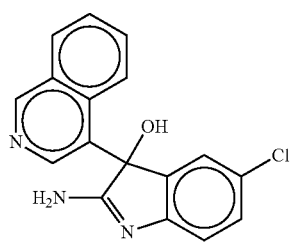 Compound 107 ****

TABLE 1-continued
Compounds encompassed by the invention
with IC$_{50}$ values indicated (see table legend)
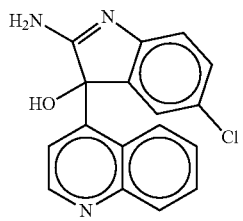
Compound 108 ****
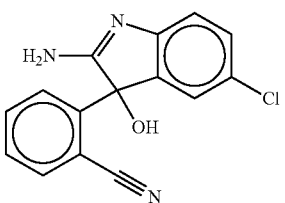
Compound 109 *
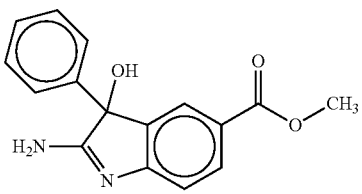
Compound 110 ***
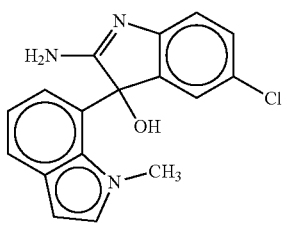
Compound 111 *****
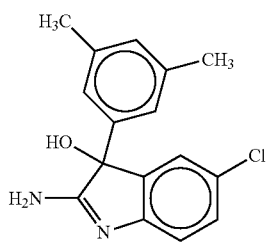
Compound 112 ****
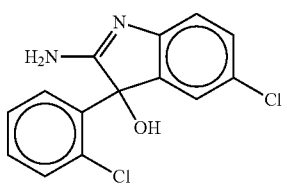
Compound 113 ****
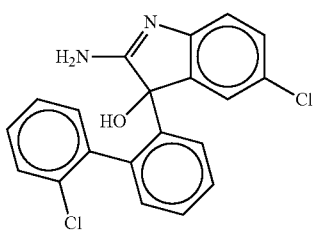
Compound 114 ****

TABLE 1-continued
Compounds encompassed by the invention
with IC$_{50}$ values indicated (see table legend)
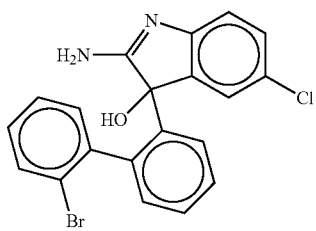
Compound 115 *****
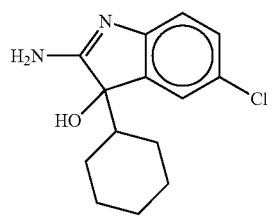
Compound 116 ****
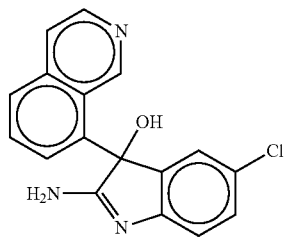
Compound 117 ****
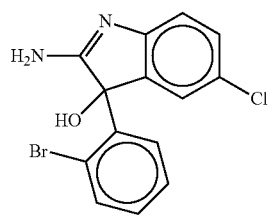
Compound 118 ****
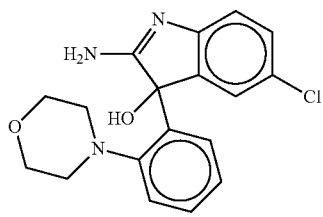
Compound 119 *****
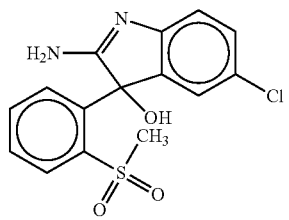
Compound 120 ***

TABLE 1-continued
Compounds encompassed by the invention
with IC$_{50}$ values indicated (see table legend)
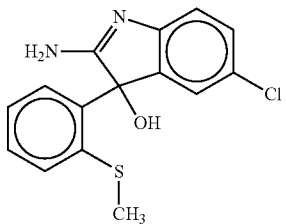
Compound 121 *****
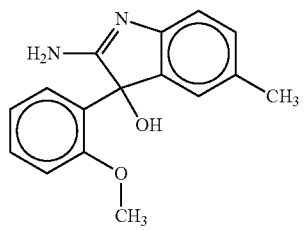
Compound 122 ****
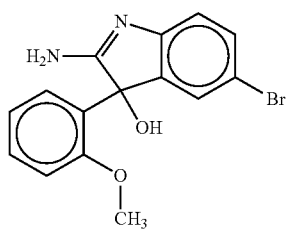
Compound 123 *****
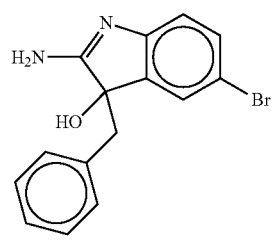
Compound 124 ****
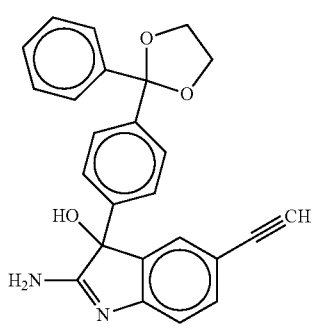
Compound 125 ****
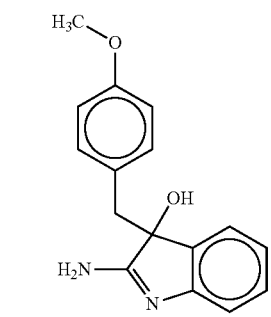
Compound 126 ****

TABLE 1-continued
Compounds encompassed by the invention
with IC$_{50}$ values indicated (see table legend)
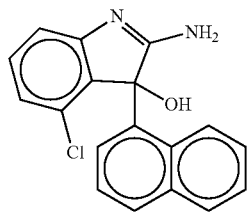  Compound 127 ***
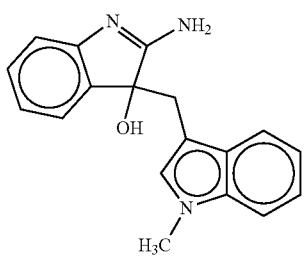  Compound 128 ****
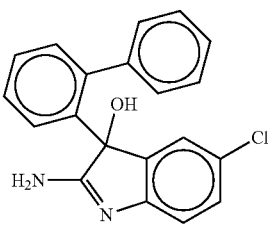  Compound 129 ****
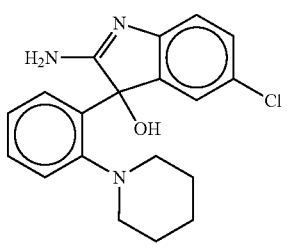  Compound 130 ****
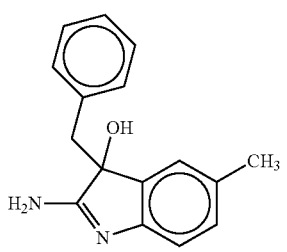  Compound 131 *****
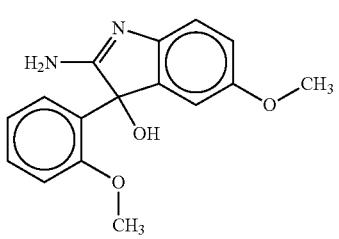  Compound 132 ****

TABLE 1-continued
Compounds encompassed by the invention
with IC$_{50}$ values indicated (see table legend)
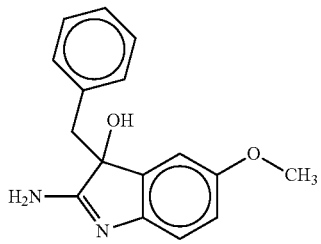
Compound 133 *****
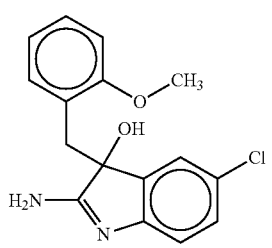
Compound 134 *****
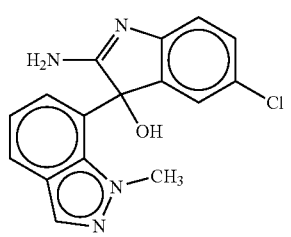
Compound 135 *****
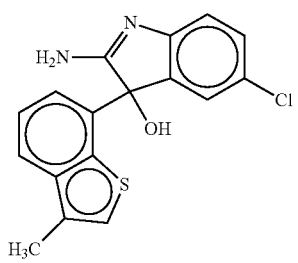
Compound 136 *****
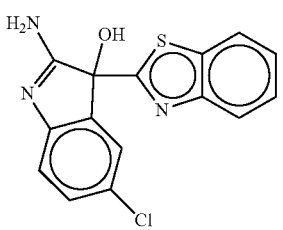
Compound 137 ****
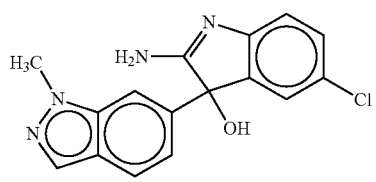
Compound 138 ****

TABLE 1-continued
Compounds encompassed by the invention
with IC$_{50}$ values indicated (see table legend)
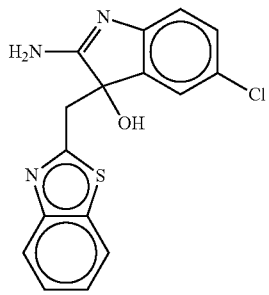
Compound 139 *****
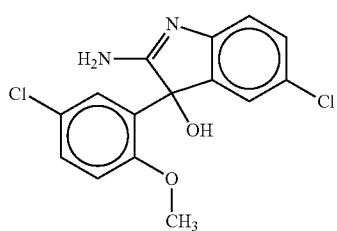
Compound 140 *****
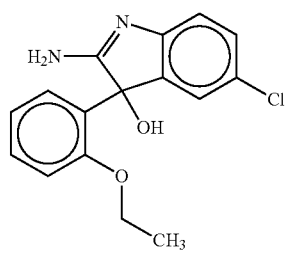
Compound 141 *****
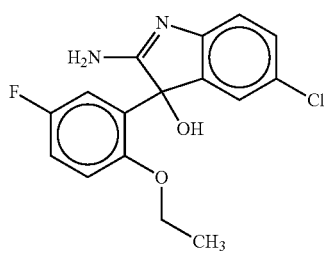
Compound 142 *****
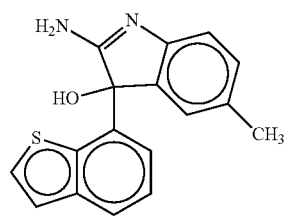
Compound 143 *****
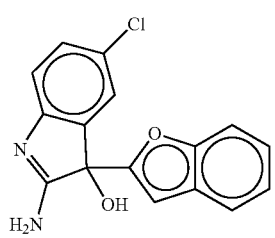
Compound 144 *****

TABLE 1-continued
Compounds encompassed by the invention
with IC$_{50}$ values indicated (see table legend)
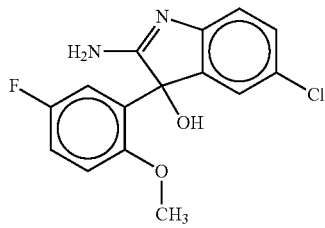 Compound 145 *****
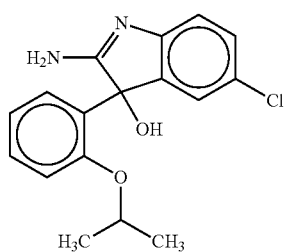 Compound 146 *****
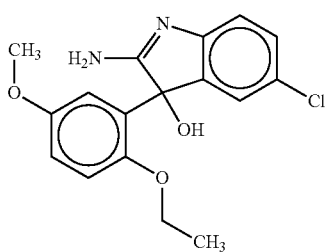 Compound 147 *****
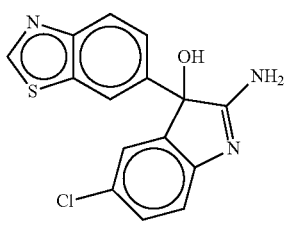 Compound 148 ****
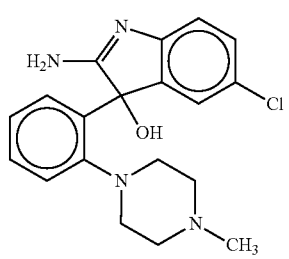 Compound 149 ***
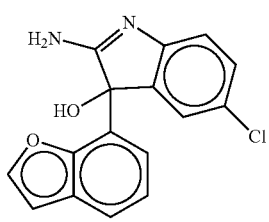 Compound 150 *****

TABLE 1-continued
Compounds encompassed by the invention
with IC$_{50}$ values indicated (see table legend)
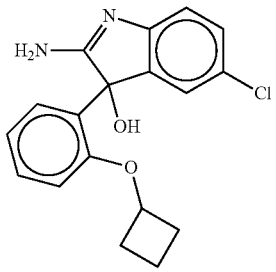 Compound 151 *****
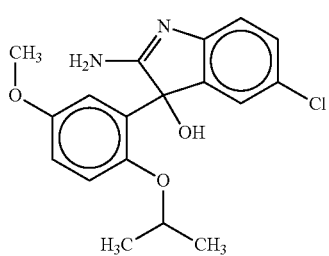 Compound 152 *****
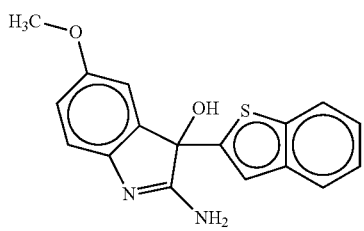 Compound 153 *****
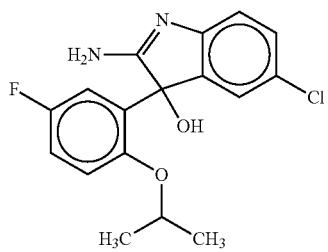 Compound 154 *****
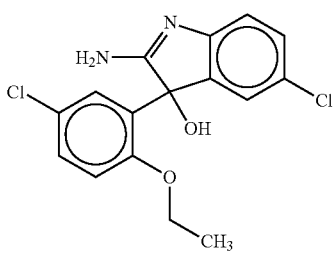 Compound 155 *****
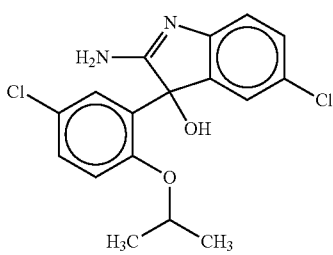 Compound 156 *****

TABLE 1-continued
Compounds encompassed by the invention
with IC$_{50}$ values indicated (see table legend)
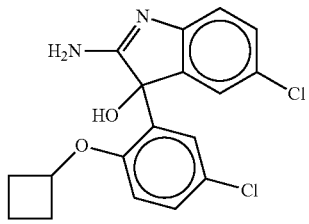 Compound 157 *****
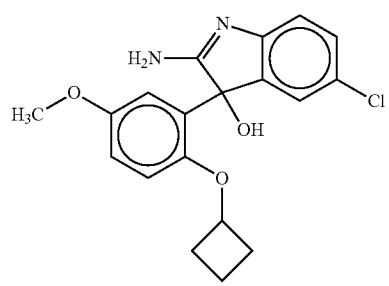 Compound 158 *****
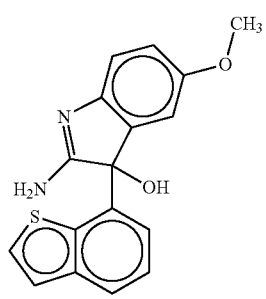 Compound 159 *****
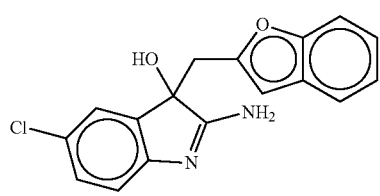 Compound 160 *****
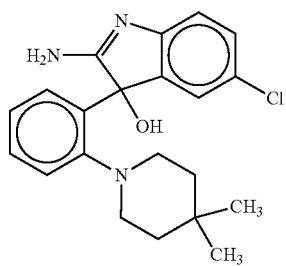 Compound 161
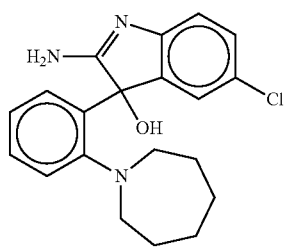 Compound 162 *****

TABLE 1-continued
Compounds encompassed by the invention
with IC$_{50}$ values indicated (see table legend)
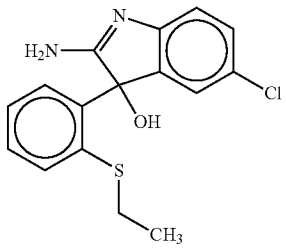 Compound 163 *****
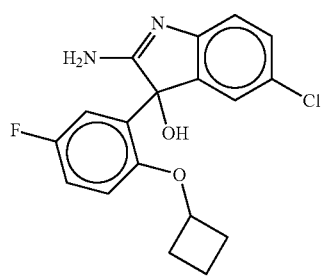 Compound 164 *****
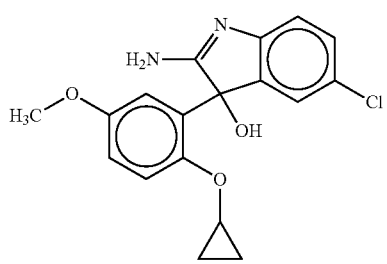 Compound 165 *****
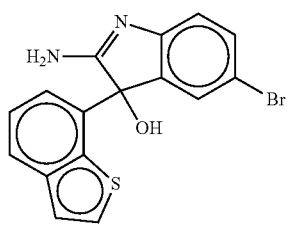 Compound 166 *****
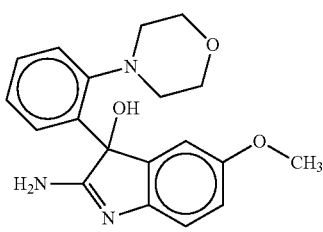 Compound 167 ****
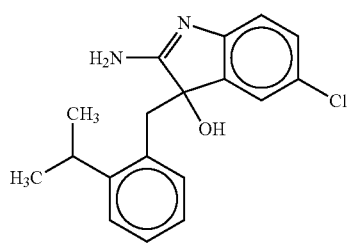 Compound 168 *****

TABLE 1-continued
Compounds encompassed by the invention
with $IC_{50}$ values indicated (see table legend)
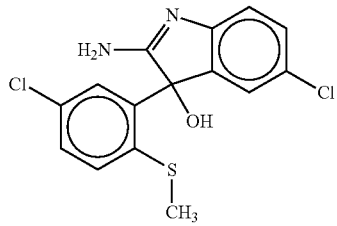
Compound 169 *****
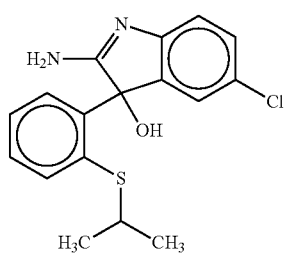
Compound 170 *****
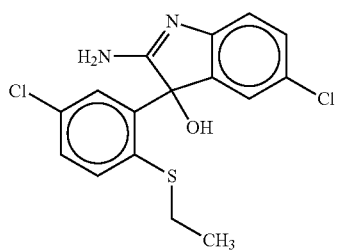
Compound 171 *****
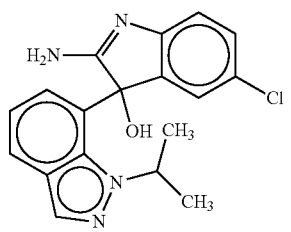
Compound 172 ***
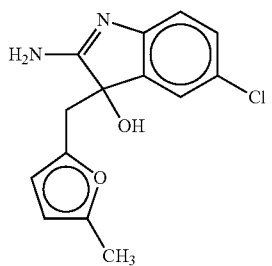
Compound 173 ****
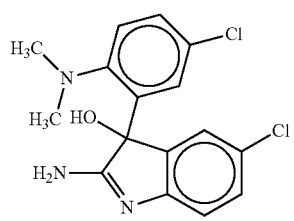
Compound 174 *****

TABLE 1-continued
Compounds encompassed by the invention
with IC$_{50}$ values indicated (see table legend)
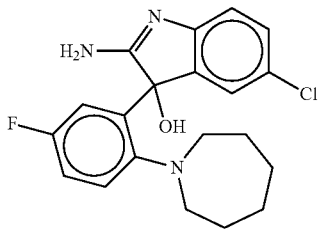 Compound 175 *****
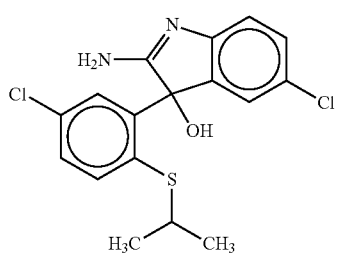 Compound 176 *****
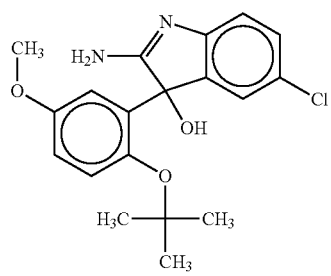 Compound 177 *****
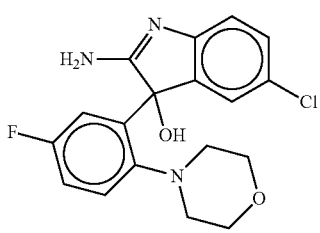 Compound 178 *****
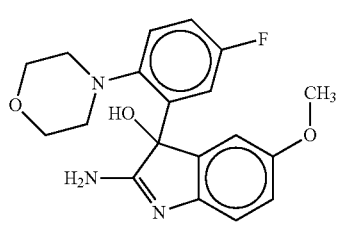 Compound 179 ****
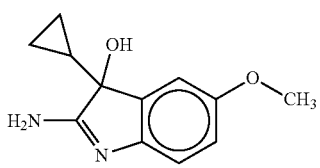 Compound 180 ****

TABLE 1-continued
Compounds encompassed by the invention
with IC$_{50}$ values indicated (see table legend)
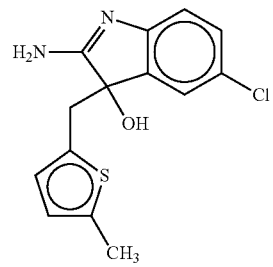 Compound 181 *****
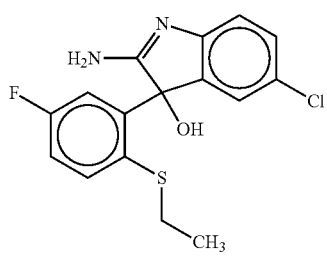 Compound 182 *****
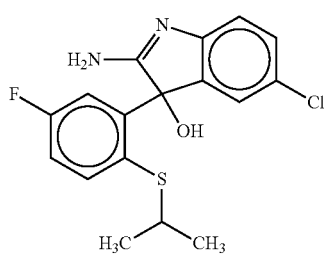 Compound 183 *****
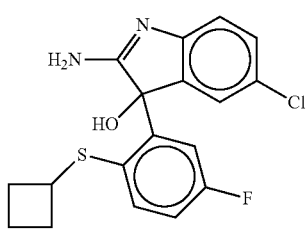 Compound 184 *****
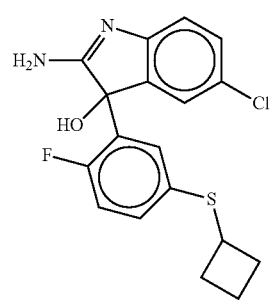 Compound 185 *****
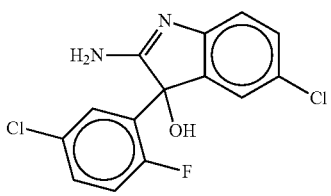 Compound 186 *****

TABLE 1-continued
Compounds encompassed by the invention
with IC$_{50}$ values indicated (see table legend)
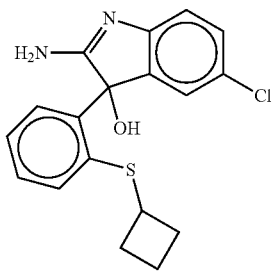
Compound 187 *****
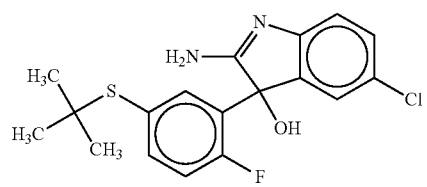
Compound 188 ****
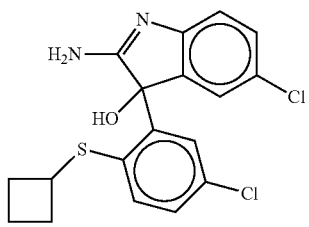
Compound 189 *****
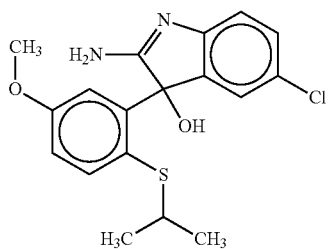
Compound 190 *****
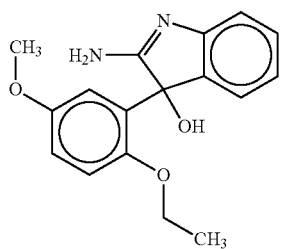
Compound 191 *****
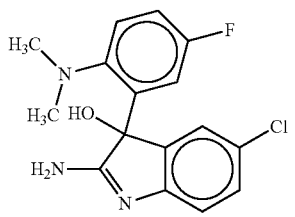
Compound 192 *****

TABLE 1-continued
Compounds encompassed by the invention
with IC$_{50}$ values indicated (see table legend)
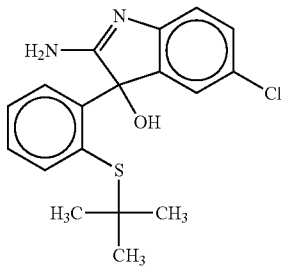 Compound 193 *****
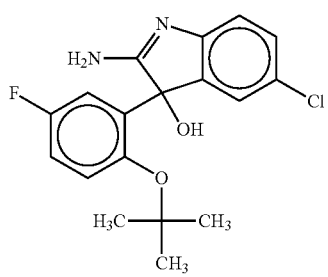 Compound 194 *****
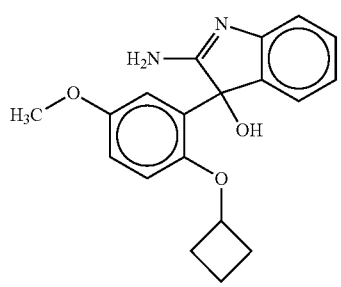 Compound 195 *****
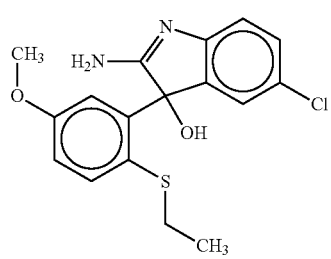 Compound 196 *****
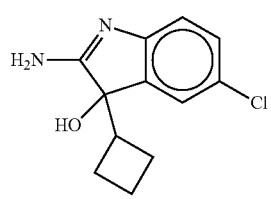 Compound 197 ****
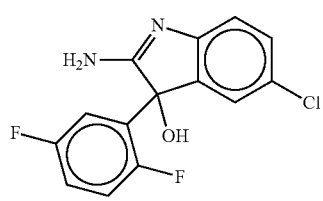 Compound 198 ****

TABLE 1-continued
Compounds encompassed by the invention
with IC$_{50}$ values indicated (see table legend)
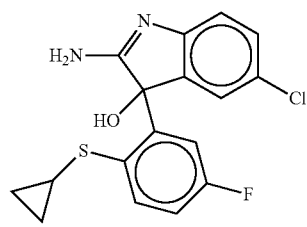
Compound 199 *****
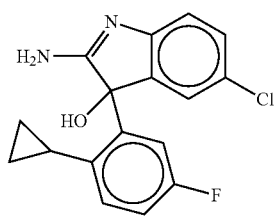
Compound 200 *****
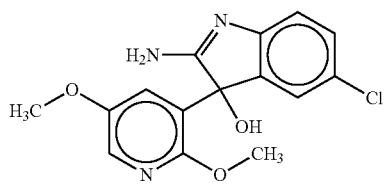
Compound 201 *****
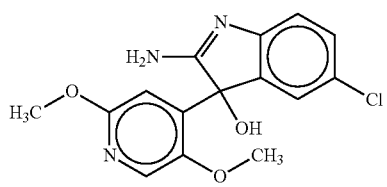
Compound 202 *****
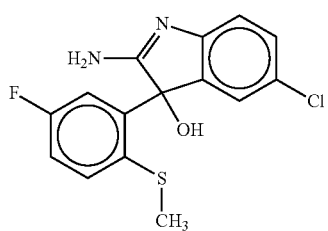
Compound 203 *****
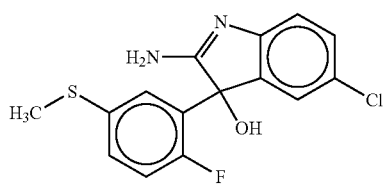
Compound 204 *****
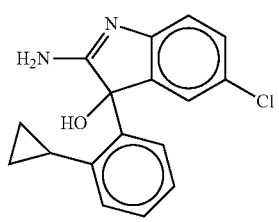
Compound 205 *****

TABLE 1-continued
*Compounds encompassed by the invention with $IC_{50}$ values indicated (see table legend)*
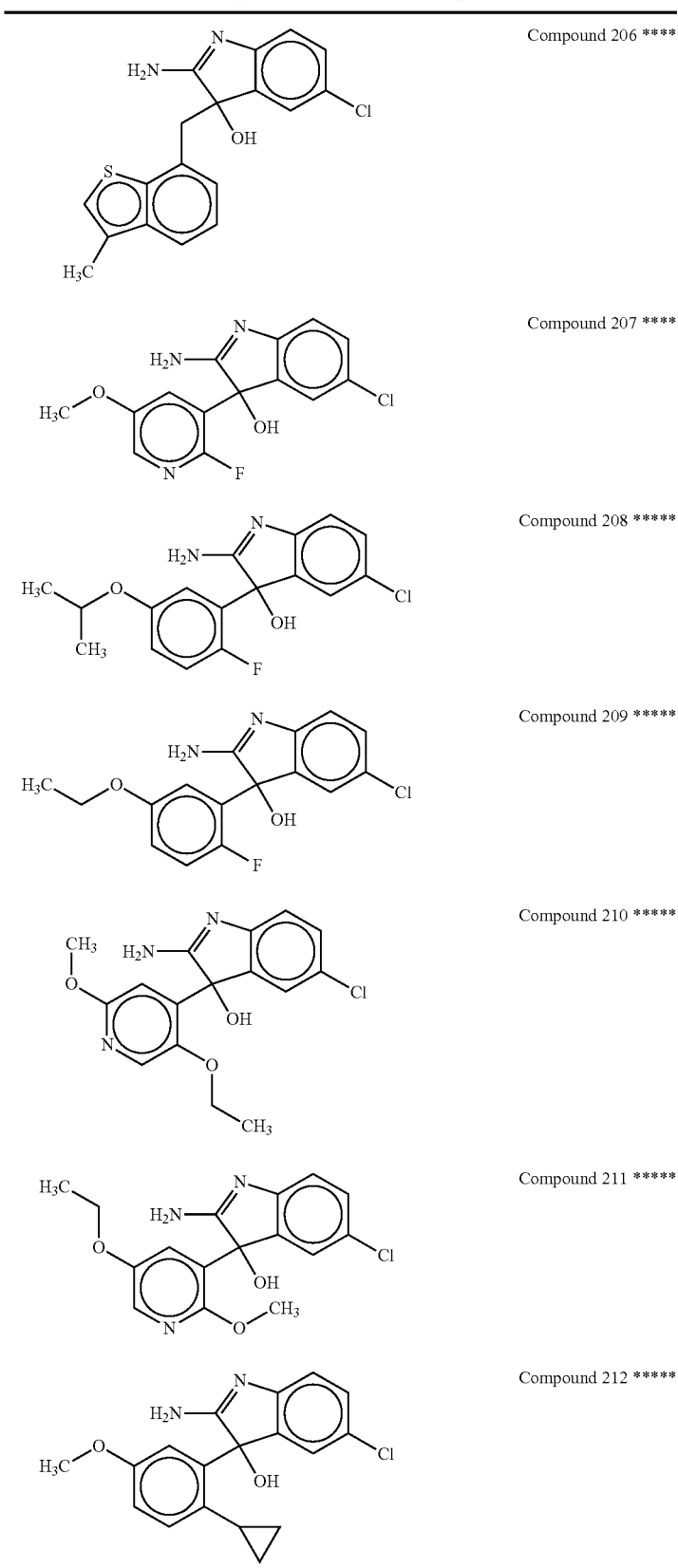
Compound 206 ****
Compound 207 ****
Compound 208 *****
Compound 209 *****
Compound 210 *****
Compound 211 *****
Compound 212 *****

TABLE 1-continued
Compounds encompassed by the invention
with IC$_{50}$ values indicated (see table legend)
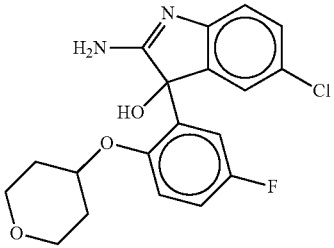 Compound 213 *****
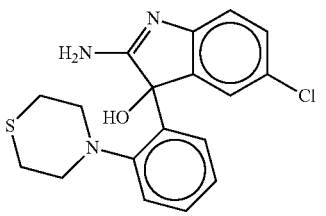 Compound 214 *****
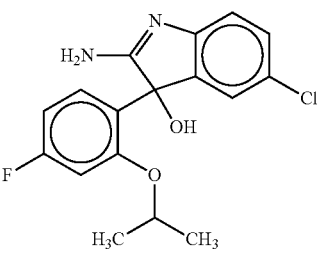 Compound 215 *****
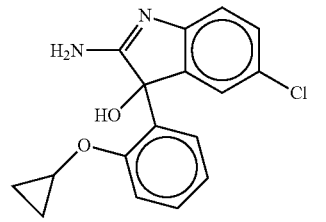 Compound 216 *****
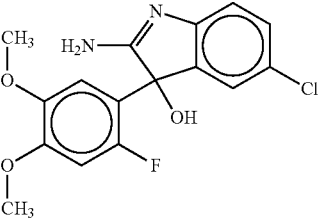 Compound 217 *****
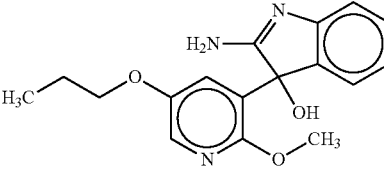 Compound 218 *****

TABLE 1-continued
Compounds encompassed by the invention
with IC$_{50}$ values indicated (see table legend)
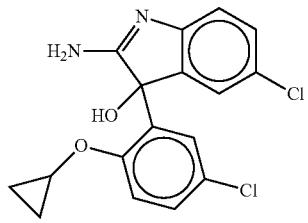 Compound 219 *****
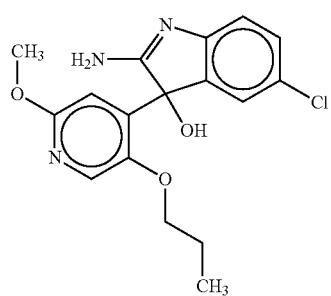 Compound 220 *****
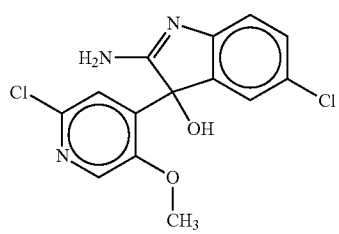 Compound 221 ****
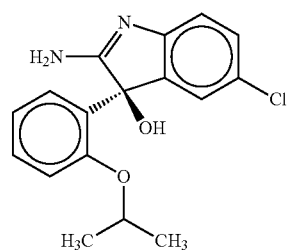 Compound 222 *****
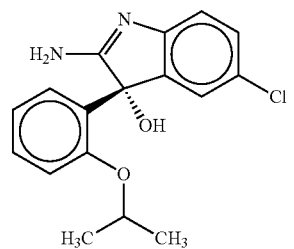 Compound 223 *****
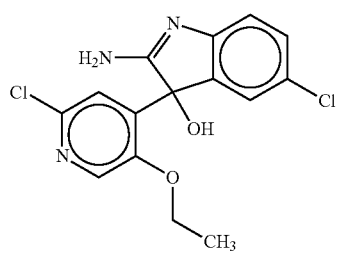 Compound 224 *****

TABLE 1-continued
Compounds encompassed by the invention
with IC$_{50}$ values indicated (see table legend)
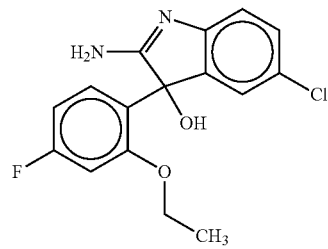
Compound 225 *****
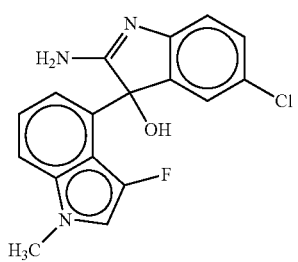
Compound 226 ****
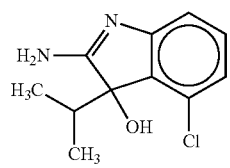
Compound 227 ****
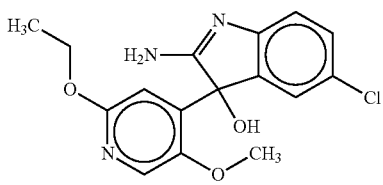
Compound 228 *****
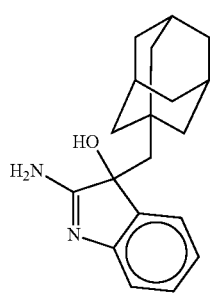
Compound 229 ****
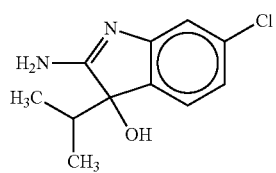
Compound 230 ****
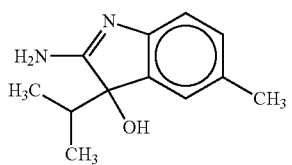
Compound 231 ****

TABLE 1-continued
Compounds encompassed by the invention
with IC$_{50}$ values indicated (see table legend)
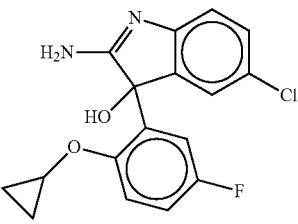
Compound 232 *****
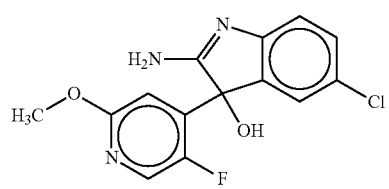
Compound 233 ****
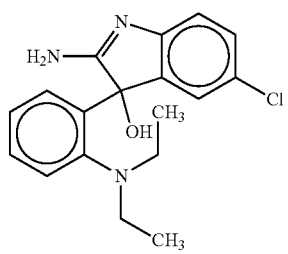
Compound 234 *****
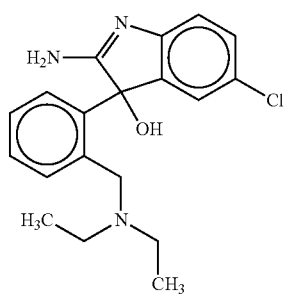
Compound 235
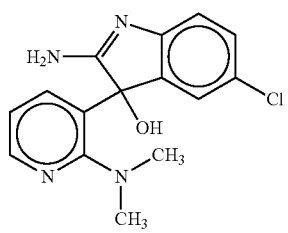
Compound 236 ****
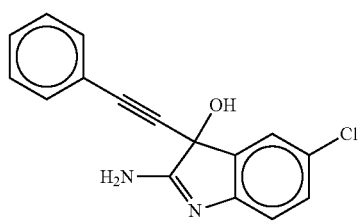
Compound 237 **

TABLE 1-continued
Compounds encompassed by the invention
with IC$_{50}$ values indicated (see table legend)
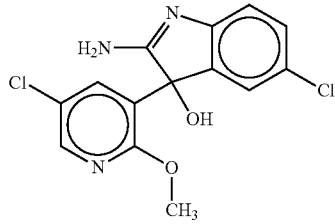 Compound 238 *****
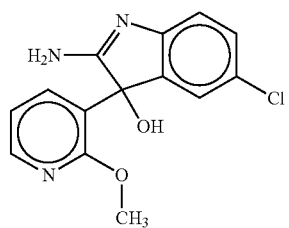 Compound 239 ****
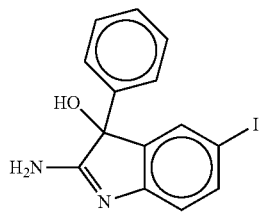 Compound 240
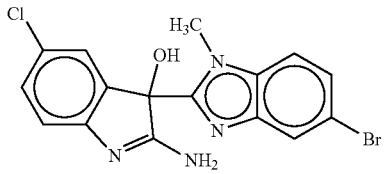 Compound 241 ****
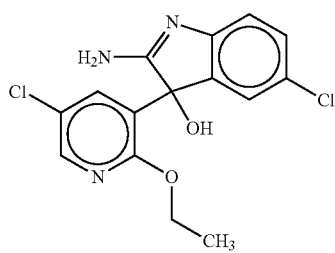 Compound 242 *****
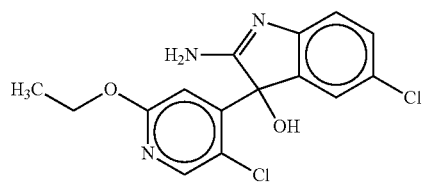 Compound 243 *****
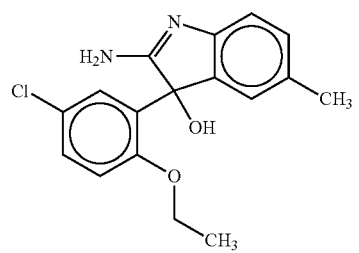 Compound 244 *****

TABLE 1-continued
Compounds encompassed by the invention
with IC$_{50}$ values indicated (see table legend)
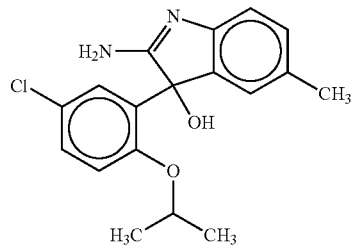
Compound 245 *****
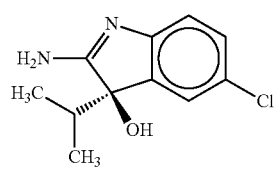
Compound 246 ****
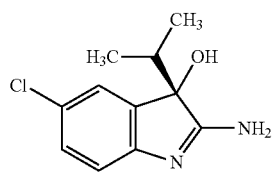
Compound 247 ****
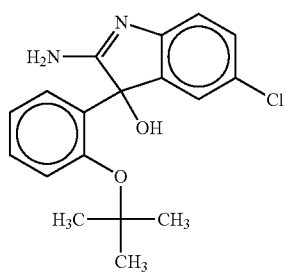
Compound 248 *****
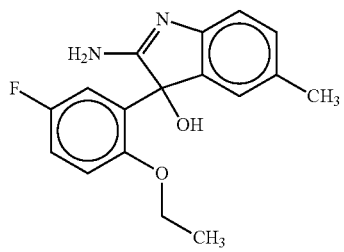
Compound 249 *****
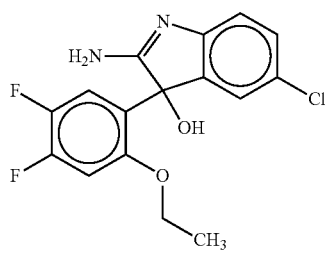
Compound 250 *****

TABLE 1-continued
Compounds encompassed by the invention
with IC$_{50}$ values indicated (see table legend)
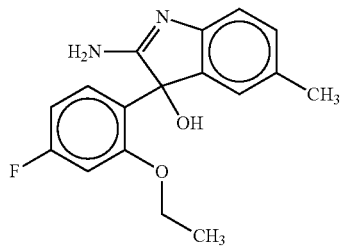
Compound 251 *****
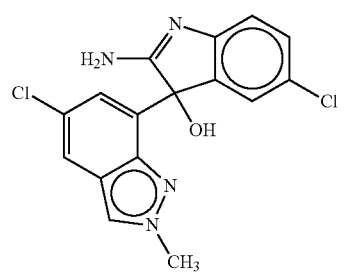
Compound 252 *****
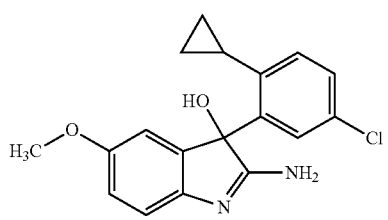 [SMILES: COc1ccc2c(c1)C(O)(c1cc(Cl)ccc1C1CC1)C(N)=N2]
Compound 253 *****
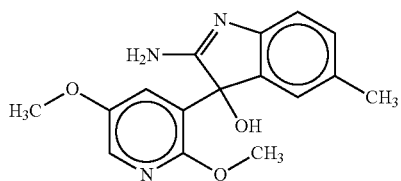
Compound 254 *****
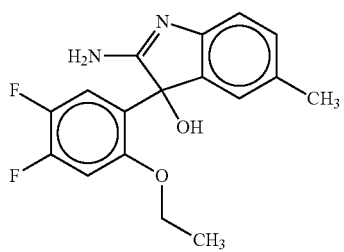
Compound 255 *****
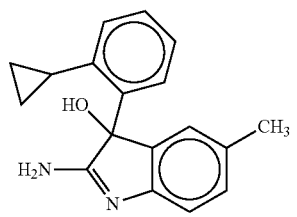
Compound 256 *****

TABLE 1-continued
Compounds encompassed by the invention
with IC$_{50}$ values indicated (see table legend)
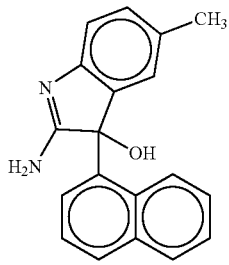 Compound 257 *****
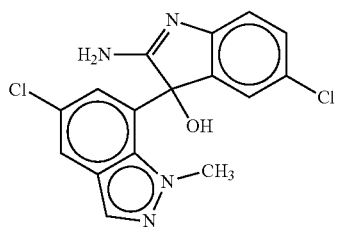 Compound 258 *****
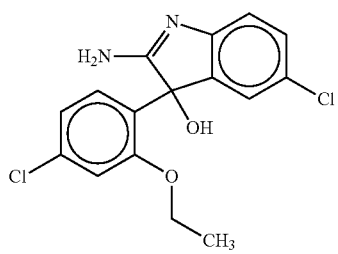 Compound 259 *****
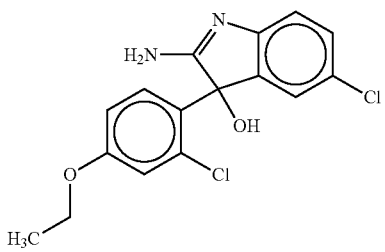 Compound 260 ****
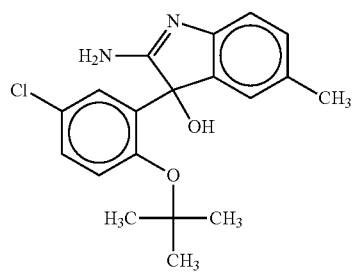 Compound 261 *****
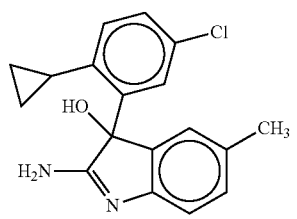 Compound 262 *****

TABLE 1-continued
Compounds encompassed by the invention
with IC$_{50}$ values indicated (see table legend)
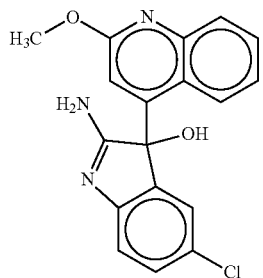
Compound 263 *****
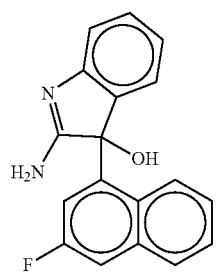
Compound 264 ****
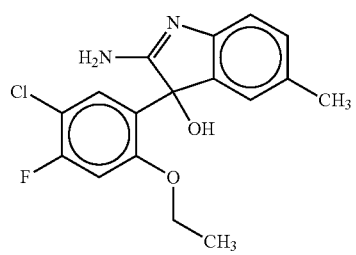
Compound 265 *****
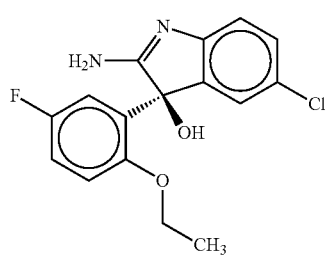
Compound 266 *****
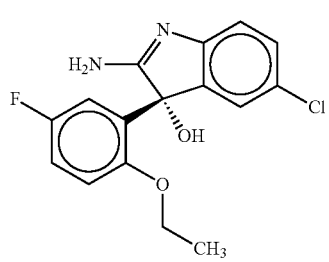
Compound 267 *****

TABLE 1-continued
Compounds encompassed by the invention
with IC$_{50}$ values indicated (see table legend)
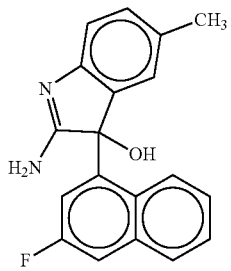
Compound 268 *****
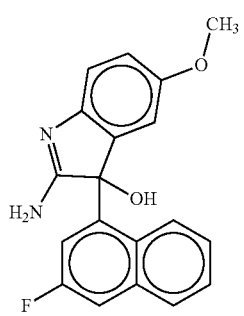
Compound 269 *****
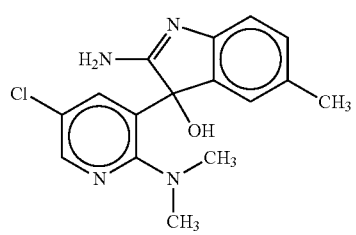
Compound 270 *****
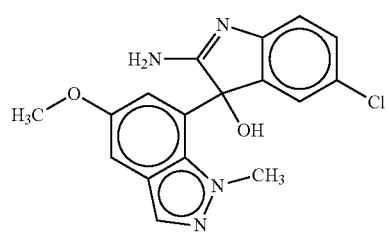
Compound 271 ****
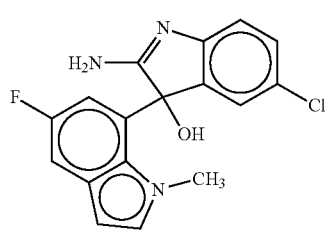
Compound 272 ****

TABLE 1-continued

Compounds encompassed by the invention
with $IC_{50}$ values indicated (see table legend)

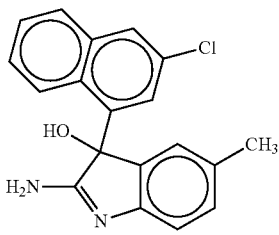

Compound 273 *****

\* represents $IC_{50}$ from less than 15 μM to 5 μM;
\*\* represents $IC_{50}$ from less than 5 μM to 1 μM;
\*\*\* represents $IC_{50}$ from less than 1 μM to 500 nM;
\*\*\*\* represents $IC_{50}$ from less than 500 nM to 100 nM;
\*\*\*\*\* represents $IC_{50}$ from less than 100 nM to 1 nM.
The indicated $IC_{50}$ values were determined with respect to reductions in parasitemia observed for *P. falciparum* strain 3D7.

The compounds of the invention may be present in the form of pharmaceutically acceptable salts. For use in medicines, the salts of the compounds of the invention refer to non-toxic "pharmaceutically acceptable salts." Pharmaceutically acceptable salt forms include pharmaceutically acceptable acidic/anionic or basic/cationic salts.

Pharmaceutically acceptable acidic/anionic salts include, the acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, malonate, mandelate, mesylate, methylsulfate, mucate, napsylate, nitrate, pamoate, pantothenate, phosphate/diphosphate, polygalacturonate, salicylate, stearate, subacetate, succinate, sulfate, hydrogensulfate, tannate, tartrate, teoclate, tosylate, and triethiodide salts.

Pharmaceutically acceptable basic/cationic salts include, the sodium, potassium, calcium, magnesium, diethanolamine, N-methyl-D-glucamine, L-arginine, ammonium, ethanolamine, piperazine and triethanolamine salts.

The disclosed compounds can be used alone (i.e. as a monotherapy) or in combination with another therapeutic agent effective for treating malaria.

Alternatively, a pharmaceutical composition of the invention may comprise an antimalarial compound disclosed herein or a pharmaceutical salt thereof, as the only pharmaceutically active agent in the pharmaceutical composition. The disclosed antimalarial compounds can be used alone or in a combination therapy with one or more additional agents for the treatment of malaria.

A pharmaceutical composition of the invention may, alternatively or in addition to an antimalarial compound disclosed herein comprise a pharmaceutically acceptable salt of an antimalarial compound disclosed herein or a prodrug or pharmaceutically active metabolite of such a compound or salt and one or more pharmaceutically acceptable carriers therefore. Alternatively, a pharmaceutical composition of the invention may comprise an antimalarial compound disclosed herein or a pharmaceutical salt thereof as the only pharmaceutically active agent in the pharmaceutical composition.

The invention includes a therapeutic method for treating malaria in a subject in need thereof comprising administering to the subject in need thereof an effective amount of an antimalarial compound disclosed herein or a pharmaceutically acceptable salt thereof or a composition thereof (e.g., a pharmaceutical composition comprising an antimalarial compound and a pharmaceutically-acceptable carrier). Compounds disclosed herein can be used in the treatment of malaria. Thus, in one embodiment, the invention relates to the use of a compound disclosed herein for the treatment of malaria in a subject in need thereof. In other embodiments, the invention relates to the use of a compound disclosed herein in the treatment of malaria and the use of a compound disclosed herein in the manufacture of a medicament for the treatment of malaria. As used herein, "treating" or "treatment" includes both therapeutic and prophylactic treatment. Therapeutic treatment includes reducing the symptoms associated with a disease or condition and/or increasing the longevity of a subject with the disease or condition. Prophylactic treatment includes delaying the onset of a disease or condition in a subject at risk of developing the disease or condition or reducing the likelihood that a subject will then develop the disease or condition in a subject that is at risk for developing the disease or condition.

As used herein, an "effective amount" is an amount sufficient to achieve a desired effect under the conditions of administration, in vitro, in vivo or ex vivo, such as, for example, an amount sufficient to treat malaria in a subject. The effectiveness of a compound can be determined by suitable methods known by those of skill in the art including those described herein.

As defined herein, a "therapeutically effective amount" is an amount sufficient to achieve a desired therapeutic or prophylactic effect in a subject in need thereof under the conditions of administration, such as, for example, an amount sufficient treat malaria in a subject. The effectiveness of a therapy can be determined by suitable methods known by those of skill in the art.

An embodiment of the invention includes administering an antimalarial compound disclosed herein, or composition thereof, in a combination therapy with one or more additional agents for the treatment of malaria. Agents for the treatment of malaria include quinine, atovaquone, chloroquine, cycloguanil, hydroxychloroquine, amodiaquine, pyrimethamine, sulphadoxine, proguanil, mefloquine, halofantrine, pamaquine, primaquine, artemisinin, artemether, artesunate, artenimol, lumefantrine, dihydroartemisinin, piperaquine, artether, doxycycline and clindamycin.

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Additionally, the compounds of the present invention can be administered intranasally or transdermally. It will be obvious to those skilled in the art that the following dosage forms may comprise as the active ingredient, either compounds or a corresponding pharmaceutically acceptable salt of a compound of the present invention.

For preparing pharmaceutical compositions from the compounds of the present invention, pharmaceutically acceptable carriers can either be solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material. In powders, the carrier is a finely divided solid which is in a mixture with the finely divided active ingredient.

In tablets, the active ingredient is mixed with the carrier having the necessary binding properties in suitable proportions and compacted in the shape and size desired.

The powders and tablets preferably contain from about one to about seventy percent of the active ingredient. Suitable carriers are magnesium carbonate, magnesium stearate, talc, sugar, lactose, pectin, dextrin, starch, gelatin, tragacanth, methylcellulose, sodium carboxymethylcellulose, a low-melting wax, cocoa butter, and the like. Tablets, powders, cachets, lozenges, fast-melt strips, capsules and pills can be used as solid dosage forms containing the active ingredient suitable for oral administration.

Suitable for enteral administration are also suppositories that consist of a combination of the active ingredient and a suppository base. Suitable as suppository bases are, for example, natural or synthetic triglycerides, paraffins, polyethylene glycols or higher alkanols. It is also possible to use gelatin rectal capsules that contain a combination of the active ingredient and a base material; suitable base materials are, for example, liquid triglycerides, polyethylene glycols or paraffin hydrocarbons. For preparing suppositories, a low-melting wax, such as a mixture of fatty acid glycerides or cocoa butter, is first-melted and the active ingredient is dispersed homogeneously therein, as by stirring. The molten homogeneous mixture is then poured into convenient sized molds, allowed to cool, and thereby to solidify.

Liquid form preparations include solutions, suspensions, retention enemas, and emulsions, for example, water or water propylene glycol solutions. For parenteral injection, liquid preparations can be formulated in solution in aqueous polyethylene glycol solution.

Aqueous solutions suitable for oral administration can be prepared by dissolving the active ingredient in water and adding suitable colorants, flavors, stabilizing, and thickening agents as desired. Aqueous suspensions for oral administration can be prepared by dispersing the finely divided active ingredient in water with viscous material, such as natural or synthetic gums, resins, methylcellulose, sodium carboxymethylcellulose, and other well-known suspending agents.

The pharmaceutical composition is preferably in unit dosage form. In such form, the composition is subdivided into unit doses containing appropriate quantities of the active ingredient. The unit dosage form can be a packaged preparation, the package containing discrete quantities of, for example, tablets, powders, and capsules in vials or ampules.

Also, the unit dosage form can be a tablet, cachet, capsule, or lozenge itself, or it can be the appropriate amount of any of these in packaged form.

The dosages may be varied depending upon the requirements of the patient, the severity of the condition being treated, and the compound being employed. Determination of the proper dosage for a particular situation is within the skill in the art. Also, the pharmaceutical composition may contain, if desired, other compatible therapeutic agents.

SYNTHETIC METHODS

As described herein, it has been found that 2-aminoindole compounds of the invention can be produced by aminating a 2-oxindole compound with tert-butyldimethylsilyl amine (TBDMSNH$_2$), for example, in the presence of SnCl$_4$ and an agent selected from triethylamine, N-ethyldiisopropylamine or N-methyl morpholine (NMM). It has also been found that aminating 2-oxindole compounds with TBDMSNH$_2$ preserves stereospecificity. Thus, in a further embodiment, the invention relates to methods of aminating a 2-oxindole compound to produce a 2-aminoindole compound using tert-butyldimethylsilyl amine (TBDMSNH$_2$) in the presence of SnCl$_4$ and an agent selected from triethylamine, N-ethyldiisopropylamine or N-methyl morpholine (NMM). Representative schemes for such a method are described herein in Examples 8-10, Schemes 20-22.

In a particular embodiment, TBDMSNH$_2$ is used in an enantioselective method of preparing a 2-aminoindole. A representative scheme for such a method is described herein in Example 10, Scheme 22.

In one embodiment, the invention relates to a method of preparing a compound represented by Formula VII:

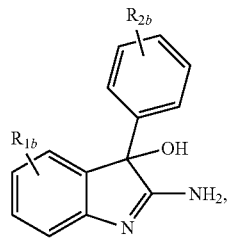

(VII)

or a pharmaceutically acceptable salt thereof,
wherein
Each $R_{1b}$ is independently selected from hydrogen, halogen (e.g., fluorine, chlorine, bromine, iodine), nitro, cyano, hydroxy, $(C_1$-$C_6)$alkyl, $(C_1$-$C_6)$alkenyl, $(C_1$-$C_6)$alkynyl, $(C_1$-$C_6)$alkoxy, aryl, heteroaryl, cycloalkyl, heterocyclyl, aryl($C_1$-$C_3$)alkyl, heteroaryl($C_1$-$C_3$)alkyl, cycloalkyl($C_1$-$C_3$)alkyl, heterocyclyl($C_1$-$C_3$)alkyl, hydroxy($C_1$-$C_3$)alkyl, $N(R_{3b})_2$, $C(=NOH)NH_2$, $NR_{3b}CON(R_{3b})_2$, $CON(R_{3b})_2$, $CO_2R_{3b}$, $COR_{4b}$, $OC(O)R_3$, $SO_2N(R_{3b})_2$, $SO_2R_{4b}$, $NR_3COR_4$, $NR_{3b}CO_2R_{4b}$, $NR_{3b}SO_2R_{4b}$ and $OC(=O)N(R_{3b})_2$, each optionally substituted with one or more groups represented by $R_{2b}$;
Each $R_{2b}$ is independently selected from halogen (e.g., fluorine, chlorine, bromine, iodine), nitro, cyano, hydroxy, $(C_1$-$C_4)$alkyl, halo($C_1$-$C_3$)alkyl, hydroxy($C_1$-$C_4$)alkyl, $(C_1$-$C_4)$alkoxy, halo($C_1$-$C_4$)alkoxy, aryl, haloaryl, cycloalkyl, aryl($C_1$-$C_3$)alkyl, aryl($C_1$-$C_4$)alkoxy, heterocyclyl, $N(R_{3b})_2$, $C(=NOH)NH_2$, $NR_{3b}CON(R_{3b})_2$, $CON(R_{3b})_2$, $CO_2R_{3b}$, $COR_{4b}$, $OC(O)R_{3b}$, S, $SO_2N(R_{3b})_2$, $SO_2R_{4b}$, $SR_{4b}$, $S(C_1$-$C_3)$alkylcycloalkyl, $NR_{3b}COR_{4b}$, $NR_{3b}CO_2R_{4b}$, $NR_{3b}SO_2R_{4b}$, $S(=O)R_{3b}$, —O-cycloalkyl, —O-heterocyclyl, adamantyl, $OC(=O)N(R_3)_2$,

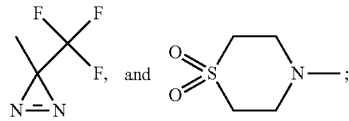

Each $R_{3b}$ is independently selected from hydrogen, $(C_1-C_{10})$ alkyl, aryl or aryl$(C_1-C_3)$alkyl, each optionally substituted with halogen (e.g., fluorine, chlorine, bromine, iodine), $(C_1-C_3)$alkoxy, $(C_1-C_3)$alkyl, halo$(C_1-C_3)$alkyl, halo$(C_1-C_3)$alkoxy, cyano or nitro; and Each $R_{4b}$ is independently selected from hydrogen, halogen (e.g., fluorine, chlorine, bromine, iodine), $(C_1-C_{10})$alkyl, $(C_1-C_{10})$alkoxy, aryl, aryl$(C_1-C_3)$alkyl, cycloalkyl or aryl $(C_1-C_3)$alkoxy, each optionally substituted with halogen (e.g., fluorine, chlorine, bromine, iodine), $(C_1-C_3)$alkoxy, $(C_1-C_3)$alkyl, halo$(C_1-C_3)$alkyl, halo$(C_1-C_3)$alkoxy, cyano or nitro; and $R_{5b}$ is hydrogen or $C(=O)O(C_1-C_3)$alkyl, the method comprising:
aminating a compound represented by Formula X:

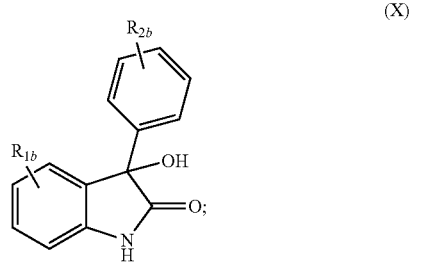

(X)

with tert-butyldimethylsilyl amine (TBDMSNH$_2$) in the presence of SnCl$_4$ and an agent selected from the group comprising triethylamine, N-ethyldiisopropylamine or N-methyl morpholine (NMM), thereby forming the compound represented by Formula VII.

A representative scheme for such a method is described herein in Example 8, Scheme 20.

In an additional embodiment, the invention relates to a method of preparing a compound represented by Formula XVII:

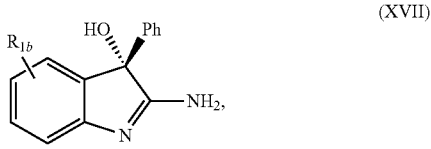

(XVII)

wherein the method comprises:
aminating a compound represented by Formula XXI:

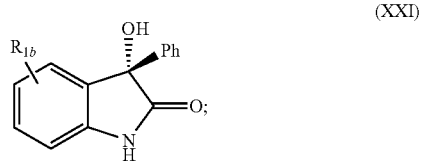

(XXI)

with tert-butyldimethylsilyl amine (TBDMSNH$_2$) in the presence of SnCl$_4$ and an agent selected from triethylamine, N-ethyldiisopropylamine or N-methyl morpholine (NMM), thereby forming the compound represented by Formula XVII.

In a particular embodiment, the amination step in the synthetic methods described herein is performed at a temperature of about 120° C. (e.g., in a microwave) for about 40 to about 60 minutes in the presence of tetrahydrofuran (THF).

As an alternative to the enantioselective amination step described herein, chiral separation techniques and/or methods can be employed to prepare enantiomers of 2-aminoindole compounds. Suitable chiral separation techniques and methods include, for example, various well-known chiral chromatography techniques and separation methods. An appropriate technique and/or method of separating enantiomers from a racemic mixture of a 2-aminoindole compound disclosed herein can be readily determined by those of skill in the art.

A representative scheme for such a method is described herein in Example 10, Scheme 22.

In addition to the methods described above, supercritical fluid chromatography techniques and/or methods can be employed to prepare enantiomers of 2-aminoindole compounds, as described in Example 18.

In another embodiment, the present invention is a method of preparing a compound represented by Formula VII:

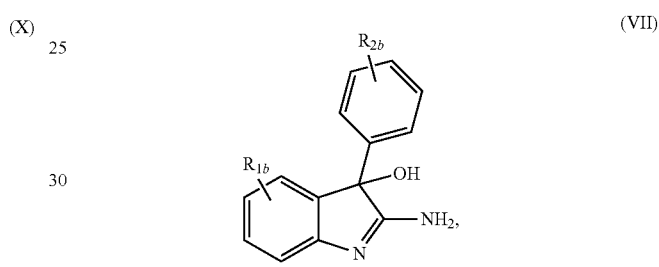

(VII)

or a pharmaceutically acceptable salt thereof,
wherein
Each $R_{1b}$ is independently selected from hydrogen, halogen (e.g., fluorine, chlorine, bromine, iodine), nitro, cyano, hydroxy, $(C_1-C_6)$alkyl, $(C_1-C_6)$alkenyl, $(C_1-C_6)$alkynyl, $(C_1-C_6)$alkoxy, aryl, heteroaryl, cycloalkyl, heterocyclyl, aryl$(C_1-C_3)$alkyl, heteroaryl$(C_1-C_3)$alkyl, cycloalkyl$(C_1-C_3)$alkyl, heterocyclyl$(C_1-C_3)$alkyl, hydroxy$(C_1-C_3)$alkyl, $N(R_{3b})_2$, $C(=NOH)NH_2$, $NR_3CON(R_{3b})_2$, $CON(R_{3b})_2$, $CO_2R_{3b}$, $COR_{4b}$, $OC(O)R_{3b}$, $SO_2N(R_{3b})_2$, $SO_2R_{4b}$, $NR_3COR_{4b}$, $NR_3CO_2R_{4b}$, $NR_3SO_2R_{4b}$ and $OC(=O)N(R_3)_2$, each optionally substituted with one or more groups represented by $R_{2b}$;

Each $R_{2b}$ is independently selected from halogen (e.g., fluorine, chlorine, bromine, iodine), nitro, cyano, hydroxy, $(C_1-C_4)$alkyl, halo$(C_1-C_3)$alkyl, hydroxy$(C_1-C_4)$alkyl, $(C_1-C_4)$alkoxy, halo$(C_1-C_4)$alkoxy, aryl, haloaryl, cycloalkyl, aryl$(C_1-C_3)$alkyl, aryl$(C_1-C_4)$alkoxy, heterocyclyl, $N(R_{3b})_2$, $C(=NOH)NH_2$, $NR_{3b}CON(R_{3b})_2$, $CON(R_{3b})_2$, $CO_2R_{3b}$, $COR_{4b}$, $OC(O)R_{3b}$, S, $SO_2N(R_{3b})_2$, $SO_2R_{4b}$, $SR_{4b}$, $S(C_1-C_3)$alkylcycloalkyl, $NR_{3b}COR_{4b}$, $NR_{3b}CO_2R_{4b}$, $NR_3SO_2R_4$, $S(=O)R_{3b}$, —O-cycloalkyl, —O-heterocyclyl, adamantyl, $OC(=O)N(R_{3b})_2$,

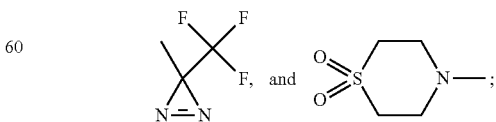

Each $R_{3b}$ is independently selected from hydrogen, $(C_1-C_{10})$ alkyl, aryl or aryl$(C_1-C_3)$alkyl, each optionally substituted with halogen (e.g., fluorine, chlorine, bromine, iodine), ($C_1$-$C_3$)alkoxy, ($C_1$-$C_3$)alkyl, halo($C_1$-$C_3$)alkyl, halo($C_1$-$C_3$)alkoxy, cyano or nitro; and Each $R_{4b}$ is independently selected from hydrogen, halogen (e.g., fluorine, chlorine, bromine, iodine), ($C_1$-$C_{10}$)alkyl, ($C_1$-$C_{10}$)alkoxy, aryl, aryl($C_1$-$C_3$)alkyl, cycloalkyl or aryl ($C_1$-$C_3$)alkoxy, each optionally substituted with halogen (e.g., fluorine, chlorine, bromine, iodine), ($C_1$-$C_3$)alkoxy, ($C_1$-$C_3$)alkyl, halo($C_1$-$C_3$)alkyl, halo($C_1$-$C_3$)alkoxy, cyano or nitro, comprising:

a) reacting a compound represented by Formula VIII:

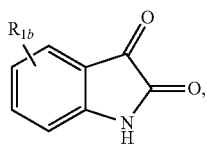

(VIII)

with an agent represented by Formula IX:

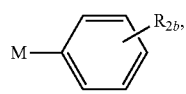

(IX)

wherein M is MgBr, Li or B(OH)$_2$,
thereby forming a compound represented by Formula X:

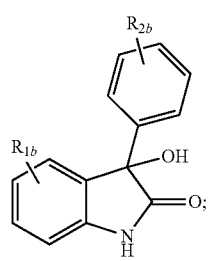

(X)

and b) aminating the compound of Formula X with tert-butyldimethylsilyl amine (TBDMSNH$_2$) in the presence of SnCl$_4$ and an agent selected from triethylamine, N-ethyldiisopropylamine or N-methyl morpholine (NMM), thereby forming the compound represented by Formula VII.

A representative scheme for such a method is described herein in Example 8, Scheme 20.

In another embodiment, the instant invention is a method of preparing a compound represented by Formula XI:

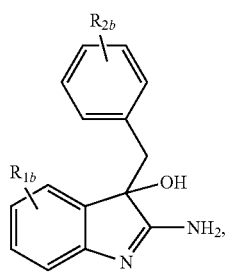

(XI)

or a pharmaceutically acceptable salt thereof,
wherein

Each $R_{1b}$ is independently selected from hydrogen, halogen (e.g., fluorine, chlorine, bromine, iodine), nitro, cyano, hydroxy, ($C_1$-$C_6$)alkyl, ($C_1$-$C_6$)alkenyl, ($C_1$-$C_6$)alkynyl, ($C_1$-$C_6$)alkoxy, aryl, heteroaryl, cycloalkyl, heterocyclyl, aryl($C_1$-$C_3$)alkyl, heteroaryl($C_1$-$C_3$)alkyl, cycloalkyl($C_1$-$C_3$)alkyl, heterocyclyl($C_1$-$C_3$)alkyl, hydroxy($C_1$-$C_3$)alkyl, N($R_{3b}$)$_2$, C(=NOH)NH$_2$, NR$_{3b}$CON(R$_{3b}$)$_2$, CON(R$_{3b}$)$_2$, CO$_2$R$_{3b}$, COR$_{4b}$, OC(O)R$_{3b}$, SO$_2$N(R$_{3b}$)$_2$, SO$_2$R$_{4b}$, NR$_{3b}$COR$_{4b}$, NR$_3$CO$_2$R$_{4b}$, NR$_3$SO$_2$R$_{4b}$ and OC(=O)N(R$_{3b}$)$_2$, each optionally substituted with one or more groups represented by R$_{2b}$;

Each R$_{2b}$ is independently selected from halogen (e.g., fluorine, chlorine, bromine, iodine), nitro, cyano, hydroxy, ($C_1$-$C_4$)alkyl, halo($C_1$-$C_4$)alkyl, hydroxy($C_1$-$C_4$)alkyl, ($C_1$-$C_4$)alkoxy, halo($C_1$-$C_4$)alkoxy, aryl, haloaryl, cycloalkyl, aryl($C_1$-$C_3$)alkyl, aryl($C_1$-$C_4$)alkoxy, heterocyclyl, N(R$_{3b}$)$_2$, C(=NOH)NH$_2$, NR$_{3b}$CON(R$_{3b}$)$_2$, CON(R$_{3b}$)$_2$, CO$_2$R$_{3b}$, COR$_{4b}$, OC(O)R$_{3b}$, S, SO$_2$N(R$_{3b}$)$_2$, SO$_2$R$_{4b}$, SR$_{4b}$, S(C$_1$-$C_3$)alkylcycloalkyl, NR$_{3b}$COR$_{4b}$, NR$_{3b}$CO$_2$R$_{4b}$, NR$_{3b}$SO$_2$R$_{4b}$, S(=O)R$_{3b}$, —O-cycloalkyl, —O-heterocyclyl, adamantyl, OC(=O)N(R$_{3b}$)$_2$,

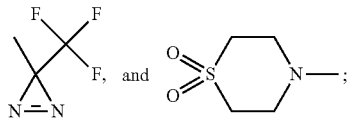

Each R$_{3b}$ is independently selected from hydrogen, ($C_1$-$C_{10}$)alkyl, aryl or aryl($C_1$-$C_3$)alkyl, each optionally substituted with halogen (e.g., fluorine, chlorine, bromine, iodine), ($C_1$-$C_3$)alkoxy, ($C_1$-$C_3$)alkyl, halo($C_1$-$C_3$)alkyl, halo($C_1$-$C_3$)alkoxy, cyano or nitro; and Each R$_{1b}$ is independently selected from hydrogen, halogen (e.g., fluorine, chlorine, bromine, iodine), ($C_1$-$C_{10}$)alkyl, ($C_1$-$C_{10}$)alkoxy, aryl, aryl($C_1$-$C_3$)alkyl, cycloalkyl or aryl ($C_1$-$C_3$)alkoxy, each optionally substituted with halogen (e.g., fluorine, chlorine, bromine, iodine), ($C_1$-$C_3$)alkoxy, ($C_1$-$C_3$)alkyl, halo($C_1$-$C_3$)alkyl, halo($C_1$-$C_3$)alkoxy, cyano or nitro, comprising:

a) reacting a compound represented by Formula XII:

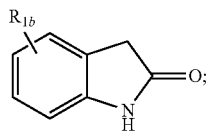

(XII)

with an agent represented by Formula XIII:

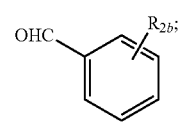

(XIII)

thereby forming a compound represented by Formula XIV:

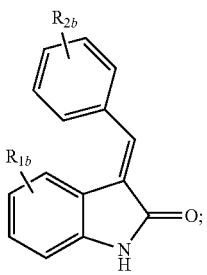

(XIV)

and b) reacting the compound of Formula XIV with H$_2$ in the presence of Pd/C and, optionally, Ph$_2$S, thereby forming the compound represented by Formula XV:

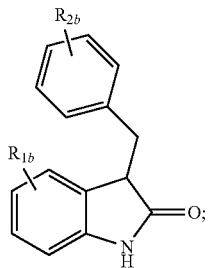
(XV)

and c) oxidizing the compound of Formula XV with potassium peroxymonosulfate (OXONE), thereby forming the compound represented by Formula XVI:

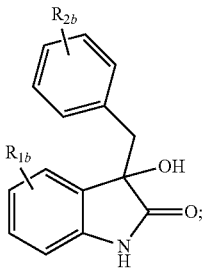
(XVI)

and d) aminating the compound of Formula XVI with tert-butyldimethylsilyl amine (TBDMSNH$_2$) in the presence of SnCl$_4$ and an agent selected from triethylamine, N-ethyldiisopropylamine or N-methyl morpholine (NMM), thereby forming the compound represented by Formula XI.

A representative scheme for such a method is described herein in Example 9, Scheme 21.

In another embodiment, the instant invention is a method of preparing a compound represented by Formula XVII:

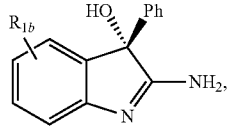
(XVII)

or a pharmaceutically acceptable salt thereof,
wherein

Each R$_{1b}$ is independently selected from hydrogen, halogen (e.g., fluorine, chlorine, bromine, iodine), nitro, cyano, hydroxy, (C$_1$-C$_6$)alkyl, (C$_1$-C$_6$)alkenyl, (C$_1$-C$_6$)alkynyl, (C$_1$-C$_6$)alkoxy, aryl, heteroaryl, cycloalkyl, heterocyclyl, aryl(C$_1$-C$_3$)alkyl, heteroaryl(C$_1$-C$_3$)alkyl, cycloalkyl(C$_1$-C$_3$)alkyl, heterocyclyl(C$_1$-C$_3$)alkyl, hydroxy(C$_1$-C$_3$)alkyl, N(R$_{3b}$)$_2$, C(=NOH)NH$_2$, NR$_{3b}$CON(R$_{3b}$)$_2$, CON(R$_{3b}$)$_2$, CO$_2$R$_{3b}$, COR$_{4b}$, OC(O)R$_3$, SO$_2$N(R$_{3b}$)$_2$, SO$_2$R$_{4b}$, NR$_3$COR$_4$, NR$_{3b}$CO$_2$R$_{4b}$, NR$_{3b}$SO$_2$R$_{4b}$ and OC(=O)N(R$_{3b}$)$_2$, each optionally substituted with one or more groups represented by R$_{2b}$;

Each R$_{2b}$ is independently selected from halogen (e.g., fluorine, chlorine, bromine, iodine), nitro, cyano, hydroxy, (C$_1$-C$_4$)alkyl, halo(C$_1$-C$_3$)alkyl, hydroxy(C$_1$-C$_4$)alkyl, (C$_1$-C$_4$)alkoxy, halo(C$_1$-C$_4$)alkoxy, aryl, haloaryl, cycloalkyl, aryl(C$_1$-C$_3$)alkyl, aryl(C$_1$-C$_4$)alkoxy, hetero-cyclyl, N(R$_{3b}$)$_2$, C(=NOH)NH$_2$, NR$_{3b}$CON(R$_{3b}$)$_2$, CON(R$_{3b}$)$_2$, CO$_2$R$_{3b}$, COR$_{4b}$, OC(O)R$_{3b}$, S, SO$_2$N(R$_{3b}$)$_2$, SO$_2$R$_{4b}$, SR$_{4b}$, S(C$_1$-C$_3$)alkylcycloalkyl, NR$_{3b}$COR$_{4b}$, NR$_{3b}$CO$_2$R$_{4b}$, NR$_{3b}$SO$_2$R$_{4b}$, S(=O)R$_{3b}$, —O-cycloalkyl, —O-heterocyclyl, adamantyl, OC(=O)N(R$_3$)$_2$,

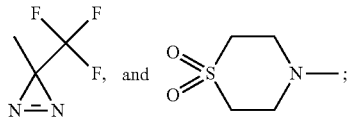

Each R$_{3b}$ is independently selected from hydrogen, (C$_1$-C$_{10}$)alkyl, aryl or aryl(C$_1$-C$_3$)alkyl, each optionally substituted with halogen (e.g., fluorine, chlorine, bromine, iodine), (C$_1$-C$_3$)alkoxy, (C$_1$-C$_3$)alkyl, halo(C$_1$-C$_3$)alkyl, halo(C$_1$-C$_3$)alkoxy, cyano or nitro; and Each R$_{4b}$ is independently selected from hydrogen, halogen (e.g., fluorine, chlorine, bromine, iodine), (C$_1$-C$_{10}$)alkyl, (C$_1$-C$_{10}$)alkoxy, aryl, aryl(C$_1$-C$_3$)alkyl, cycloalkyl or aryl (C$_1$-C$_3$)alkoxy, each optionally substituted with halogen (e.g., fluorine, chlorine, bromine, iodine), (C$_1$-C$_3$)alkoxy, (C$_1$-C$_3$)alkyl, halo(C$_1$-C$_3$)alkyl, halo(C$_1$-C$_3$)alkoxy, cyano or nitro, comprising:

a) reducing a compound represented by Formula XVIII:

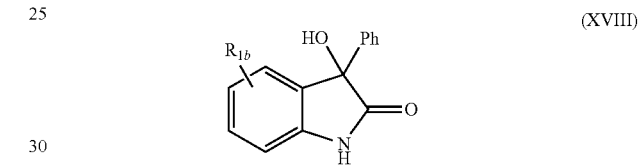
(XVIII)

with triethylsilane (Et$_3$SiH) and trifluoroacetic acid (TFA), thereby forming a compound represented by Formula XIX:

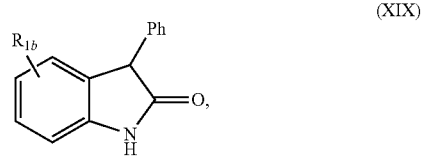
(XIX)

and b) oxidizing the compound of Formula XIX with an agent represented by Formula XX:

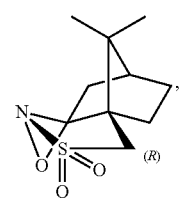
(XX)

in the presence of potassium hexamethyldisilazane (KHMDS) and tetrahydrofuran (THF), thereby forming the compound represented by Formula XXI:

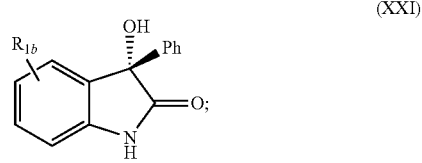
(XXI)

and c) aminating the compound of Formula XXI with tert-butyldimethylsilyl amine (TBDMSNH$_2$) in the presence of SnCl$_4$ and an agent selected from the group comprising triethylamine, N-ethyldiisopropylamine and an agent selected from the group comprising triethylamine, N-ethyldiisopropylamine and N-methyl morpholine (NMM), thereby forming the compound represented by Formula (XVII).

A representative scheme for such a method is described herein in Example 10, Scheme 22.

Values and alternative values for the variables in Structural Formula VI-XXI are provided in the following paragraphs:

$R_{1b}$ is hydrogen, halogen (e.g., fluorine, chlorine, bromine, iodine), nitro, cyano, hydroxy, (C$_1$-C$_6$)alkyl, (C$_1$-C$_6$)alkenyl, (C$_1$-C$_6$)alkynyl, (C$_1$-C$_6$)alkoxy, aryl, heteroaryl, cycloalkyl, heterocyclyl, aryl(C$_1$-C$_3$)alkyl, heteroaryl(C$_1$-C$_3$)alkyl, cycloalkyl(C$_1$-C$_3$)alkyl, heterocyclyl(C$_1$-C$_3$)alkyl, hydroxy (C$_1$-C$_3$)alkyl, N(R$_{3b}$)$_2$, C(=NOH)NH$_2$, NR$_3$CON(R$_{3b}$)$_2$, CON(R$_{3b}$)$_2$, CO$_2$R$_{3b}$, COR$_{4b}$, OC(O)R$_{3b}$, SO$_2$N(R$_{3b}$)$_2$, SO$_2$R$_{4b}$, NR$_3$COR$_{4b}$, NR$_{3b}$CO$_2$R$_{4b}$, NR$_{3b}$SO$_2$R$_{4b}$ and OC(=O)N(R$_{3b}$)$_2$, each optionally substituted with one or more groups represented by $R_{2b}$. Alternatively, $R_{1b}$ is halogen (e.g., fluorine, chlorine, bromine, iodine), (C$_1$-C$_6$)alkyl or (C1-C6)alkoxy. Alternatively, $R_{1b}$ is halogen. Alternatively, $R_{1b}$ is chlorine. Alternatively, $R_{1b}$ is methyl. Alternatively, $R_{1b}$ is methoxy.

Each $R_{2b}$ is independently selected from halogen (e.g., fluorine, chlorine, bromine, iodine), nitro, cyano, hydroxy, (C$_1$-C$_4$)alkyl, halo(C$_1$-C$_3$)alkyl, hydroxy(C$_1$-C$_4$)alkyl, (C$_1$-C$_4$)alkoxy, halo(C$_1$-C$_4$)alkoxy, aryl, haloaryl, cycloalkyl, aryl(C$_1$-C$_3$)alkyl, aryl(C$_1$-C$_4$)alkoxy, heterocyclyl, N(R$_{3b}$)$_2$, C(=NOH)NH$_2$, NR$_{3b}$CON(R$_{3b}$)$_2$, CON(R$_{3b}$)$_2$, CO$_2$R$_{3b}$, COR$_{4b}$, OC(O)R$_{3b}$, S, SO$_2$N(R$_{3b}$)$_2$, SO$_2$R$_{4b}$, SR$_{4b}$, S(C$_1$-C$_3$) alkylcycloalkyl, NR$_{3b}$COR$_{4b}$, NR$_{3b}$CO$_2$R$_{4b}$, NR$_{3a}$SO$_2$R$_{4a}$, S(=O)R$_{3b}$, —O-cycloalkyl, —O-heterocyclyl, adamantyl, OC(=O)N(R$_{3b}$)$_2$,

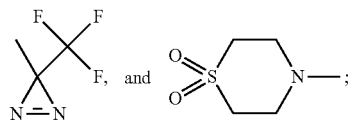

Each $R_{3b}$ is independently selected from hydrogen, (C$_1$-C$_{10}$)alkyl, aryl or aryl(C$_1$-C$_3$)alkyl, each optionally substituted with halogen (e.g., fluorine, chlorine, bromine, iodine), (C$_1$-C$_3$)alkoxy, (C$_1$-C$_3$)alkyl, halo(C$_1$-C$_3$)alkyl, halo(C$_1$-C$_3$) alkoxy, cyano or nitro; and Each $R_{4b}$ is independently selected from hydrogen, halogen (e.g., fluorine, chlorine, bromine, iodine), (C$_1$-C$_{10}$)alkyl, (C$_1$-C$_{10}$)alkoxy, aryl, aryl(C$_1$-C$_3$)alkyl, cycloalkyl or aryl (C$_1$-C$_3$)alkoxy, each optionally substituted with halogen (e.g., fluorine, chlorine, bromine, iodine), (C$_1$-C$_3$)alkoxy, (C$_1$-C$_3$)alkyl, halo(C$_1$-C$_3$)alkyl, halo(C$_1$-C$_3$)alkoxy, cyano or nitro.

DEFINITIONS

The term "alkyl", used alone or as part of a larger moiety such as "arylalkyl" or "haloalkyl" means a straight or branched hydrocarbon radical having 1-10 carbon atoms and includes, for example, methyl, ethyl, n-propyl, isopropyl, n-butyl, sec-butyl, isobutyl, tert-butyl, n-pentyl, i-pentyl, n-hexyl, n-heptyl, n-octyl, n-nonyl, n-decyl and the like.

An "alkenyl group" is an alkyl group in which at least a pair of adjacent methylenes are replaced with —CH=CH—.

An "alkynyl group" is an alkyl group in which at least a pair of adjacent methylenes are replaced with —C≡C—.

The term "cycloalkyl", used alone or as part of a larger moiety, means a monocyclic, bicyclic or tricyclic, saturated hydrocarbon ring having 3-10 carbon atoms and includes, for example, cyclopropyl, cyclobutyl, cyclopentyl, cyclohexyl, cycloheptyl, cyclooctyl, bicyclo[2.2.2]octyl, bicyclo[2.2.1] heptyl, Spiro[4.4]nonane, adamantyl and the like. Unless otherwise described, exemplary substituents for a substituted cycloalkyl group include groups represented by $R^6$.

"Aryl", used alone or as part of a larger moiety as in "arylalkyl", "arylalkoxy", or "aryloxyalkyl", means a 6-14 membered carbocyclic aromatic monocyclic or polycyclic ring system. Examples include phenyl, naphthyl, anthracenyl, 1,2-dihydronaphthyl, 1,2,3,4-tetrahydronaphthyl, fluorenyl, indanyl, indenyl and the like. The term "aryl" also includes phenyl rings fused to a non-aromatic carbocyclic ring, a heterocyclyl group or to a heteroaryl group, wherein the connection to an indole ring from structural Formula (I) is through the phenyl ring of the fused ring system and includes, for example dibenzo[b,d]furyl, quinoline, or the like. The term "aryl" may be used interchangeably with the terms "aromatic group", "aryl ring" "aromatic ring", "aryl group" and "aromatic group". Unless otherwise described, exemplary substituents for a substituted aryl group include groups represented by $R^6$.

"Hetero" refers to the replacement of at least one carbon atom member in a ring system with at least one heteroatom selected from N, S, and O. A hetero ring may have 1, 2, 3, or 4 carbon atom members replaced by a heteroatom.

"Heteroaryl", used alone or as part of a larger moiety as in "heteroarylalkyl" or "heteroarylalkoxy", means a 5-10 membered monovalent heteroaromatic monocyclic and polycyclic ring radical containing 1 to 4 heteroatoms independently selected from N, O, and S. The term "heteroaryl" also includes monocyclic heteroaryl ring fused to non-aromatic carbocyclic ring, to a heterocyclyl group or to an aryl ring, wherein the connection to a indole ring of structural Formula (I) is through the monocyclic heteroaryl ring of the fused ring system. Heteroaryl groups include, but are not limited to, furyl, thienyl, thiophenyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridinyl-N-oxide, pyridazinyl, pyrimidinyl, pyrazinyl, indolizinyl, indolyl, isoindolyl, imidazo[4,5-b]pyridine, benzo[b]furyl, benzo[b]thienyl, indazolyl, benzimidazolyl, benzthiazolyl, purinyl, 4H-quinolizinyl, quinolinyl, isoquinolinyl, quinazolinyl, benzothienyl, benzofuranyl, 2,3-dihydrobenzofuranyl, benzodioxolyl, benzimidazolyl, indazolyl, benzisoxazolyl, benzoxazolyl, benzothiazolyl, cinnolinyl, phthalzinyl, quinazolinyl, quinoxalinyl, 1,8-naphthyridinyl, 1,2,3-triazolyl, 1,2,4-triazolyl, 1,3,4-oxadiazolyl, 1,2,5-thiadiazolyl, 1,2,5-thiadiazolyl-1-oxide, 1,2,5-thiadiazolyl-1,1-dioxide, 1,3,4-thiadiazolyl, 1,2,4-triazinyl, 1,3,5-triazinyl, tetrazolyl, and pteridinyl. The terms "heteroaryl", "heteroaromatic", "heteroaryl ring", "heteroaryl group" and "heteroaromatic group" are used interchangeably herein. "Heteroarylalkyl" means alkyl substituted with heteroaryl; and "heteroarylalkoxy" means alkoxy substituted with heteroaryl. Unless otherwise described, exemplary substituents for a substituted heteroaryl group include the include groups represented by $R^6$.

The term "heterocyclyl" means a 4-, 5-, 6- and 7-membered saturated or partially unsaturated heterocyclic ring containing 1 to 4 heteroatoms independently selected from N, O, and S. Exemplary heterocyclyls include azetidine, pyrrolidine, pyrrolidin-2-one, 1-methylpyrrolidin-2-one, piperidine, piperidin-2-one, 2-pyridone, 4-pyridone, piperazine, 1-(2,2,2-trifluoroethyl)piperazine, piperazin-2-one, 5,6-dihydropyrimidin-4-one, pyrimidin-4-one, tetrahydrofuran, tetrahydropyran, tetrahydrothiophene, tetrahydrothiopyran, isoxazolidine, 1,3-dioxolane, 1,3-dithiolane, 1,3-dioxane, 1,4-dioxane, 1,3-dithiane, 1,4-dithiane, oxazolidin-2-one, imidazolidin-2-one, imidazolidine-2,4-dione, tetrahydropyrimidin-2(1H)-one, morpholine, N-methylmorpholine, morpholin-3-one, 1,3-oxazinan-2-one, thiomorpholine, thiomorpholine 1,1-dioxide, tetrahydro-1,2,5-thiaoxazole 1,1-dioxide, tetrahydro-2H-1,2-thiazine 1,1-dioxide, hexahydro-1,2,6-thiadiazine 1,1-dioxide, tetrahydro-1,2,5-thiadiazole 1,1-dioxide and isothiazolidine 1,1-dioxide. Unless otherwise described, exemplary substituents for a substituted heterocyclyl group include groups represented by $R^6$.

The term "alkoxy" means an alkyl radical attached through an oxygen linking atom. "$(C_1-C_4)$-alkoxy" includes methoxy, ethoxy, propoxy, and butoxy.

The term "cycloalkoxy" means a cycloalkyl radical attached through an oxygen linking atom. "$(C_3-C_6)$cycloalkoxy" includes cyclopropyloxy, cyclobutyloxy, cyclopentyloxy and cyclohexyloxy.

The term "aryloxy" means an aryl moiety attached through an oxygen linking atom. Aryloxy includes, but not limited to, phenoxy.

The terms "halogen" and "halo" are interchangeably used herein and each refers to fluorine, chlorine, bromine, or iodine.

As used herein the terms "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

Malaria is a parasitic infection of red blood cells caused by eukaryotic protists of the genus *Plasmodium* in the phylum Apicomplexa. Human malaria is known to be caused by five different *Plasmodium* species: *Plasmodium falciparum, Plasmodium vivax, Plasmodium ovale, Plasmodium malariae* or *Plasmodium knowlesi*. Malaria parasites are transmitted by female *Anopheles* mosquitoes. The parasites multiply within red blood cells, causing symptoms that include symptoms of anemia (light headedness, shortness of breath, tachycardia), as well as other general symptoms such as an enlarged spleen, fatigue, fever, chills, nausea, flu-like illness, and in severe cases, coma and death. The methods described herein are useful for treating human malaria caused by a *Plasmodium* species, such as *Plasmodium falciparum, Plasmodium vivax, Plasmodium ovale, Plasmodium malariae* or *Plasmodium knowlesi*. In a particular embodiment, the invention relates to a method of treating a malaria caused by *Plasmodium falciparum*. Both drug-resistant and drug-sensitive strains of *Plasmodium* are intended to be included herein.

Certain of the disclosed compounds may exist in various stereoisomeric forms. Stereoisomers are compounds that differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms. The symbol "*" in a structural formula represents the presence of a chiral carbon center. "R" and "S" represent the configuration of substituents around one or more chiral carbon atoms. Thus, "R*" and "S*" denote the relative configurations of substituents around one or more chiral carbon atoms. Enantiomers of a compound can be prepared, for example, by separating an enantiomer from a racemate using one or more well-known techniques and methods, such as, for example, chiral chromatography and separation methods based thereon. The appropriate technique and/or method for separating an enantiomer of a compound described herein from a racemic mixture can be readily determined by those of skill in the art.

"Racemate" or "racemic mixture" means a compound containing two enantiomers, wherein such mixtures exhibit no optical activity; i.e., they do not rotate the plane of polarized light.

"Geometric isomer" means isomers that differ in the orientation of substituent atoms in relationship to a carbon-carbon double bond, to a cycloalkyl ring, or to a bridged bicyclic system. Atoms (other than H) on each side of a carbon-carbon double bond may be in an E (substituents are on opposite sides of the carbon-carbon double bond) or Z (substituents are oriented on the same side) configuration.

"R," "S," "S*," "R*," "E," "Z," "cis," and "trans," indicate configurations relative to the core molecule.

Certain of the disclosed compounds may exist in various tautomeric forms. Tautomeric forms exist when a compound is a mixture of two or more structurally distinct compounds that are in rapid equilibrium. Certain compounds of the invention exist as tautomeric forms. For example, the following compound represented by Structural Formula (A) and (B) include at least the following tautomers forms:

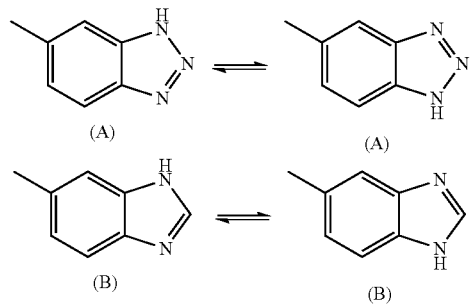

It is to be understood that when one tautomeric form of a compound is depicted by name or structure, all tautomeric forms of the compound are included.

Certain of the disclosed compounds may exist in atropisomeric forms. Atropisomers are stereoisomers resulting from hindered rotation about single bonds where the steric strain barrier to rotation is high enough to allow for the isolation of the conformers.

The compounds of the invention may be prepared as individual isomers by either isomer-specific synthesis or resolved from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods.

When the stereochemistry of a disclosed compound is named or depicted by structure, the named or depicted stereoisomer is at least 60%, 70%, 80%, 90%, 99% or 99.9% by weight relative to the other stereoisomers. When a single enantiomer is named or depicted by structure, the depicted or named enantiomer is at least 60%, 70%, 80%, 90%, 99% or 99.9% by weight optically pure. Percent optical purity by weight is the ratio of the weight of the enantiomer over the weight of the enantiomer plus the weight of its optical isomer.

When a disclosed compound is named or depicted by structure without indicating the stereochemistry, and the compound has at least one chiral center, it is to be understood that the name or structure encompasses either enantiomer of the compound free from the corresponding optical isomer, a racemic mixture of the compound and mixtures enriched in one enantiomer relative to its corresponding optical isomer.

When a disclosed compound is named or depicted by structure without indicating the stereochemistry and has at least two chiral centers, it is to be understood that the name or structure encompasses a diastereomer free of other diastereomers, a pair of diastereomers free from other diastereomeric pairs, mixtures of diastereomers, mixtures of diastereomeric pairs, mixtures of diastereomers in which one diastereomer is enriched relative to the other diastereomer(s) and mixtures of diastereomeric pairs in which one diastereomeric pair is enriched relative to the other diastereomeric pair(s).

As used herein, "substantially pure" means that the depicted or named compound is at least about 60% by weight. For example, "substantially pure" can mean about 60%, 70%, 72%, 75%, 77%, 80%, 82%, 85%, 86%, 87%, 88%, 89%, 90%, 91%, 92%, 93%, 94%, 95%, 96%, 97%, 98%, 99%, 99.5%, 99.9%, or a percentage between 70% and 100%. In one embodiment, substantially pure means that the depicted or named compound is at least about 75%. In a specific embodiment, substantially pure means that the depicted or named compound is at least about 90% by weight.

EXEMPLIFICATION

Example 1

Synthesis of 2-aminoindoles via 2-aminobenzophenone intermediates, benzamide route

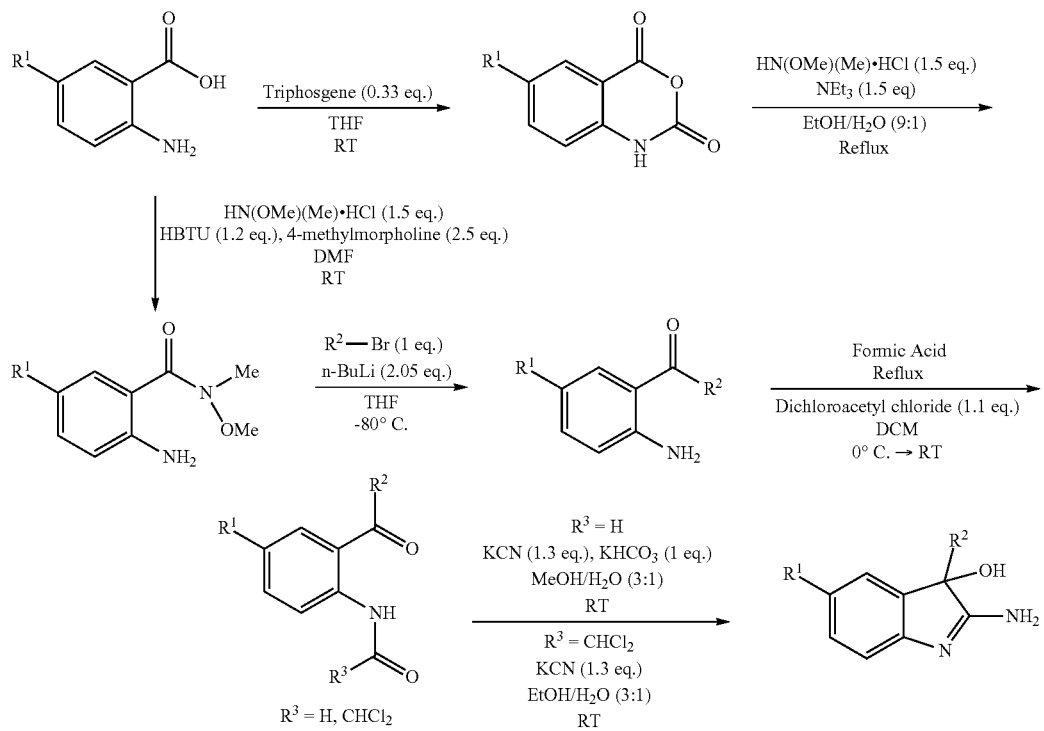

All solvents for reactions, extractions, and chromatography were of analytical grade. Dichloromethane, N,N-dimethylformamide, methanol, and tetrahydrofuran were passed through an alumina column (A-2) and supported copper redox catalyst (Q-5 reactant). All other solvents, except for ethanol (Pharmco-Aaper), were obtained from Aldrich. Solvents were used without further purification, except where noted.

Reaction vessels were oven-dried for at least 12 hours, and reactions took place in either argon or nitrogen atmospheres. All reactions were magnetically stirred.

Reactions were monitored by thin layer chromatography (TLC) using silica gel 60 plates, treated with 254 nm-fluorescent dye (EMD) and by LC-MS (Waters 2690 Separations Module with Waters Micromass LCT or Waters 2795 Separations Module with Waters Micromass ZQ). Stated mass spectrometry data are from LC-MS analysis.

Evaporation of solvent was conducted by rotary evaporation. For column chromatography purification, silica gel 60, 230-400 mesh was used (EMD). Flash purification systems were also used with associated pre-packaged silica columns (Biotage Isolera and Teledyne Isco Companion).

$^1$H NMR spectra were recorded at 300 or 500 MHz on Bruker 300 and Varian I-500 NMR spectrometers, respectively. $^{13}$C NMR spectra were recorded at 126 MHz using a Varian I-500 NMR spectrometer. Chemical shifts in CDCl$_3$, CD$_3$OD, CD$_3$CN, and (CD$_3$)$_2$O are reported in ppm, relative to CHCl$_3$ ($^1$H NMR, δ=7.24 ppm; $^{13}$C NMR, δ=77.23 ppm), CH$_3$OH ($^1$H NMR, δ=4.87 ppm, 3.31 ppm; $^{13}$C NMR, δ=49.15 ppm), CH$_3$CN ($^1$H NMR, δ=1.94), and (CH$_3$)$_2$O ($^1$H NMR, δ=2.05). Coupling constants are given in hertz. Attempts were made to be consistent in the NMR solvent; however, varying solubilities of compounds demanded the use of different solvents. Suitable solvents can be ascertained by those of skill in the art.

Example 2

Synthesis of 2-aminoindoles by Coupling of Aldehyde Starting Materials

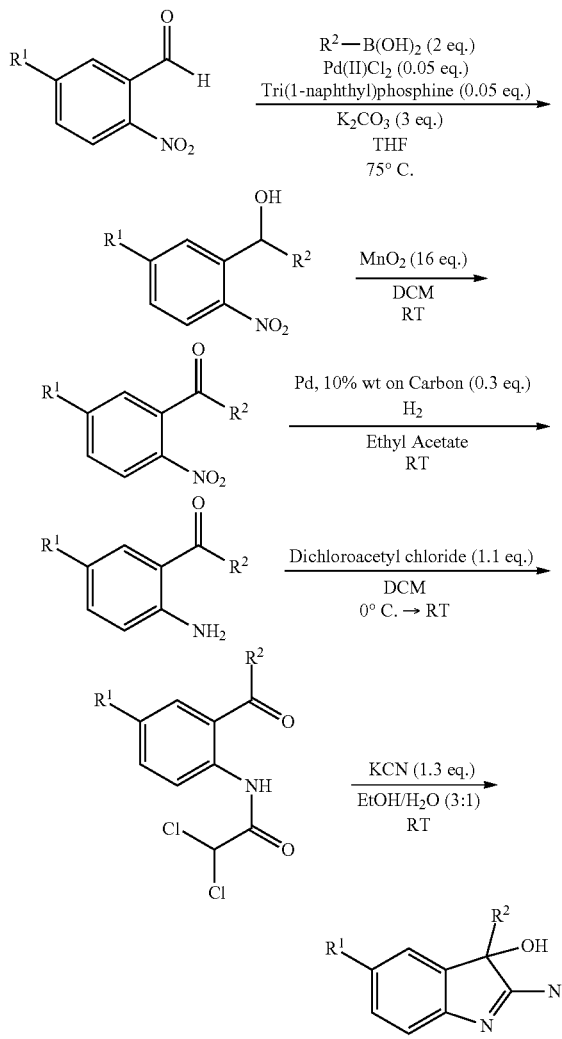

All solvents for reactions, extractions, and chromatography were of analytical grade. Dichloromethane, N,N-dimethylformamide, methanol, and tetrahydrofuran were passed through an alumina column (A-2) and supported copper redox catalyst (Q-5 reactant). All other solvents, except for ethanol (Pharmco-Aaper), were obtained from Aldrich. Solvents were used without further purification, except where noted.

Reaction vessels were oven-dried for at least 12 hours, and reactions took place in either argon or nitrogen atmospheres. All reactions were magnetically stirred.

Reactions were monitored by thin layer chromatography (TLC) using silica gel 60 plates, treated with 254 nm-fluorescent dye (EMD) and by LC-MS (Waters 2690 Separations Module with Waters Micromass LCT or Waters 2795 Separations Module with Waters Micromass ZQ). Stated mass spectrometry data are from LC-MS analysis.

Evaporation of solvent was conducted by rotary evaporation. For column chromatography purification, silica gel 60, 230-400 mesh was used (EMD). Flash, purification systems were also used with associated pre-packaged silica columns (Biotage Isolera and Teledyne Isco Companion).

$^1$H NMR spectra were recorded at 300 or 500 MHz on Bruker 300 and Varian I-500 NMR spectrometers, respectively. $^{13}$C NMR spectra were recorded at 126 MHz using a Varian I-500 NMR spectrometer. Chemical shifts in CDCl$_3$, CD$_3$OD, CD$_3$CN, and (CD$_3$)$_2$O are reported in ppm, relative to CHCl$_3$ ($^1$H NMR, δ=7.24 ppm; $^{13}$C NMR, δ=77.23 ppm), CH$_3$OH ($^1$H NMR, δ=4.87 ppm, 3.31 ppm; $^{13}$C NMR, δ=49.15 ppm), CH$_3$CN ($^1$H NMR, δ=1.94), and (CH$_3$)$_2$O ($^1$H NMR, δ=2.05). Coupling constants are given in hertz. Attempts were made to be consistent in the NMR solvent; however, varying solubilities of compounds demanded the use of different solvents.

Example 3

Synthesis of the Bifunctionalized Photoaffinity Probe 2-amino-5-ethynyl-3-{4-[3-(trifluoromethyl)diazirin-3-yl]phenyl}indol-3-ol

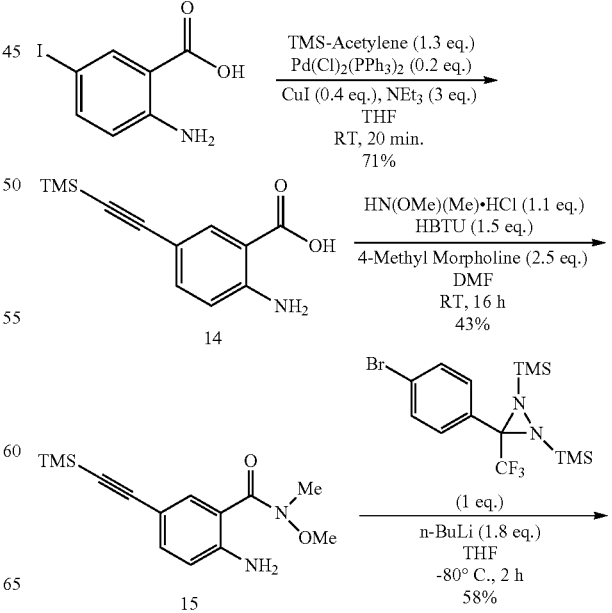

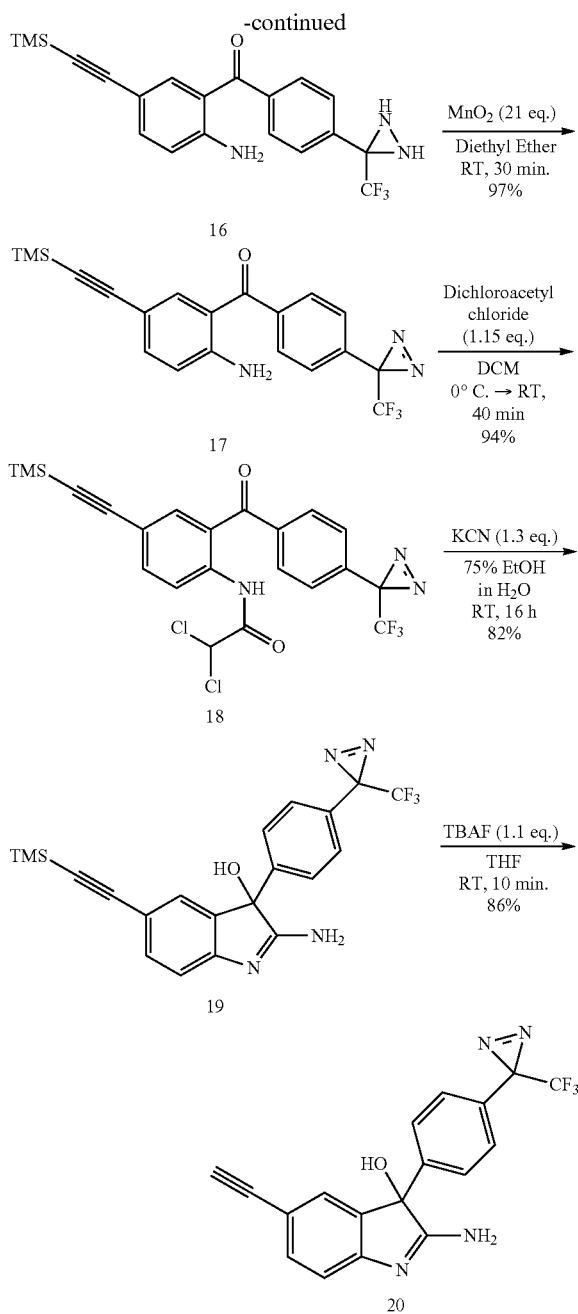

rations Module with Waters Micromass ZQ). Stated mass spectrometry data are from LC-MS analysis.

Evaporation of solvent was conducted by rotary evaporation. For column chromatography purification, silica gel 60, 230-400 mesh was used (EMD). Flash purification systems were also used with associated pre-packaged silica columns (Biotage Isolera and Teledyne Isco Companion).

$^1$H NMR spectra were recorded at 300 or 500 MHz on Bruker 300 and Varian I-500 NMR spectrometers, respectively. $^{13}$C NMR spectra were recorded at 126 MHz using a Varian I-500 NMR spectrometer. Chemical shifts in CDCl$_3$, CD$_3$OD, CD$_3$CN, and (CD$_3$)$_2$O are reported in ppm, relative to CHCl$_3$ ($^1$H NMR, δ=7.24 ppm; $^{13}$C NMR, δ=77.23 ppm), CH$_3$OH ($^1$H NMR, δ=4.87 ppm, 3.31 ppm; $^{13}$C NMR, δ=49.15 ppm), CH$_3$CN ($^1$H NMR, δ=1.94), and (CH$_3$)$_2$O ($^1$H NMR, δ=2.05). Coupling constants are given in hertz. Attempts were made to be consistent in the NMR solvent; however, varying solubilities of compounds demanded the use of different solvents.

2-amino-5-[2-(trimethylsilyl)ethynyl]benzoic acid (14)

2-amino-5-iodobenzoic acid (500 mg, 1.9 mmol, 1 eq.) was dissolved in nitrogen-degassed THF (10 mL) at room temperature. TMS-acetylene (0.34 mL, 2.5 mmol, 1.3 eq.), nitrogen-degassed triethylamine (0.8 mL, 5.7 mmol, 3 eq.), dichloro-bis(triphenylphosphine)palladium(II) (267 mg, 0.4 mmol, 0.2 eq.), and copper iodide (145 mg, 0.8 mmol, 0.4 eq.) were added, in order, to the reaction in the dark. The reaction was then stirred at room temperature for 20 minutes. The solvent was evaporated, and the residue was purified on silica column (DCM/MeOH, 39:1→19:1) to result in 315 mg (71%) of the title compound as a dark orange solid. $^1$H NMR (500 MHz, CDCl$_3$) δ 8.07 (d, J=1.7, 1H, Ar—H), 7.37 (dd, J=1.8, 8.6, 1H, Ar—H), 6.57 (d, J=8.6, 1H, Ar—H), 0.22 (s, 9H, SiC$_3$H$_9$). $^{13}$C NMR (126 MHz, CDCl$_3$) δ 173.11 (COOH), 151.15 (C—Ar), 138.41 (C—Ar), 136.64 (C—Ar), 116.94 (C—Ar), 111.06 (C—Ar), 109.23 (C—Ar), 104.98 (CSi(CH$_3$)$_3$), 92.02 (CCSi(CH$_3$)$_3$), 0.29 (Si(CH$_3$)$_3$). Exact Mass, 233.09. 231.7418 [M−H]$^−$, 233.7569 [M+H]$^+$.

2-amino-N-methoxy-N-methyl-5-[2-(trimethylsilyl) ethynyl]benzamide (15)

2-amino-5-[2-(trimethylsilyl)ethynyl]benzoic acid (630 mg, 2.7 mmol, 1 eq.), HBTU (1.54 g, 4.0 mmol, 1.5 eq.), and 4-methylmorpholine (0.74 mL, 6.7 mmol, 2.5 eq.) were added, in order, to DMF (10 mL) and stirred at room temperature for 10 minutes. N,O-dimethylhydroxylamine hydrochloride (290 mg, 3.0 mmol, 1.1 eq.) was then added to the reaction, and the reaction was stirred at room temperature for 16 hours. Water was then added (20 mL), and the reaction was extracted three times with ethyl acetate (50 mL each). To remove residual water, saturated sodium chloride (20 mL) was added to the organic layer, and the organic layer was separated and dried over sodium sulfate. The solvent was evaporated by rotary evaporation, and the residue was purified on silica column (hexanes/ethyl acetate, 3:1) to result in 320 mg (43%) of the title compound as an orange solid. $^1$H NMR (500 MHz, CDCl$_3$) δ 8.38 (d, J=1.5, 1H, Ar—H), 7.82 (dd, J=1.5, 7.5, 1H, AR—H), 7.10 (d, J=7.3, 1H, Ar—H), 5.61 (s, 2H, NH$_2$), 4.09 (s, 3H, OCH$_3$), 3.66 (s, 3H, NCH$_3$), 0.22 (s, 9H, Si(CH$_3$)$_3$). $^{13}$C NMR (126 MHz, CDCl$_3$) δ 169.20 (CON), 147.35 (C—Ar), 135.24 (C—Ar), 133.50 (C—Ar), 116.65 (C—Ar), 116.55 (C—Ar), 111.21 (C—Ar), 105.40

All solvents for reactions, extractions, and chromatography were of analytical grade. Dichloromethane, N,N-dimethylformamide, methanol, and tetrahydrofuran were passed through an alumina column (A-2) and supported copper redox catalyst (Q-5 reactant). All other solvents, except for ethanol (Pharmco-Aaper), were obtained from Aldrich. Solvents were used without further purification, except where noted.

Reaction vessels were oven-dried for at least 12 hours, and reactions took place in either argon or nitrogen atmospheres. All reactions were magnetically stirred.

Reactions were monitored by thin layer chromatography (TLC) using silica gel 60 plates, treated with 254 nm-fluorescent dye (EMD) and by LC-MS (Waters 2690 Separations Module with Waters Micromass LCT or Waters 2795 Sepa- (CSi(CH$_3$)$_3$), 91.90 (CCSi(CH$_3$)$_3$), 61.44 (NOCH$_3$), 34.53 (NCH$_3$), 0.29 (Si(CH$_3$)$_3$). Exact Mass, 276.13. 277.1046 [M+H]$^+$.

2-({4-[3-(trifluoromethyl)diaziridin-3-yl]phenyl}carbonyl)-4-[2-(trimethylsilyl)ethynyl]aniline (16)

2-amino-N-methoxy-N-methyl-5-[2-(trimethylsilyl)ethynyl]benzamide (403 mg, 1.5 mmol, 1 eq.) and 3-(4-bromophenyl)-3-(trifluoromethyl)-1,2-bis(trimethylsilyl)diaziridine (synthesized by a 5-step process: Bender et al., 2007, 599 mg, 1.5 mmol, 1 eq.) were added together in a round-bottom flask and purged with nitrogen. THF was added, and the reaction was stirred at room temperature until all solids dissolved. The reaction was then cooled to −80° C. in a diethyl ether/dry ice bath, and 2.5 M n-butyllithium in hexanes (1.0 mL, 2.6 mmol, 1.8 eq.) was added, causing the reaction to turn a dark red color. The reaction was stirred at −80° C. for 2 hours and then quenched with saturated ammonium chloride solution (20 mL). The quenched reaction was extracted three times with ethyl acetate (50 mL each). The organic layer was then dried over sodium sulfate, and the solvent was evaporated. Purification on silica column (hexanes/ethyl acetate, 3:1→1:1) resulted in 342 mg (58%) of the title compound as a yellow solid. $^1$H NMR (500 MHz, CDCl$_3$) δ 7.69 (dd, J=8.2, 37.0, 4H, Ar—H), 7.50 (d, J=1.8, 1H, Ar—H), 7.37 (dd, J=1.9, 8.6, 1H, Ar—H), 6.65 (d, J=8.6, 1H, Ar—H), 6.32 (s, 2H, NH$_2$), 2.88 (d, J=8.6, 1H, CNH), 2.32 (d, J=8.8, 1H, CNH), 0.18 (s, 9H, Si(CH$_3$)$_3$). $^{13}$C NMR (126 MHz, CDCl$_3$) δ 197.58 (CO), 151.25 (C—Ar), 141.43 (C—Ar), 138.23 (C—Ar), 138.06 (C—Ar), 134.66 (C—Ar), 129.57 (C—Ar), 128.37 (q, C—Ar, J=0.57), 123.55 (q, J=278.40, CF$_3$), 117.35 (C—Ar), 117.19 (C—Ar), 110.28 (C—Ar), 104.90 (CSi(CH$_3$)$_3$), 92.18 (CCSi(CH$_3$)$_3$), 58.05 (q, J=36.3, C(NH)$_2$), 0.25 (Si(CH$_3$)$_3$). Exact Mass, 403.13. 402.1046 [M−H]$^-$, 404.1982 [M+H]$^+$.

2-({4-[3-(trifluoromethyl)diazirin-3-yl]phenyl}carbonyl)-4-[2-(trimethylsilyl)ethynyl]aniline (17)

2-({4-[3-(trifluoromethyl)diaziridin-3-yl]phenyl}carbonyl)-4-[2-(trimethylsilyl)ethynyl]aniline (66 mg, 0.16 mmol, 1 eq.) was dissolved in diethyl ether (10 mL) and manganese(IV) oxide (300 mg, 3.4 mmol, 21 eq.) was added to the solution. The reaction was stirred at room temperature for 30 minutes and then filtered through Celite with DCM to remove the manganese(IV) oxide. The solvent was evaporated, and the residue was purified on silica column (hexanes/ethyl acetate, 9:1→2:1), resulting in 64 mg (97%) of the title compound as a yellow-orange solid. $^1$H NMR (500 MHz, CDCl$_3$) δ 7.63 (d, J=8.4, 2H, Ar—H), 7.46 (d, J=1.7, 1H, Ar—H), 7.37 (dd, J=1.8, 8.6, 1H, Ar—H), 7.28 (d, J=8.2, 2H, Ar—H), 6.64 (d, J=8.6, 1H, Ar—H), 6.30 (s, 2H, NH$_2$), 0.18 (s, 9H, Si(CH$_3$)$_3$). $^{13}$C NMR (126 MHz, CDCl$_3$) δ 197.20 (CO), 151.24 (C—Ar), 140.72 (C—Ar), 138.19 (C—Ar), 137.94 (C—Ar), 132.27 (C—Ar), 129.59 (C—Ar), 126.48 (q, C—Ar, J=1.19), 122.13 (q, J=274.80, CF$_3$), 117.35 (C—Ar), 117.10 (C—Ar), 110.28 (C—Ar), 104.86 (CSi(CH$_3$)$_3$), 92.21 (CCSi(CH$_3$)$_3$), 28.62 (q, J=40.69, CN$_2$), 0.22 (Si(CH$_3$)$_3$). Exact Mass, 401.12. 399.7011 [M−H]$^-$, 401.7108 [M+H]$^+$.

2,2-dichloro-N-[2-({4-[3-(trifluoromethyl)diazirin-3-yl]phenyl}carbonyl)-4-[2-(trimethylsilyl)ethynyl]phenyl]acetamide (18)

2-({4-[3-(trifluoromethyl)diazirin-3-yl]phenyl}carbonyl)-4-[2-(trimethylsilyl)ethynyl]aniline (47 mg, 0.12 mmol, 1 eq.) was dissolved in DCM (10 mL) and cooled to 0° C. Dichloroacetyl chloride (0.013 mL, 0.14 mmol, 1.15 eq.) was then added, and the reaction was stirred at 0° C. for 10 minutes. The reaction was then warmed to room temperature and stirred for 30 minutes. The solvent was evaporated, and the residue was purified by silica column (hexanes/ethyl acetate, 3:1), resulting in 57 mg (94%) of the title compound as a yellow oil. $^1$H NMR (500 MHz, CDCl$_3$) δ 11.83 (s, 1H, CHCl$_2$), 8.56 (d, J=8.7, 1H, Ar—H), 7.76 (d, J=9.1, 2H, Ar—H), 7.69 (dd, J=1.5, 8.8, 1H, Ar—H), 7.61 (d, J=1.8, 1H, Ar—H), 7.32 (d, J=8.2, 2H, Ar—H), 6.03 (s, 1H, NH), 0.19 (s, 9H, Si(CH$_3$)$_3$). $^{13}$C NMR (126 MHz, CDCl$_3$) δ 197.81 (Ar$_2$—CO), 163.13 (NCOC), 139.23 (C—Ar), 138.79 (C—Ar), 138.33 (C—Ar), 136.61 (C—Ar), 134.08 (C—Ar), 130.47 (C—Ar), 126.71 (q, J=1.23, C—Ar), 123.41 (C—Ar), 122.03 (q, J=274.68, CF$_3$), 121.60 (C—Ar), 120.94 (C—Ar), 103.04 (CSi(CH$_3$)$_3$), 96.22 (CCSi(CH$_3$)$_3$), 67.16 (CCl$_2$), 28.64 (q, J=40.83, CN$_2$), 0.03 (Si(CH$_3$)$_3$). Exact Mass, 511.05. 509.4841 [M−H]$^-$, 511.487 [M+H]$^+$.

2-amino-3-{4-[3-(trifluoromethyl)diazirin-3-yl]phenyl}-5-[2-(trimethylsilyl)ethynyl]indol-3-ol (19)

2,2-dichloro-N-[2-({4-[3-(trifluoromethyl)diazirin-3-yl]phenyl}carbonyl)-4-[2-(trimethylsilyl)ethynyl]phenyl]acetamide (57 mg, 0.11 mmol, 1 eq.) was dissolved in EtOH (3 mL). Potassium cyanide (9.4 mg, 0.14 mmol, 1.3 eq.) in water (1 mL) was added to the reaction, and the reaction was stirred at room temperature for 16 hours. The EtOH was evaporated, and additional water (8 mL) was added. The reaction was then extracted three times with 5% isopropanol in DCM (20 mL each), and the organic layer was dried over sodium sulfate. The solvent was evaporated, and the residue was purified on silica column (DCM/MeOH, 39:1→19:1→9:1→4:1) to result in 39.2 mg (82%) of the title compound as a yellow solid. $^1$H NMR (500 MHz, CD$_3$OD) δ 7.44 (d, J=8.5, 2H, Ar—H), 7.29 (dd, J=1.8, 8.8, 1H, Ar—H), 7.22 (d, J=8.3, 2H, Ar—H), 7.02-6.94 (m, 2H, Ar—H), 0.18 (s, 9H, SiC$_3$H$_9$). $^{13}$C NMR (126 MHz, CD$_3$OD) δ 180.56 (C—NH$_2$), 156.85 (C—Ar), 144.59 (C—Ar), 140.89 (C—Ar), 135.13 (C—Ar), 129.58 (C—Ar), 127.89 (d, J=0.88, C—Ar), 127.66 (C—Ar), 126.99 (C—Ar), 123.70 (q, J=273.80, CF$_3$), 117.82 (C—Ar), 116.69 (C—Ar), 107.08 (CSi(CH$_3$)$_3$), 92.94 (CCSi(CH$_3$)$_3$), 84.20 (Ar—COH), 29.55 (q, J=40.25, CN$_2$), 0.23 (Si(CH$_3$)$_3$). Exact Mass, 428.13. 426.6786 [M−H]$^-$, 428.6918 [M+H]$^+$.

2-amino-5-ethynyl-3-{4-[3-(trifluoromethyl)diazirin-3-yl]phenyl}indol-3-ol (20)

2-amino-3-{4-[3-(trifluoromethyl)diazirin-3-yl]phenyl}-5-[2-(trimethylsilyl)ethynyl]indol-3-ol (30.5 mg, 0.07 mmol, 1 eq.) was dissolved in THF (5 mL), and 1 M TBAF in THF (0.078 mL, 0.08 mmol, 1.1 eq.) was added. The reaction was stirred at room temperature for 10 minutes. Solvents were then evaporated, and the residue was purified by silica column (DCM/MeOH, 39:1→19:1→9:1→4:1), resulting in 21.8 mg (86%) of the title compound as a yellow solid. $^1$H NMR (500 MHz, CD$_3$OD) δ 7.45 (d, J=8.5, 2H, Ar—H), 7.33 (dd, J=1.5, 8.0, 1H, Ar—H), 7.23 (d, J=8.2, 2H, Ar—H), 7.10-6.94 (m, 2H, Ar—H). $^{13}$C NMR (126 MHz, CD$_3$OD) δ 180.61 (CNH$_2$), 156.96 (C—Ar), 144.65 (C—Ar), 140.97 (C—Ar), 135.30 (C—Ar), 129.59 (C—Ar), 127.92 (d, J=0.90, C—Ar), 127.76 (C—Ar), 127.02 (C—Ar), 123.73 (q, J=273.90, CF$_3$), 117.13 (C—Ar), 116.69 (C—Ar), 84.96 (CCH), 84.23 (Ar—COH), 77.31 (CCH), 29.56 (q, J=40.35, CN$_2$). Exact Mass, 356.09. 354.7202 [M−H]$^-$, 356.7268 [M+H]$^+$.

Example 4

Synthesis of Compound 1

Scheme 4:

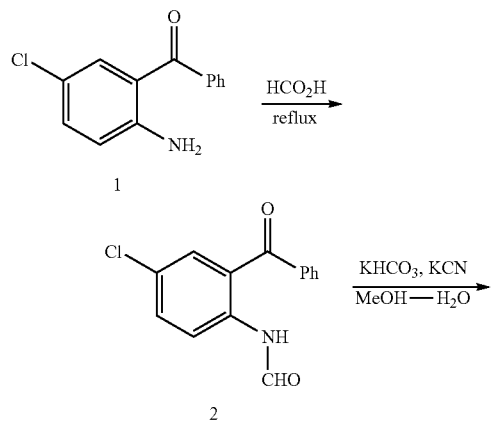

Representative Procedures:

Scheme 5:

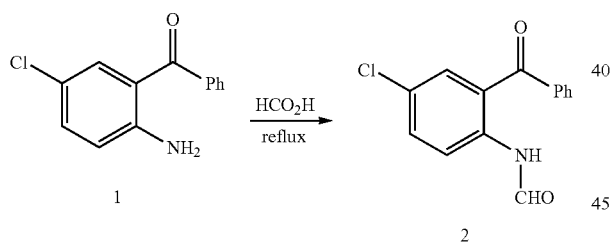

5-Chloro-2-aminobenzophenone (1, 15.78 g, 68.1 mmol) and formic acid (200 mL) were refluxed (117° C.) under argon for 24 h. After evaporating the excess of formic acid, the residue obtained was directly loaded onto the silica gel column (0-30% EtOAc/Hexanes) which afforded compound 2 (16.0 g, 90%) as yellow viscous oil.

Scheme 6:

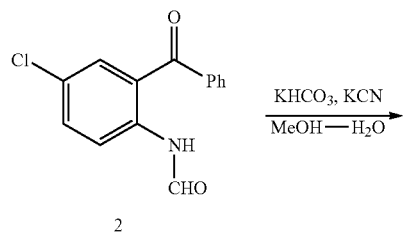

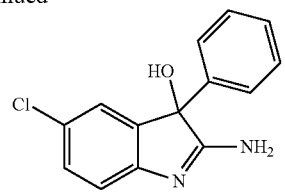

A mixture of 2 (10.0 g, 38.5 mmol, 1.0 equiv) and KHCO$_3$ (3.86 g, 38.5 mmol, 1.0 equiv) was dissolved in MeOH—H$_2$O (1:1, 100 mL) by heating at 90° C. (oil-bath) for 15-20 min. The flask was removed from an oil bath and then KCN (3.26 g, 50.0 mmol, 1.3 equiv) was added. The reaction mixture was stirred at room temperature resulting in the precipitate formation within 1 h. The stirring was continued until LC/MS showed complete disappearance of 2 (2-3 h). Water was added to the reaction mixture and the solid was collected by filtration and washed thoroughly with water. Recrystallization with acetonitrile (preferred) or ethanol afforded compound as white solid (8.1 g, 81%).

Example 5

Representative Synthesis for 2-aminoindoles

Scheme 7:

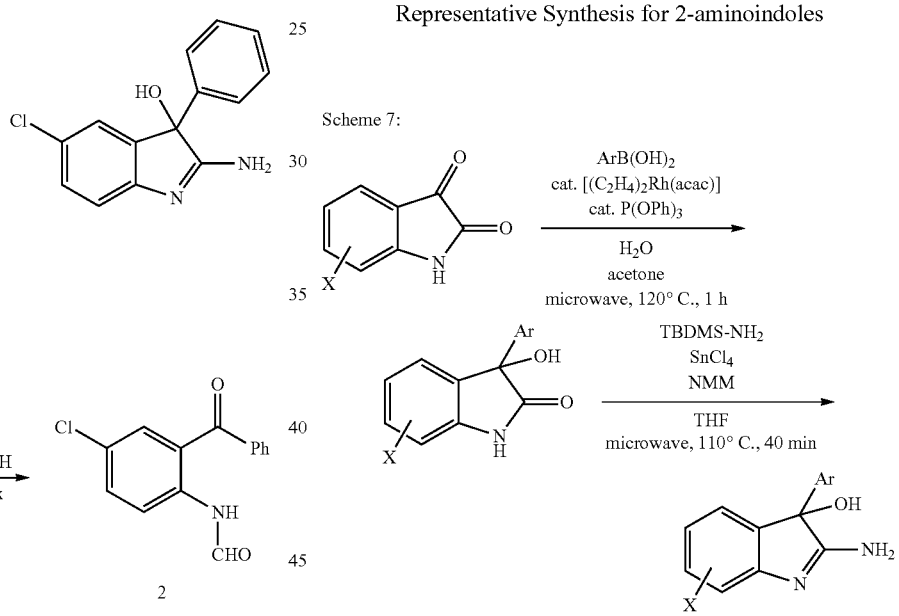

Representative Procedures:

Scheme 8:

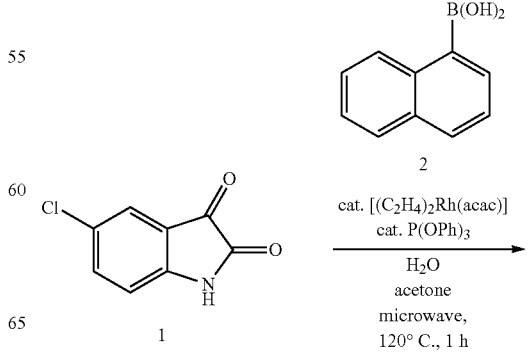

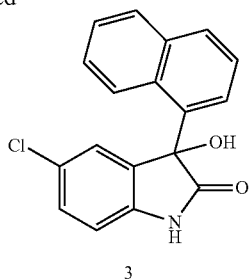

A microwave vial was charged with 5-chloroisatin 1 (1 g, 1.0 equiv), 1-naphthylboronic acid 2 (1.895 g, 2.0 equiv), [(C$_2$H$_4$)$_2$Rh(acac)] (43 mg, 0.03 equiv, purchased from Strem), P(OPh)$_3$ (0.11 mL, 0.07 equiv), water (0.2 mL, 2.0 equiv), and 10 mL acetone. The reaction mixture was then microwaved at 120° C. for 1 h after which the LC-MS analysis showed the completion of the reaction. 1M HCl was added to the reaction and extracted twice with CH$_2$Cl$_2$. The combined organic extracts were dried over MgSO$_4$, filtered, and concentrated in vacuo to give a residue which was recrystallized from acetone/hexanes to give 3 (1.490 g, 87%) as a grey solid. Instead of doing an aqueous workup, the reaction mixture can also be directly passed through a short pad of silica gel eluting with acetone and then concentration followed by recrystallization as above.

Scheme 9:

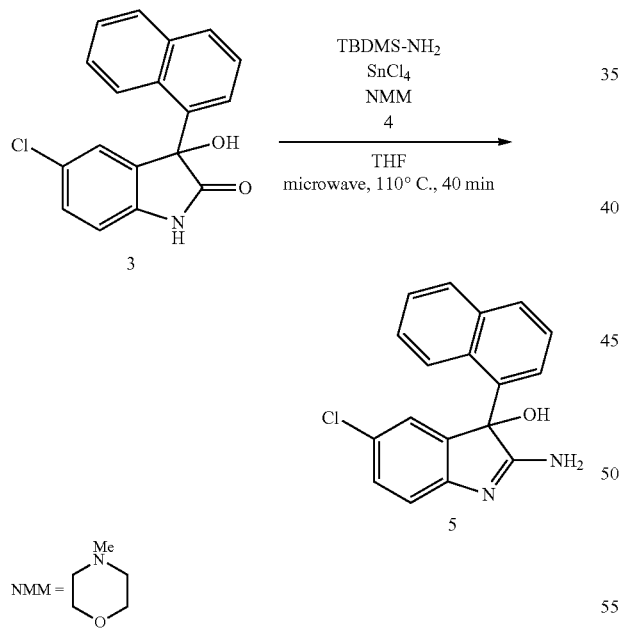

A microwave vial was charged with 3 (300 mg, 1.0 equiv), TBDMS-NH$_2$ 4 (510 mg, 3.2 ml from the stock solution prepared below, 4.0 equiv), NMM (0.43 mL, 4.0 equiv), and 10 mL dry THF under an argon atmosphere. To this mixture was carefully added SnCl$_4$ (1M in CH$_2$Cl$_2$, 2 mL, 2.0 equiv). The mixture was microwave at 110° C. for 40 min. 1M aq. HCl was added and the reaction mixture was extracted with CH$_2$Cl$_2$ (1×40 mL) and twice with CH$_2$Cl$_2$-i-PrOH mixture (while saturating the aq. phase with NaCl). The organic extracts were then combined, dried over MgSO$_4$, filtered, concentrated in vacuo, and the residue obtained was dissolved in minimal amount of CH$_2$Cl$_2$ and loaded directly onto the ISCO (silica gel) column (0-7% MeOH/CH$_2$Cl$_2$ containing 2% Et$_3$N) and then recrystallization with CH$_2$Cl$_2$/hexanes gave 5 (150 mg, yield: 50%) as an off-white solid.

Preparation of TBDMS-NH$_2$ 4 Reagent

Ammonia gas was bubbled (for 2-3 minutes) through a solution of TBDMSCl (5 g) in 20 mL THF at 0° C., which immediately resulted in the precipitate formation of NH$_4$Cl. The cold bath was removed and the reaction mixture was then purged through an argon gas for 15-30 min to completely remove the unreacted ammonia. The reaction mixture was filtered through a syringe-less filter and thoroughly washed with THF in such a way that that the final volume of the solution containing TBDMS-NH$_2$ is 24 mL. It was assumed that the yield of the reaction is 90% (3.9 g) and this solution was stored at room temperature under an argon atmosphere and used in the above reaction without further purification.

Example 6

Representative Synthesis of 2-aminoindoles

Scheme 10:

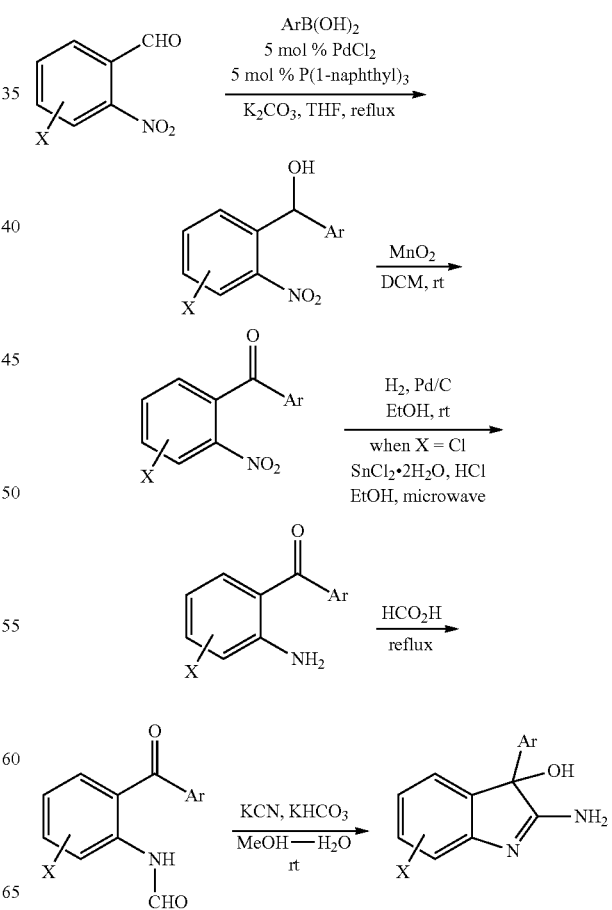

Representative Procedures:

Scheme 11:

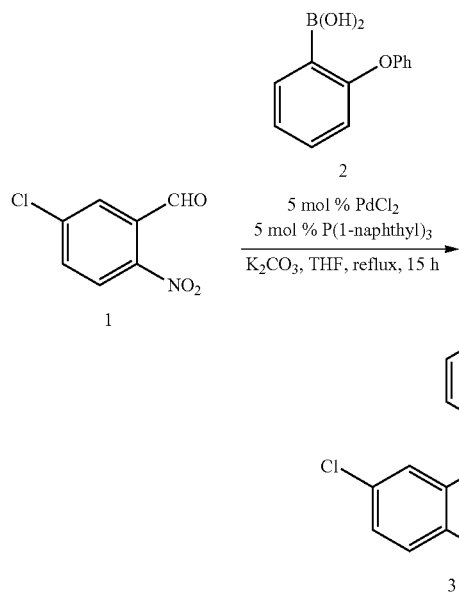

A 20 mL capacity microwave vial was loaded with PdCl$_2$ (0.05 equiv, 24 mg), P(1-naphthyl)$_3$ (0.05 equiv, 56 mg), boronic acid 2 (2.0 equiv, 1.153 g), aldehyde 1 (1.0 equiv, 500 mg), K$_2$CO$_3$ (3.0 equiv, 1.117 g), and dry THF (12 mL). The vial was sealed and purged with N$_2$ for 5-10 min. The reaction mixture was heated at 65° C. for 15 h, cooled to room temperature. Water was added and the reaction mixture was extracted with EtOAc (3×40 mL). The combined EtOAc extracts were dried over MgSO$_4$, filtered, concentrated in vacuo, and the residue obtained was dissolved in minimal amount of CH$_2$Cl$_2$ and loaded directly onto the ISCO (silica gel) column (0-20% EtOAc/hexanes) which gave diaryl-methanol 3 (500 mg, yield: 52%) as a light yellow oil.

Scheme 12:

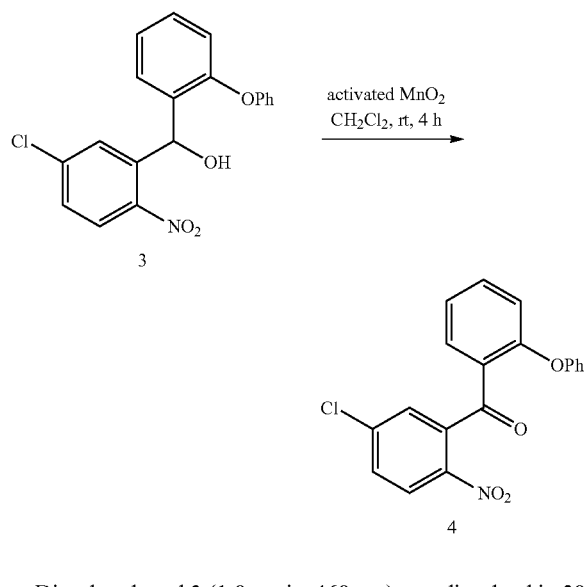

Diarylmethanol 3 (1.0 equiv, 460 mg) was dissolved in 20 mL CH$_2$Cl$_2$ and to this solution was added an activated MnO$_2$ (16.0 equiv, 1.80 g). The reaction mixture was stirred under an atmosphere of nitrogen at room temperature for 4 h after which the LC-MS analysis showed the completion of the reaction. The reaction mixture was filtered over celite and washed thoroughly with methanol and CH$_2$Cl$_2$. The solvents were evaporated in vacuo affording diarylketone 4 (392 mg, yield: 86%) as a light yellow oil which was used in the next step without further purification.

Scheme 13:

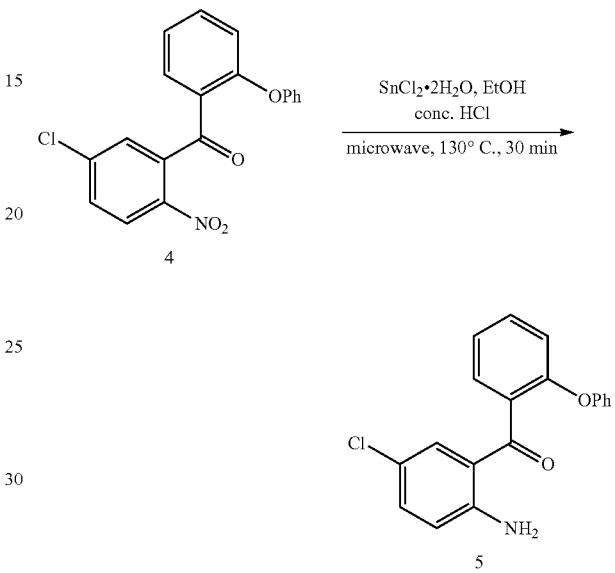

A mixture of 4 (390 mg, 1.0 equiv), SnCl$_2$.2H$_2$O (5.0 equiv, 1.244 g), few drops of conc. HCl, and 15 mL EtOH was microwaved at 130° C. for 30 min. The LC-MS analysis showed the completion of the reaction. It was found that the presence of HCl drives the reaction to completion faster than without it. (The reaction can also be performed under conventional heating, i.e. at the reflux temperature of EtOH). The solvent was evaporated in vacuo and the residue obtained was dissolved in minimal amount of CH$_2$Cl$_2$ and loaded directly onto the ISCO (silica gel) column (0-1% MeOH/CH$_2$Cl$_2$) which gave 2-aminobenzophenone 5 (321 mg, yield: 90%) as a light yellow oil.

The nitro group can also be reduced under hydrogenation conditions provided the functional groups present in the molecule are stable to the aforementioned conditions. For example:

Scheme 14:

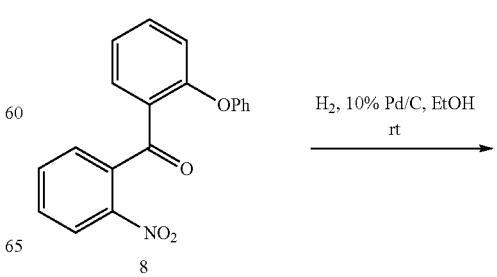

-continued

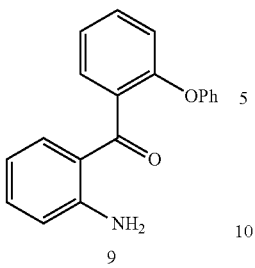

9

To a solution of diarylketone 8 (600 mg) in 20 mL EtOH was added 100 mg 10% Pd/C. The reaction mixture was evacuated using house vacuum and then H$_2$ balloon was introduced into the flask. The mixture was stirred at room temperature for 2 h (or until LC-MS showed the completion of the reaction). After completion, the reaction mixture was filtered over celite, washed with MeOH, and concentrated in vacuo to afford 9 (441 mg, 81%) as a yellow viscous oil which was used in the next step without further purification.

Scheme 15:

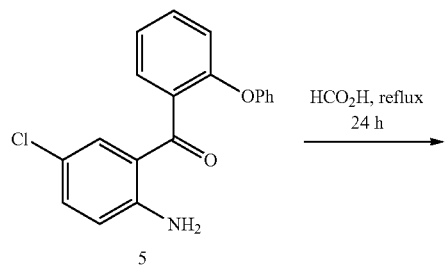

2-aminobenzophenone 5 (321 mg, 1.0 equiv) and formic acid (20 mL) were refluxed (117° C.) under argon for 24 h. After evaporating the excess of formic acid, the residue obtained was dissolved in minimal amount of CH$_2$Cl$_2$ and loaded directly onto the ISCO (silica gel) column (0-30% EtOAc/hexanes) which gave 6 (310 mg, yield: 89%) as a light yellow oil.

Scheme 16:

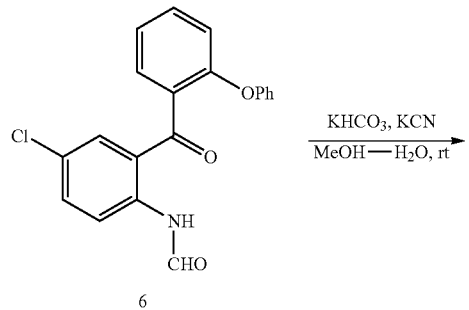

-continued

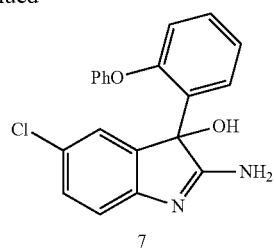

7

A mixture of 6 (310 mg, 1.0 equiv) and KHCO$_3$ (89 mg, 1.0 equiv) was dissolved in MeOH—H$_2$O (1:1, 6 mL) by heating at 70° C. (oil-bath) for 10-15 min. The flask was removed from an oil bath and then KCN (75 mg, 1.3 equiv) was added. The reaction mixture was stirred at room temperature overnight. The stirring was continued until LC/MS showed complete disappearance of 6. Water was added to the reaction mixture resulting in the formation of solid which was collected by filtration, washed with water and hexanes to give aminoindole 7 (220 mg, yield: 71%) as a white solid.

(Important: If addition of water does not result in the ppt. formation, then the mixture can be extracted with CH$_2$Cl$_2$ and once with i-PrOH—CH$_2$Cl$_2$ mixture (saturating the aq. phase with NaCl). The organic extracts were then combined, dried over MgSO$_4$, filtered, concentrated in vacuo, and then recrystallization with CH$_2$Cl$_2$/hexanes would afford pure aminoindole).

Example 7

Representative Synthesis of 2-aminoindoles

Scheme 17:

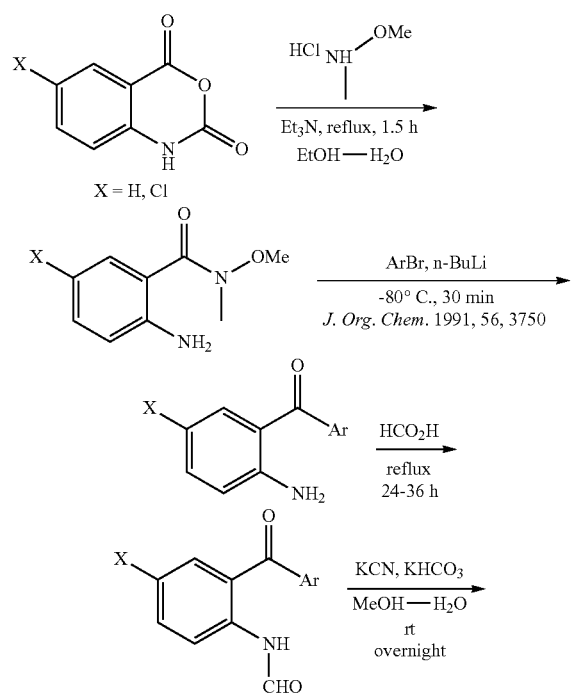

-continued

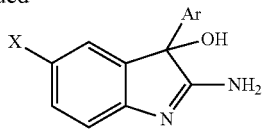

Representative Procedures:

Scheme 18:

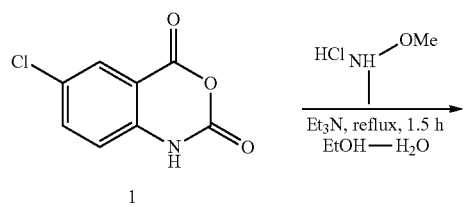

To a solution of N,O-dimethylhydroxylamine hydrochloride (1.5 equiv, 2.962 g) in 90% aq. EtOH (45 mL EtOH and 5 mL H₂O) was added Et₃N (1.5 equiv, 4.23 mL), and after 10 min of stirring at room temperature, 5-chloroisatoic anhydride 1 (1.0 equiv, 4 g) was added in portions. The reaction was then heated at reflux for 90 min and poured into an equal volume of ice and satd. aq. NaHCO₃ and extracted with EtOAc (3×100 mL). The combined EtOAc extracts were dried over MgSO₄, filtered, concentrated in vacuo, and the residue obtained was dissolved in minimal amount of CH₂Cl₂ and loaded directly onto the ISCO (silica gel) column (0-2.5% MeOH/DCM) which gave 2 (2.6 g, yield: 60%) as a light brown solid.

Scheme 19:

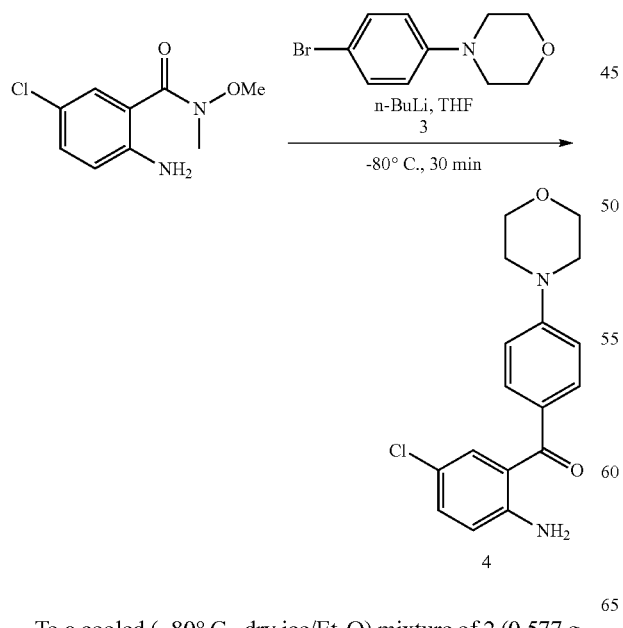

To a cooled (−80° C., dry ice/Et₂O) mixture of 2 (0.577 g, 1.0 equiv) and bromide 3 (0.650 g, 1.0 equiv) in 30 mL dry THF under an argon atmosphere was added n-BuLi (2.5 M in hexanes, 2.2 mL, 2.05 equiv) dropwise. The mixture was stirred at the same temperature for 30 min and quenched with 1M aq. HCl and extracted with EtOAc (3×50 mL). The combined EtOAc extracts were dried over MgSO₄, filtered, concentrated in vacuo, and the residue obtained was dissolved in minimal amount of CH₂Cl₂ and loaded directly onto the ISCO (silica gel) column (0-30% EtOAc/Hexanes) which gave 4 (0.542 g, yield: 64%) as a yellow solid.

See Example (Scheme)) for formylation and cyclization procedures.

Example 8

Synthesis of 2-aminoindoles from Isatins

Scheme 20:

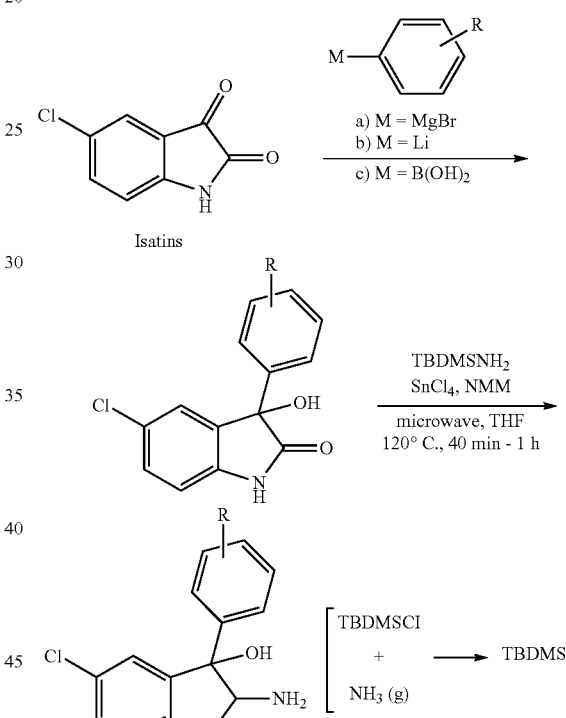

Example 9

Synthesis of 2-aminoindoles from Oxindoles

Scheme 21:

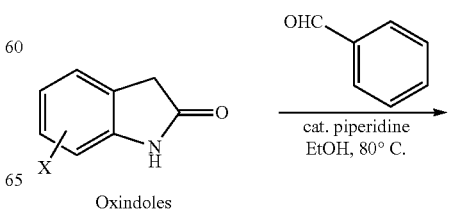

-continued
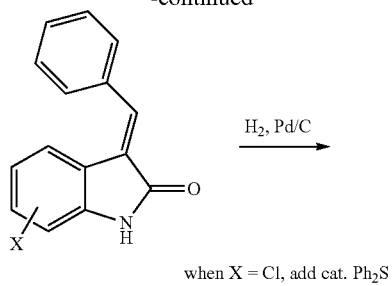
when X = Cl, add cat. Ph₂S
OXONE →
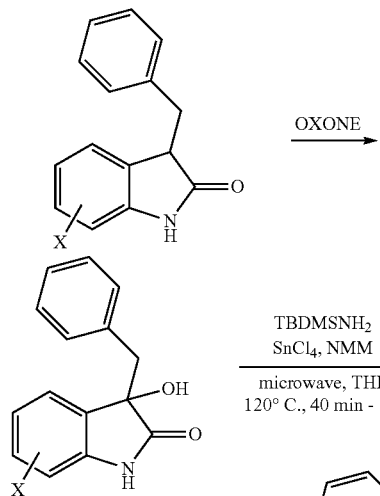
Example 10
Enantioselective Synthesis of 2-aminoindoles
Scheme 22:
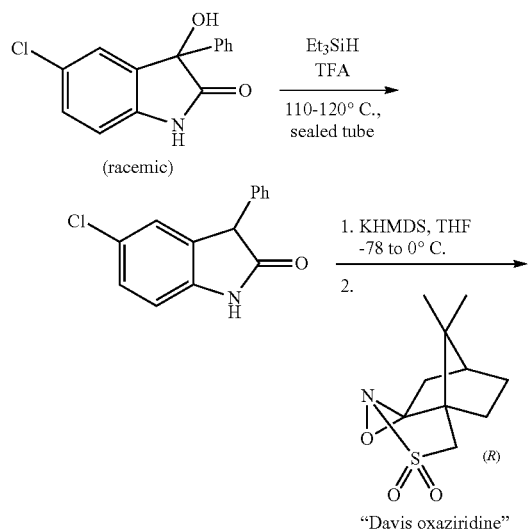
"Davis oxaziridine"
-continued
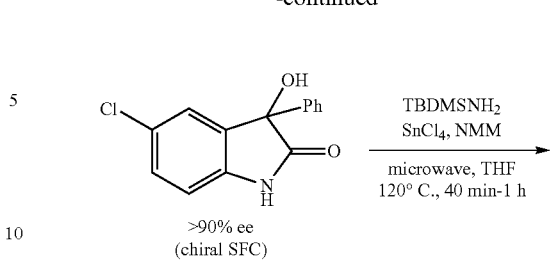
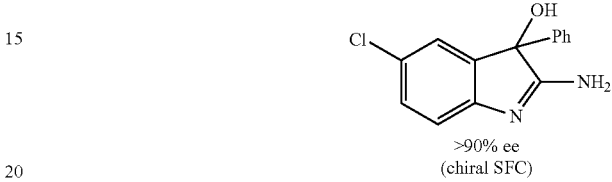
Example 11
Alternate Synthesis of Compound 1
Scheme 23:
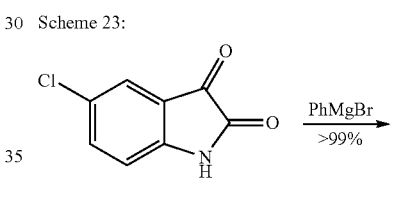
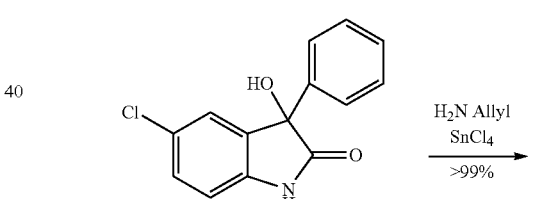
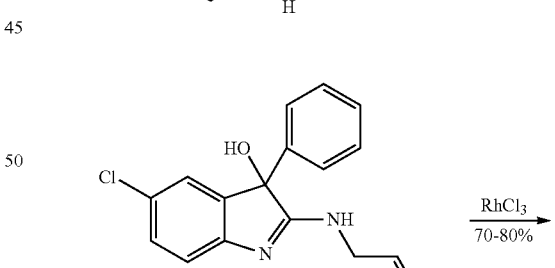
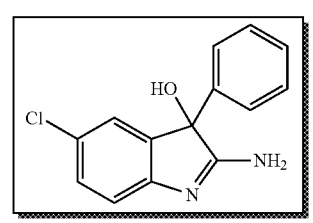

Example 12
Alternate Enantioselective Synthesis of 2-aminoindoles
Scheme 24:
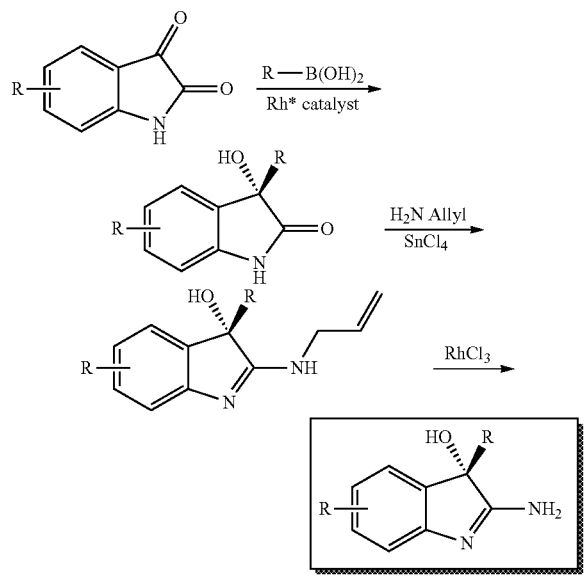
Example 13
Process Syntheses of 2-aminoindoles
Scheme 25:
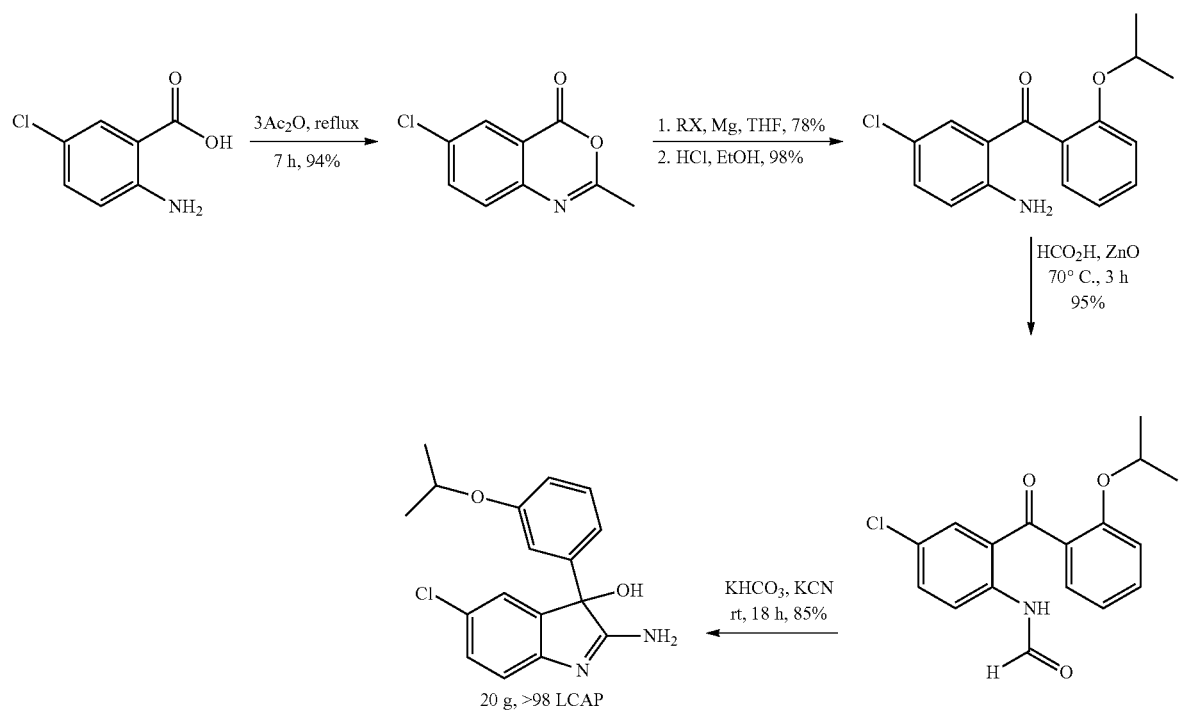

Example 14
Representative Synthesis of Compound 225

Compound 225 was synthesized after four steps:

Scheme 26:

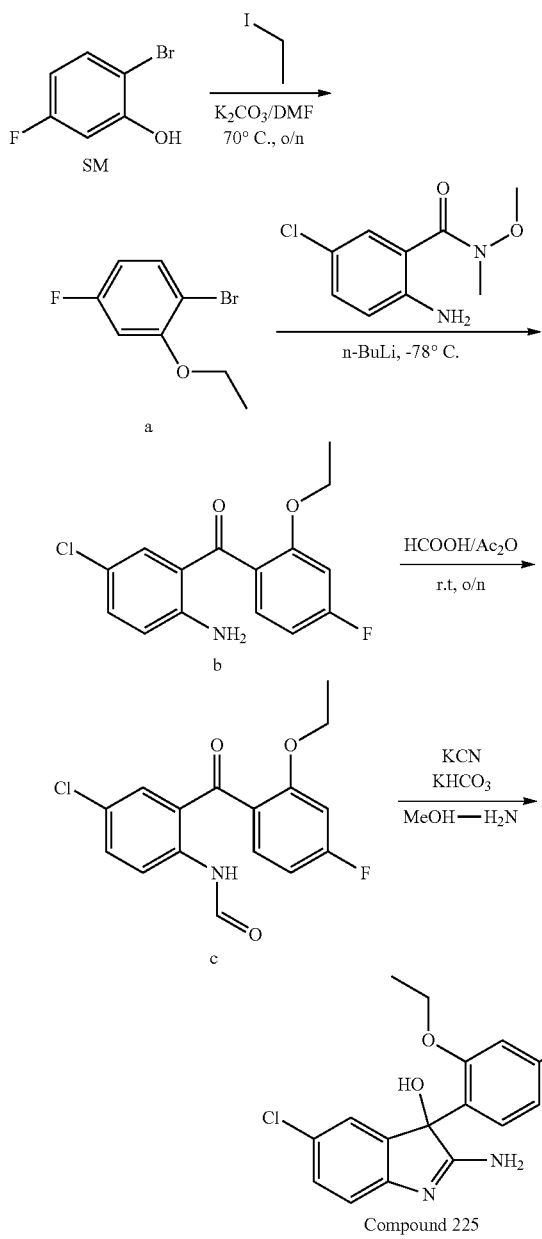

Experimental

Step 1

Scheme 27:

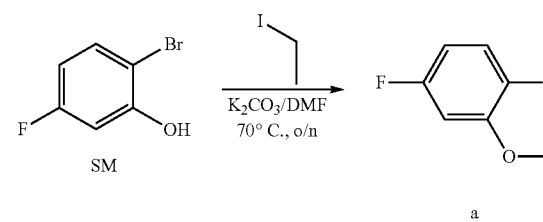

A mixture of SM (1.6 g, 8 mmol), Iodoethane (1.37 g, 8.8 mmol) and $K_2CO_3$ (1.21 g, 8.8 mmol) was dissolved in DMF (10 mL) and the mixture was stirred at 70° C. under $N_2$, overnight. The reaction mixture was diluted with $H_2O$ and extracted with EtOAc. The combined organic phase was dried over $Na_2SO_4$, filtered, concentrated in vacuo. The residue was purified by silica gel column chromatography (PE) to give a (1.5 g, 87%) as a liquid.

Step 2

Scheme 28:

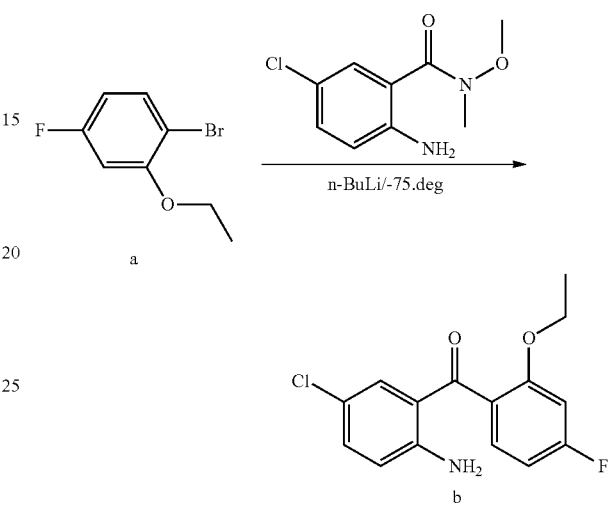

To a solution of a (1.5 g, 6.88 mmol) and 2-amino-5-chloro-N-methoxy-N-methylbenzamide (1.34 g, 6.26 mmol) in anhydrous THF (40 mL) at −780 under $N_2$ was added dropwise n-BuLi (2.5M in hexane, 7.0 mL, 17.5 mmol). The resulting solution was stirred for 1 h at the same temperature, then quenched by saturated aq. $NH_4Cl$ and extracted with ethyl acetate (3×100 mL). The organic layers were separated, combined, dried ($Na_2SO_4$) and concentrated to give a residue, which was purified by flash chromatography over silica gel (PE:EA=20:1) to yield b (1.1 g, 54%).

Step 3

Scheme 29:

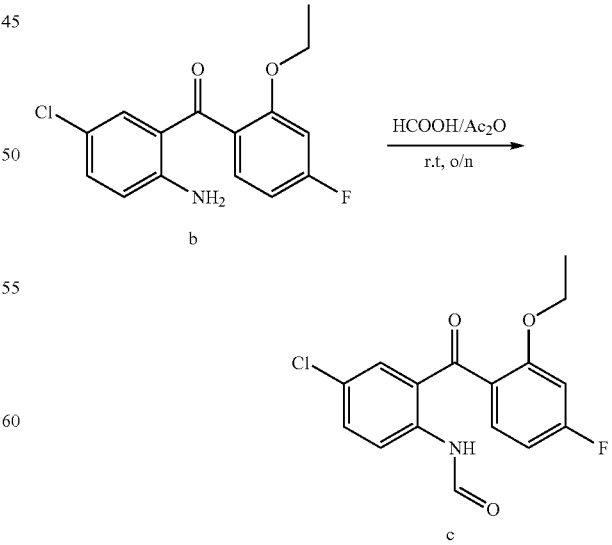

A mixture of acetic anhydride (6 mL) and formic acid (3 mL) was heated at 500 with stirring for 2 h, then cooled to r.t.

The resulting solution was added to a mixture of b (1.1 g, 3.75 mmol) in THF (4 mL). After the mixture was stirred at r.t. overnight, the solution was diluted with H₂O. The formed solid was filtered and washed with hexane to give c (1.05 g, 87%), which was used for next step without further purification.

Step 4

Scheme 30:

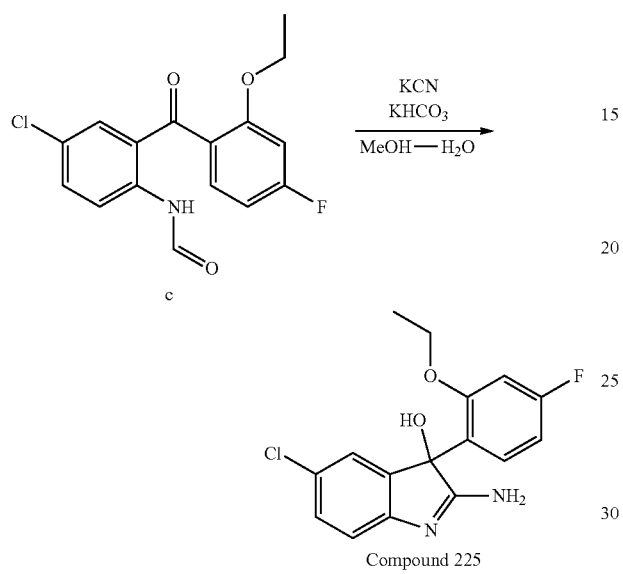

Compound 225

A mixture of c (1.05 g, 3.27 mmol), KHCO₃ (327 mg, 3.27 mmol) and KCN (638 mg, 9.81 mmol) in methanol/water (15 mL/5 mL) was stirred for 3 hrs at room temperature. After the classical work-up, the residue was purified by silica gel column chromatography (DCM/methanol) and then re-crystallized in hexane/methanol to give Compound 225 (600 mg, 57%).

Example 15

Representative Synthesis of Compound 142

Summary

The synthesis of Compound 142 was shown in synthesis scheme. a was synthesized by the reaction of 2-bromo-4-fluorophenol with ethyl iodide. Then a reacted with 2-amino-5-chloro-N-methoxy-N-methylbenzamide to give b, which was reacted with formic acid to afford c. At last, c reacted with potassium cyanide to afford Compound 142.

Scheme 31:

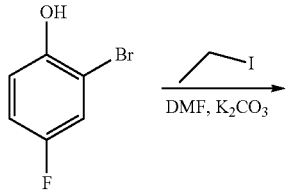

Experimental

Step 1

Scheme 32:

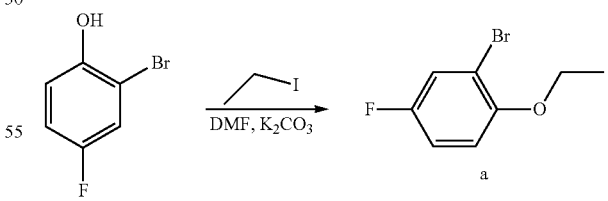

To a solution of 2-bromo-4-fluorophenol (1.9 g, 10 mmol) in DMF (10 ml) was added K₂CO₃ (1.52 g, 11 mmol) and ethyl iodide (1.72 g, 11 mmol). The resulting mixture was stirred for 24 hrs at room temperature. The reaction mixture was diluted with H₂O (40 ml) and extracted with hexane. The organic phase was washed with water, dried, filtered over a plug of silica gel and concentrated to give a (1.85 g, 85%) as a colorless oil.

Step 2

Scheme 33:

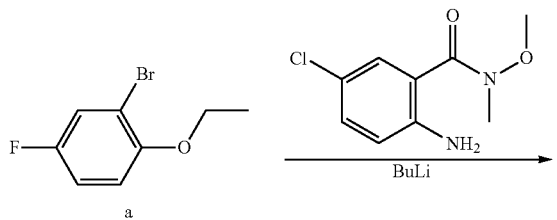

To a mixture of a (1.85 g, 8.5 mmol) and 2-amino-5-chloro-N-methoxy-N-methylbenzamide (1.82 g, 8.5 mmol) in 30 mL of dry THF under a $N_2$ atmosphere was added dropwise n-BuLi (2.5 M in hexanes, 10.0 ml, 25 mmol) at −78° C. The resulting mixture was stirred at the same temperature for 1 h, quenched with aqueous ammonium chloride and extracted with EtOAc (3×100 mL). The combined organic phase was dried over $MgSO_4$, filtered and concentrated in vacuo to give a residue, which was purified by silica gel column chromatography (Hexanes: EtOAc=10:1) to gave b (1.0 g, 40%) as a yellow solid.

Step 3

Scheme 34:

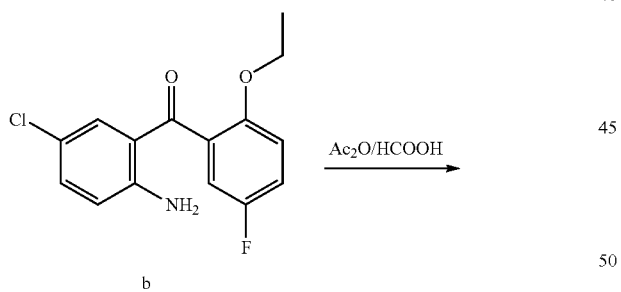

A solution of 2 mL of formic acid and 4 mL of acetic anhydride was heated at 50° C. for 2 h to give the acetic formic anhydride and then cooled to room temperature. To a solution of b (600 mg) in 10 mL of THF was added the acetic formic anhydride (6 mL) prepared in situ. The resulting mixture was stirred at room temperature for 3 hrs. After the completion of the reaction (TLC monitor), the solution was diluted with water (50 ml) and filtered in vacuo to give c (900 mg, 90%) as a yellow solid, which was used for next step without further purification.

Step 4

Scheme 35:

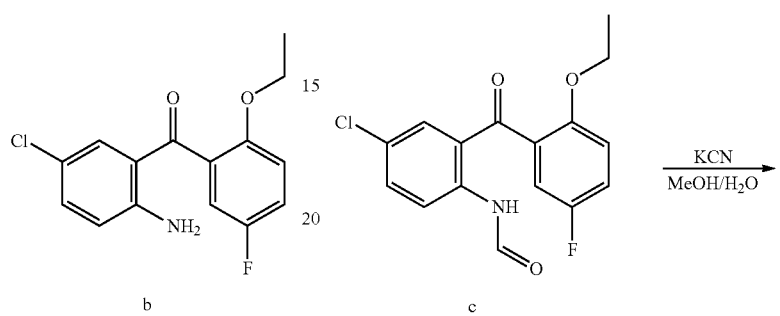

Compound 142

A microwave vial was charged with c (500 mg, 1.6 mmol), KCN (202 mg, 3.2 mmol) and $MeOH/H_2O$ (v/v=1/1, 10 mL). The resulting mixture was heated under microwave at 75° C. for 30 min and cooled to room temperature. The reaction solution was filtered in vacuo and the obtained solid was re-crystallized in methanol to give Compound 142 (199 mg, 40%).

Example 16

Representative Synthesis of Compound 201

Summary

Compound 201 was synthesized via a seven-step route depicted below.

Scheme: 36

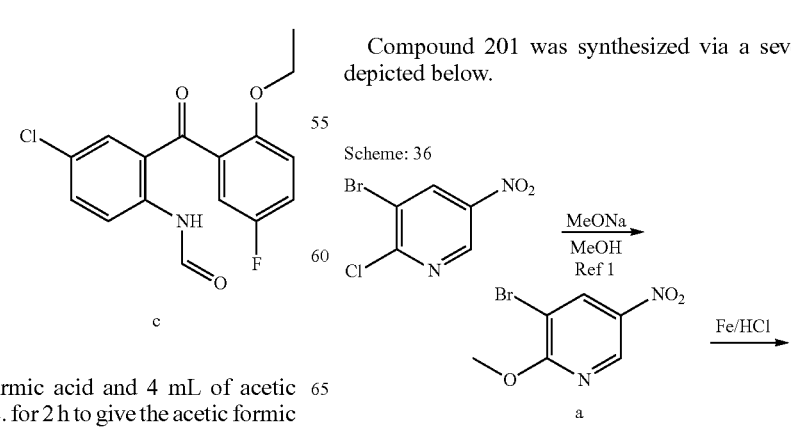

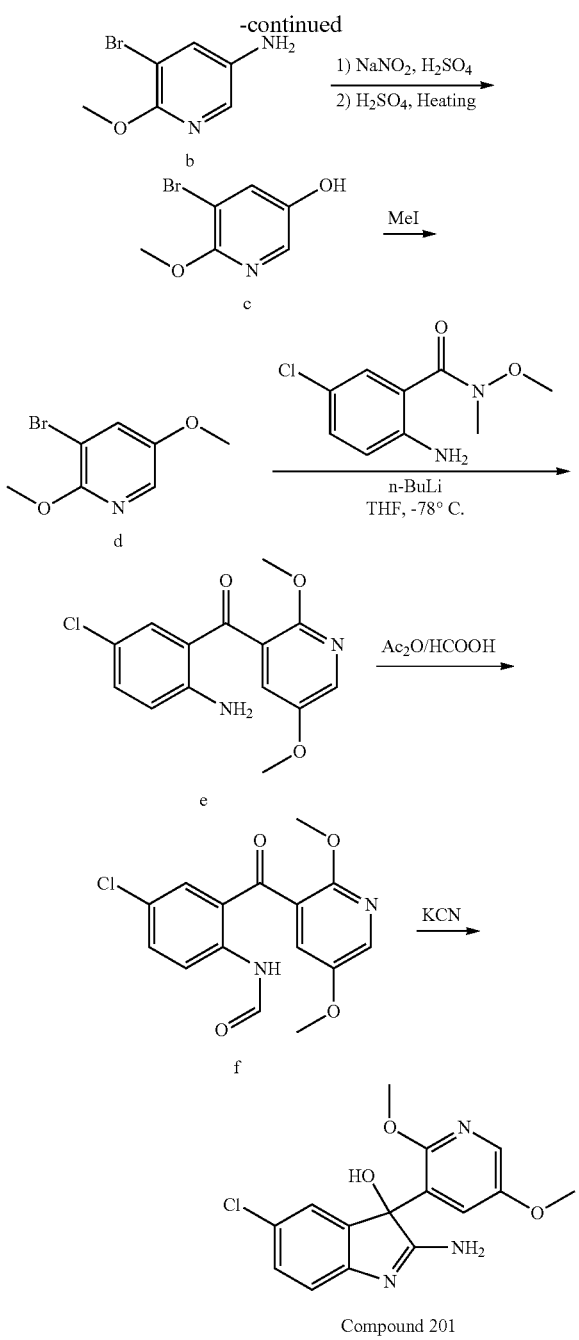

Ref: 1) *Justus Liebigs Annalen der Chemie*, 1937, 529, 291

Experimental

Step 1

Scheme 37:

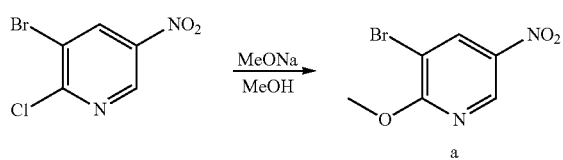

To a solution of 3-bromo-2-chloro-5-nitropyridine (23.5 g, 100 mmol) in 200 mL of CH₃OH was added CH₃ONa (54 g, 1.0 mol) with stirring in an ice bath. The resulting solution was heated at 80° C. for 12 hrs and cooled to room temperature. The reaction mixture was diluted with 200 mL of H₂O and extracted with ethyl acetate (3×250 mL). The organic phase was dried over magnesium sulfate, filtered and concentrated to give a residue, which was purified by column chromatography over silica gel (50:1, petroleum ether/EtOAc) to afford a (6.8 g, 34%) as a yellow oil.

Step 2

Scheme 38:

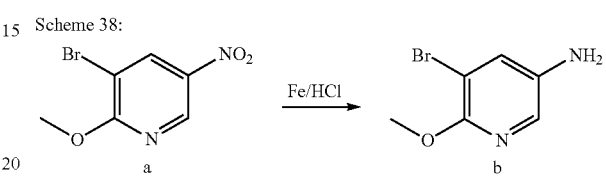

To a solution of a (6.8 g, 29 mmol) in 78 mL of EtOH and 10 mL of H₂O was added 0.8 mL of conc. HCl and iron powder (49 g, 174 mmol) with stirring. The resulting solution was heated at 80° C. under a nitrogen atmosphere for 3 hrs and cooled to room temperature. The reaction mixture was filtered and the filtrate was concentrated to afford b (5.1 g, 86%) as a brown-yellow residue, which was used directly to next step.

Step 3

Scheme 39:

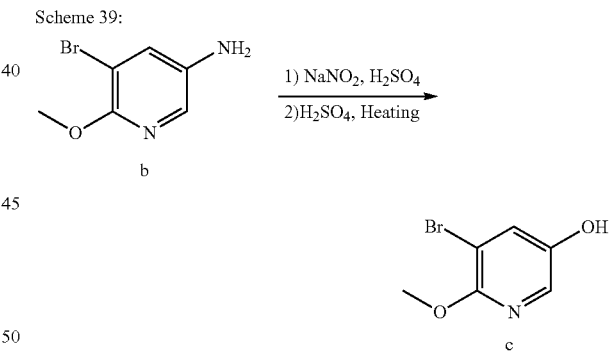

To a solution of b (5.1 g, 25 mmol) in 22 mL of conc. H₂SO₄ and 28 mL of H₂O was added dropwise a solution of NaNO₂(1.75 g, 25 mmol) in 5 mL of H₂O at 0° C. with stirring. The resulting mixture was stirred at 0° C. for 1 h, and then was added dropwise to a 34 mL of 50% aqueous H₂SO₄ solution under reflux. The reaction mixture was stirred under reflux for 2 hrs, cooled to room temperature, neutralized by 3N aqueous NaOH solution to pH=6 under an ice bath and extracted by EtOAc (3×150 mL). The organic phase was dried, filtered and concentrated to a residue, which was purified by column chromatography over silica gel (50:1, CH₂Cl₂/MeOH) to give c (1.16 g, 23%) as a white solid.

Step 4

Scheme 40:

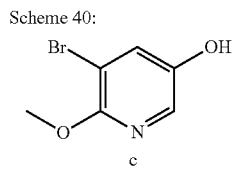

To a solution of c (1.16 g, 5.68 mmol) and K₂CO₃ (2.3 g, 17 mmol) in 35 mL of DMF was added one-portion CH₃I (2.0 g, 14 mmol) under a nitrogen atmosphere at 0° C. with stirring. The resulting solution was heated at 50° C. for 1 h, cooled to room temperature, diluted with 100 mL of water and extracted with DCM (3×70 mL). The organic phase was dried (Na₂SO₄), filtered and concentrated to give a residue, which was purified by column chromatography over silica gel (50:1, petroleum ether/EtOAc) to afford d (1.1 g, 89%) as a yellow liquid.

Step 5

Scheme 41:

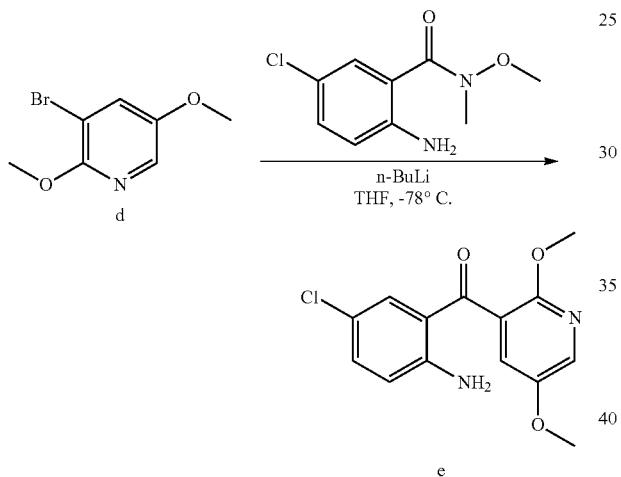

To a solution of d (1.1 g, 5 mmol) and 2-amino-5-chloro-N-methoxy-N-methylbenzamide (1.0 g, 5 mmol) in anhydrous THF (30 mL) was added n-BuLi (1.6 M in hexane, 9.5 mL, 15 mmol) dropwise at −78° C. under a nitrogen atmosphere with stirring. The resulting solution was stirred at −78° C. for 3 hrs, quenched by a 50 mL of saturated aqueous NH₄Cl solution and extracted with DCM (3×70 mL). The organic phase was dried (Na₂SO₄), filtered and concentrated to give a residue, which was purified by column chromatography over silica gel (20:1, petroleum ether/EtOAc) to give e as a yellow solid (530 mg, 36%).

Step 6

Scheme 42:

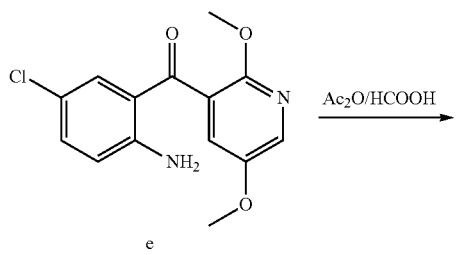

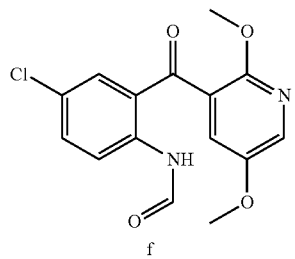

To a solution of e (530 mg, 1.8 mmol) in 5 mL of THF at room temperature was added 6 mL of acetic formic anhydride solution, which was prepared by stirring a mixture of acetic anhydride (4 mL) and formic acid (2 mL) (Note that ratio of acetic anhydride volume and formic acid volume is 2:1) at 50° C. for 2 h and cooled to room temperature. The resulting solution was stirred at room temperature for 2 hrs, diluted with 50 mL of H₂O and filtered to afford a yellow solid, which was washed with hexane and dried in vacuo to afford f (530 mg, 95%), which was used directly for the next step.

Step 7

Scheme 43:

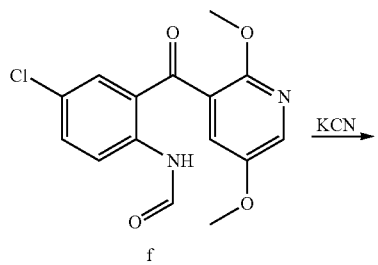

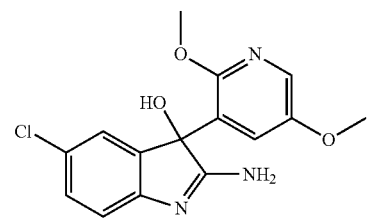

Compound 201

To a mixture of f (530 mg, 1.65 mmol), and KHCO₃ (404 mg, 4 mmol) in MeOH—H₂O (v/v=1/1, 15 mL) was added KCN (263 mg, 4 mmol) one portion with stirring. The resulting solution was heated at 80° C. for 30 min, cooled to room temperature, diluted by 100 mL of water and extracted with DCM (3×70 mL). The organic phase was dried (Na₂SO₄), filtered and concentrated to give a residue, which was purified by column chromatography over silica gel (30:1, DCM/methanol) to afford Compound 201 (130 mg, 25%) as a white solid.

Example 17

Representative Synthesis of Racemic Compound 142

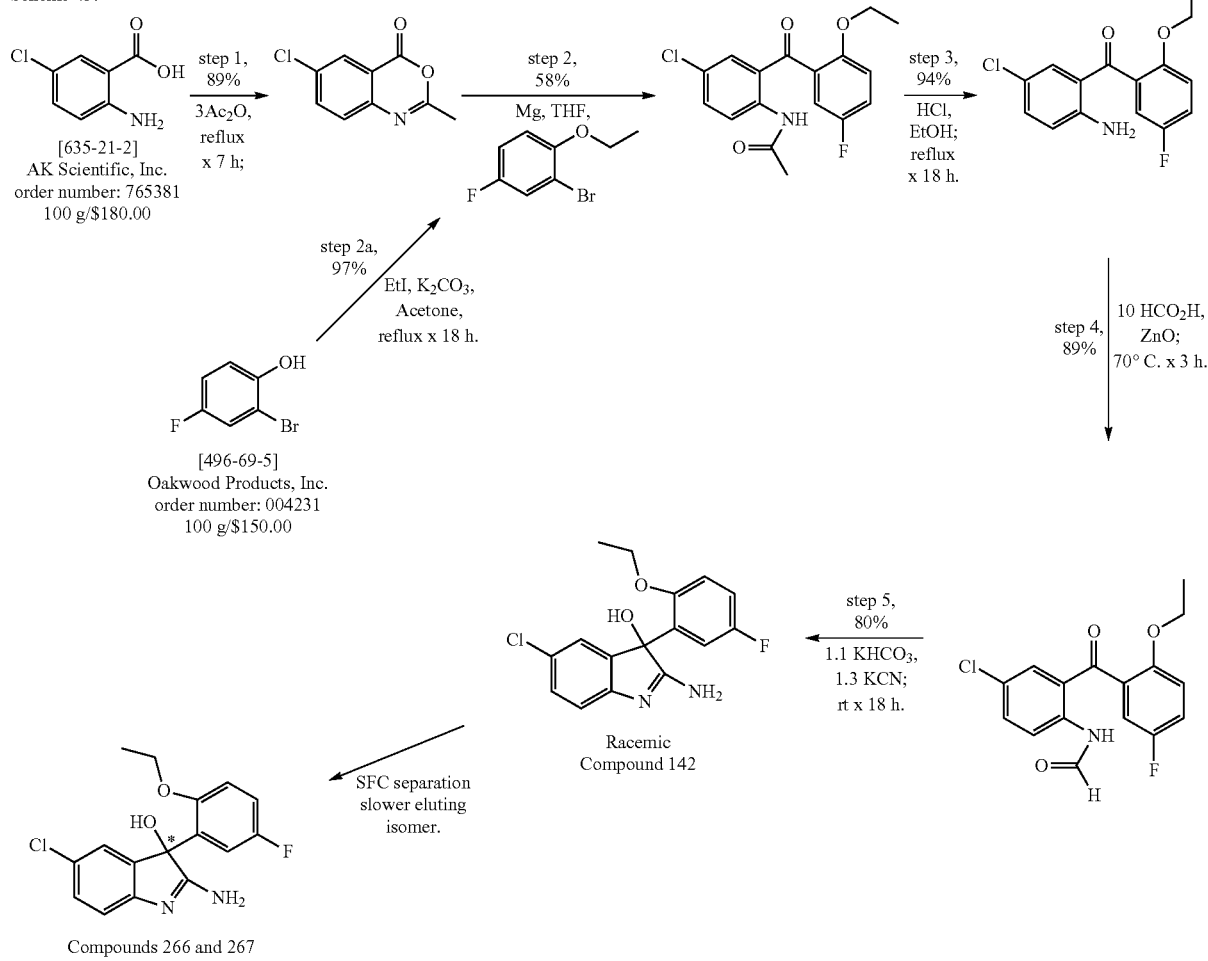

Scheme 43:

Experimental

Starting materials, reagents and solvents were obtained from commercial suppliers and used without further purification. NMR spectra were obtained using a Bruker 400 instrument. $^1$H spectra were measured with reference to an internal standard of tetramethylsilane at 0 ppm. HPLC analysis was performed using Agilent 1100 with Zorbax 3.5µ Extend-C18 column (4.6×50 mm). Mobile phase consisting of solvent A, 0.1% trifluoroacetic acid in water, solvent B, 0.1% trifluoroacetic acid in MeCN. Gradient was from 10-90% mobile phase B in 4 minutes. λ=210, 254 nm.

2-Amino-5-chlorobenzoic acid [635-21-2] was ordered from AK Scientific, Inc, order number: 765381.

2-Bromo-4-fluorophenol [496-69-5] was ordered from Oakwood Products, Inc, order number: 004231.

Step 1. Making 6-chloro-2-methyl-4H-benzo[d][1,3]oxazin-4-one

A mixture of 2-Amino-5-chlorobenzoic acid (90 g, 524 mmole) and acetic anhydride (160 ml) was heated to reflux under nitrogen for 3 hours. The reaction became a solution during heating. The reaction was cooled to room temperature. Some solid came out during this period of time. The reaction mixture was slurried with 1 L IPA and filtered. The solid was washed with more IPA (50 ml) and dried under vacuum at room temperature for 18 hours. Product was collected as solid (91 g, yield: 89%). $^1$H NMR (CDCl$_3$): 8.14 (d, J=6 Hz, 1H), 7.73 (dd, J=21 Hz, 6 Hz, 1H), 7.50 (d, J=21 Hz, 1H), 2.47 (s, 3H).

Step 2a. Making 2-ethoxy-4-fluorophenyl bromide

2-Bromo-4-fluorophenol (105 g, 550 mmole), Ethyl iodide (110 ml, 1.37. mole) and potassium carbonate (190 g) were stirred vigorously in acetone (400 ml) at 55° C. under nitrogen for 4 hours. The reaction was cooled to room temperature and filtered. The solid was washed with more acetone (50 ml). The filtrate was concentrated on a rotary evaporator to remove most acetone (some solid came out). MTBE (600 ml) was added. The mixture was stirred for 3 minutes and filtered. The filtrate was concentrated to a clear oil (117 g, yield: 97%). $^1$H NMR (CDCl$_3$): 7.28 (m, 1H), 6.96 (m, 1H), 6.83 (m, 1H), 4.05 (qt, J=18 Hz, 2H), 1.45 (t, J=18 Hz, 3H).

Step 2. Making N-(4-chloro-2-(2-ethoxy-5-fluorobenzoyl)phenyl)acetamide

Making Grignard reagent: A solution of 2-ethoxy-4-fluorophenyl bromide (30 g, 138 mmol) in THF (140 ml) was added dropwisely into a stirred mixture of magnesium flake and catalytically amount of iodine under nitrogen. The result mixture was heated to reflux for 15 minutes and cooled to room temperature (Grignard reagent). In a separated flask, 6-chloro-2-methyl-4H-benzo[d][1,3]oxazin-4-one (25 g, 128 mmole) was dissolved into THF (200 ml) and stirred under nitrogen. The Grignard reagent was transferred slowly into the flask during 30 minutes. The reaction temperature was kept below 55° C. during addition. The result mixture was stirred for further 2 hours under nitrogen. The reaction was quenched by slowly addition of aqueous solution of ammonium chloride (30 g/300 ml). The reaction was extracted into MTBE (500 ml). The organic layer was washed with brine, dried ($Na_2SO_4$), filtered and concentrated on a rotary evaporator to solid. The solid was sonicated for 5 minutes in ethyl acetate (250 ml) and filtered. The filtrate was concentrated on a rotary evaporator to about 70 ml and cooled at −20° C. for 4 hours. During this time, crystallized product came out and was collected by filtration (25 g, yield: 58%). $^1$H NMR ($CDCl_3$): 11.2 (br, 1H), 8.73 (d, J=22 Hz, 1H), 7.49 (dd, J=24 Hz, 7 Hz, 1H), 7.38 (d, J=6 Hz, 1H), 7.2 (m, 1H), 7.07 (dd, J=20 Hz, 8 Hz, 1H), 6.93 (m, 1H), 3.97 (q, J=17 Hz, 2H), 2.27 (s, 1H), 1.13 (tr, J=17 Hz, 3H).

Step 3. Making (2-amino-5-chlorophenyl)(2-ethoxy-5-fluorophenyl)methanone

N-(4-chloro-2-(2-ethoxy-5-fluorobenzoyl)phenyl)acetamide (25 g) was refluxed in a solution of concentrated HCl (6.5 ml) and ethanol (200 ml) for 3 hours. The result mixture was basified by adding aqueous sodium carbonate and extracted into MTBE (500 ml). The MTBE layer was washed by brine and dried ($Na_2SO_4$), filtered and concentrated to an oil (20 5 g, yield: 94%). $^1$H NMR ($CDCl_3$): 7.20 (m, 2H), 7.11 (m, 1H), 7.00 (dd, J=20 Hz, 8 Hz, 1H), 6.91 (dd, J=23 Hz, 10 Hz, 1H), 6.65 (m, 1H), 6.34 (br, 1H), 3.39 (q, J=18 Hz, 2H), 1.19 (tr, J=18 Hz, 3H).

Step 4. Making N-(4-chloro-2-(2-ethoxy-5-fluorobenzoyl)phenyl)formamide

A mixture of (2-amino-5-chlorophenyl)(2-ethoxy-5-fluorophenyl)methanone (20.5 g, 70 mmole), zinc oxide (3 g, 37 mmole) and formic acid (28.5 ml, 740 mmole) was heated under nitrogen at 55° C. for 4 hours with vigorous stirring. The result mixture was cooled to room temperature. DCM (250 ml) was added. The reaction was filtered. The filtrate was washed by water (200 ml×2), sat. $NaHCO_3$ (200 ml), brine (100 ml), dried ($Na_2SO_4$), filtered and concentrated to an yellow solid (20 g, yield: 89%). $^1$H NMR ($CDCl_3$): 11.10 (br, 1H), 8.73 (b, J=22 Hz, 1H), 8.53 (s, 1H), 7.51 (dd, J=22 Hz, 6 Hz, 1H), 7.41 (d, J=6 Hz, 1H), 7.20 (m, 1H), 7.10 (dd, J=19 Hz, 7 Hz, 1H), 6.93 (dd, J=22 Hz, 10 Hz, 1H), 3.96 (q, J=18 Hz, 2H), 1.13 (tr, J=18 Hz, 3H). $^1$H NMR and HPLC of N-(4-chloro-2-(2-ethoxy-5-fluorobenzoyl)phenyl)formamide.

Step 5. Making Compound 142, 2-amino-5-chloro-3-(2-ethoxy-5-fluorophenyl)-3H-indol-3-ol N-(4-chloro-2-(2-ethoxy-5-fluorobenzoyl)phenyl)formamide (20 g, 62.5 mmole) was dissolved in hot methanol (300 ml). Water (200 ml) was added (precipitated). The mixture was stirred for 2 minutes. Potassium carbonate (6.8 g, 69 mmole) was added to the stirred mixture and stirred for 2 minutes. Potassium cyanide (4.6 g, 81 mmole) was added into the stirred reaction. The mixture was stirred at room temperature for 18 hours and stirred at 70° C. (bath) for 4 hours. The reaction was cooled to room temperature and poured into water (400 ml), stirred and filtered. The solid was dried in a vacuum oven at room temperature. The solid was slurried in hot chloroform (200 ml, bath temperature: 55° C.) for 10 minutes and filtered. The solid was collected and dried (16 g, yield: 80%). $^1$H NMR ($CDCl_3$): 7.72 (dd, J=24 Hz, 8 Hz, 1H), 7.13 (dd, J=20 Hz, 6 Hz, 1H), 7.00 (m, 1H), 6.91 (d, J=20 Hz, 1H), 6.80 (dd, J=22 Hz, 10 Hz, 1H), 6.76 (d, J=5 Hz, 1H), 4.85 (br, 3H), 3.78 (m, 1H), 3.58 (m, 1H), 3.31 (q, J=17 Hz, 2H), 0.97 (tr, J=17 Hz, 3H).
$^1$H NMR and HPLC of Compound 142, 2-amino-5-chloro-3-(2-ethoxy-5-fluorophenyl)-3H-indol-3-ol Example 18

Chiral Separation of Racemic Compound 142 Using Supercritical Fluid Chromatography (SFC)

This example describes a procedure for resolving racemic Compound 142 to its enantiomers, Compounds 266 and 267, by super critical fluid chromatography (SFC). The racemic synthesis was carried out as described in Example 17 by WuXi PharmaTech. The amorphous material isolated from the SFC was crystallized to give a crystalline material that was fully characterized.
1. Separation Method:
SFC and HPLC were used for the analytical and SFC was used for preparative chiral separation.
1.1 Analytical Separation Method:
SFC-MS
Instrument: Berger Analix analytical SFC with DAD Detector
Column: ChiralPak AD-3, 150×4.6 mm ID
Mobile phase: A for SFC $CO_2$ and B for 2-Propanol (0.05% DEA)
Gradient: B 25%
Flow rate: 2.4 ml/min
Wavelength: 220 nm
HPLC
Instrument: Shimadzu LC-20A with DAD Detector
Column: Shim-pack XR-ODS 30 mm*3 mm I.D.
Mobile phase: A for $H_2O$ (0.1% TFA) and B for Acetonitrile
Gradient: B 10-80%
Flow rate: 1.2 ml/min
Wavelength: 210 nm and 254 nm
1.2 Preparative Separation Method
Instrument: Berger MGIII preparative SFC
Column: ChiralPak AD-H, 250×30 mmI.D.
Mobile phase: A for SFC $CO_2$ and B for 2-Propanol
Gradient: A:B 70:30
Flow rate: 80 ml/min
Sample preparation: dissolved in Ethanol, 50 mg/ml
Injection: 4 ml per injection.
After separation, the fractions were dried off via rotary evaporator at bath temperature 40° C.
2. Crystallization:
To the separated Enantiomer A and B was added Ethyl ether at amount of 50 ml/g respectively. Stir at 30° C. bath to make sure the solid was dissolved. The solution was transferred into wild-mouth bottles. Place the bottles in the ventilated hood to let Ethyl ether evaporate at controlled speed. With the solvent evaporated slowly, crystals can be seen separate out from the mother liquid. Filtrate and wash the solid with Ethyl ether for three times to give Enantiomer A and B (crystal) respectively. The mother liquid was concentrated via rotary evaporator to get Enantiomer A and B (mother liquid) respectively.

Enantiomer A and B (crystal) was grinded and dried respectively in vacuum oven at 30° C. for 24 h to remove residue Ethyl ether.
3. Quality control:
3.1e.e Test Via SFC-MS
The test was carried out under the same conditions as shown in 1.1
3.2 Purity Test Via HPLC and NMR
The test was carried out under the same conditions as shown in 1.1
3.3 Analysis of X-RPD and DSC
4. Note:
During the whole process, only Ethanol, 2-Propanol and Ethyl ether were used.

TABLE 2

Results of chiral separation of Compound 142

| Description | Weight(g) | e.e(%) | Purity (%) |
|---|---|---|---|
| Enantiomer A, faster eluting isomer by SFC on AD-H column(crystal) | 29.6 | 99.3 | 99.16(210 nm) 98.77(254 nm) |
| Enantiomer A, faster eluting isomer by SFC on AD-H column(mother liquid) | 14.6 | 97.9 | 96.12(210 nm) 90.78(254 nm) |
| Enantiomer B, slower eluting isomer by SFC on AD-H column(crystal) | 24.5 | 98.9 | 100.0(210 nm) 100.0(254 nm) |
| Enantiomer B, slower eluting isomer by SFC on AD-H column(mother liquid) | 20.5 | 95.5 | 96.44(210 nm) 97.86(254 nm) |

Example 19

Selected Aminoindole Compounds of the Invention Demonstrate in Vitro Potency Against Different *Plasmodium* Species In Vitro Potency Against *P. falciparum*:

In vitro potency against *P. falciparum* was assessed using a modified version of the method of Plouffe and coworkers (Plouffe, D., A. Brinker, C. McNamara, K. Henson, N. Kato, K. Kuhen, A. Nagle, F. Adrian, J. T. Matzen, P. Anderson, T. G. Nam, N. S. Gray, A. Chatterjee, J. Janes, S. F. Yan, R. Trager, J. S. Caldwell, P. G. Schultz, Y. Zhou, and E. A. Winzeler. 2008. In silico activity profiling reveals the mechanism of action of antimalarials discovered in a high-throughput screen. Proc Natl Acad Sci USA 105:9059-64). Parasites were cultured in the presence of drug in RPMI (Sigma) containing 4.16 mg/ml Albumax in a total volume of 500 at a 2.5% hematocrit and an initial parasitemia of 0.3% in black Greiner GNF clear-bottom plates. Cultures were incubated 72 hr at 37° C. under 95% $N_2$, 4% $CO_2$ and 3% $O_2$. At the end of the incubation, SYBR green was added to a dilution of 1:10, 000 and plates were stored overnight (or until ready to be read) at −80° C. Just before reading, plates were centrifuged at 700 rpm and fluorescence was read using 480 nm excitation and 530 nm emission frequencies. Compound concentrations that inhibit parasite replication reduce the fluorescence intensity of SYBR green bound to parasite DNA.

Results show that many aminoindoles have potent $IC_{50}$ values (inhibitory concentration which reduces parasitemia by 50%) in the low double-digit nanomolar range with respect to *P. falciparum* strains 3D7, Dd2 and HB3 (not shown). $IC_{50}$ values were determined by staining the parasites with nucleic acid stain DAPI and/or SYBR green. $IC_{50}$ value ranges with respect to *P. falciparum* strain 3D7 for several compounds of the invention are indicated in Table 1 using asterisks (see Table 1 legend).

In Vitro Potency Against *P. knowlesi*:

Selected compounds were tested against *P. knowlesi* H1 strain parasites cultured in *Rhesus* blood cells as a surrogate for *P. vivax* infections using the method of Kocken and coworkers (Kocken, C. H., H. Ozwara, A. van der Wel, A. L. Beetsma, J. M. Mwenda, and A. W. Thomas. 2002. *Plasmodium knowlesi* provides a rapid in vitro and in vivo transfection system that enables double-crossover gene knockout studies. Infect Immun 70:655-660). Briefly, *P. knowlesi* were cultured in 2% *Rhesus* macaque erythrocytes (New England Primate Research Center) in RPMI culture media containing 10% Human O+ serum (Interstate Blood Bank). Schizont stage parasites were purified by floatation in 60% Percoll (GE life sciences) and allowed to reinvade to generate a synchronous population of ring stage parasites. Drug assays were performed by plating ring stage parasites at 0.5% parasitemia in triplicate, in RPMI containing 2.5 μg/ml hypoxanthine. Parasites were incubated for 24 hours with serially diluted test compounds. After 24 hours, thin smears were made to confirm that reinvasion had occurred, 0.5 μCi $^3$H-labeled hypoxanthine (Perkin Elmer) were added to each well, and parasites were allowed to progress through S-phase to early schizonts. Cells were then harvested via glass filter plates and $^3$H incorporation was measured by scintillation counting. Values were normalized to percentage of controls containing no drug, and $IC_{50}$ values were generated (GraphPad Prism®). Results are shown in Table 3.

TABLE 3

In vitro Potency and Selectivity

| | Potency ($IC_{50}$; nM) *Plasmodium* spp. | | | | Selectivity | | | hERG |
|---|---|---|---|---|---|---|---|---|
| | | | | | Mammalian cytotoxicity ($IC_{50}$; μM) | | | |
| Compound No. | Pf Dd2 | Pf 3D7 | Pk H1 | Pb ANKA | Dermal Fibroblast | Kidney epithelial | Eryth. Lysis | (μM) CHO |
| 1 | 285 | 200 | 336 | 1560 | >242 | >242 | >155 | >25 |
| 2 | 1,460 | 665 | ND | 1363 | >242 | >242 | >155 | ND |
| 3 | 675 | 313 | ND | 1689 | >242 | >242 | >155 | ND |
| 11 | 37 | 30 | ND | ND | 24 | 24 | >129 | ND |
| 37 | 455 | 183 | 318 | ND | >62.5 | >62.5 | >168 | ND |
| 38 | 110 | 38 | ND | ND | >62.5 | >62.5 | >147 | ND |
| 39 | 347 | 108 | 190 | 2987 | >62.5 | >62.5 | >178 | ND |

TABLE 3-continued

In vitro Potency and Selectivity

| Compound No. | Potency ($IC_{50}$; nM) Plasmodium spp. | | | | Selectivity | | | hERG ($\mu M$) CHO |
|---|---|---|---|---|---|---|---|---|
| | | | | | Mammalian cytotoxicity ($IC_{50}$; $\mu M$) | | | |
| | Pf Dd2 | Pf 3D7 | Pk H1 | Pb ANKA | Dermal Fibroblast | Kidney epithelial | Eryth. Lysis | |
| 146 | 37 | 22 | 90 | ND | >188 | >188 | >120 | 19 |
| 202 | 81 | 21 | ND | ND | >195 | >195 | >125 | ND |
| 142 | 49 | 23 | 38 | ND | >195 | >195 | >125 | 21 |
| 266 | 58 | 18 | ND | 342 | >195 | >195 | >125 | ND |
| 267 | 65 | 28 | 26 | 331 | >195 | >195 | >125 | 36.6 |

Table 3 legend:
Pf Dd2: *Plasmodium falciparum* strain Dd2;
PF 3D7: *P. falciparum* strain 3D7;
Pk H1: *P. knowlesi* strain H1;
Pb ANKA: *P. berghei* ANKA strain;
Dermal fibroblast: Normal Human Dermal Fibroblasts (Clonetics #CC-2509);
Kidney epithelial: normal human renal proximal tubule cells (Clonetics #CC-2553);
Eryth. Lysis: erythrocyte lysis;
CHO: Chinese hamster ovary cells.

Example 20

Selected Aminoindole Compounds of the Invention Demonstrate in Vivo Efficacy Against *P. berghei* and *P. falciparum* in Mice In Vivo Efficacy Against *P. berghei* in Mice:

Species of *Plasmodium* that infect humans (such as *P. falciparum, P. vivax, P. knowlesi*) do not infect or cause disease in rodents and can only be evaluated directly in primate models of infection. Because of ethical issues and costs, the acute *P. berghei* model in rodents is considered the "gold standard" for assessing anti-malarial efficacy in animal models. This model is adapted from Peters' "4-day suppressive test" (Peters, W. 1987. Chemotherapy and Drug Resistance in Malaria, p. 102-115, 2ed, vol. 1. Academic Press, Orlando, Fla.; Peters, W. 1975. The chemotherapy of rodent malaria, XXII. The value of drug-resistant strains of *P. berghei* in screening for blood schizontocidal activity. Ann Trop Med Parasitol 69:155-171). All studies were conducted in accordance with the Guide for the Care and Use of Laboratory Animals (National-Research-Council. 1996. Guide for the Care and Use of Laboratory Animals. National Academy Press, Washington, D.C.) and the PHS guidelines. Animals were maintained according to NIH guidelines and were allowed to acclimatize for 1 week prior to the commencement of studies. On Day 0, groups of 4-6-week old female Swiss Albino mice (n=5) were infected by tail vein injection with 0.2 ml heparinized blood diluted to contain $1 \times 10^7$ N-clone parasites. The aminoindole analogs were formulated in 1.6% lactic acid mixed sodium salt, 1% Tween 80, 9% ethanol and 20% Cerestar (hydroxypropyl β-cyclodextrin; Wacker Chimie) and were administered by oral gavage. On Day 0, a single dose was given at 6 hr post initial infection, and over the subsequent 3 days the dose was split and administered b.i.d., with 6 hours between doses. Animals in the Control-group received vehicle alone. Dose concentration and frequency of dosing were based upon preliminary tolerability/exposure studies. On Day 4 post-infection ($5^{th}$ day of assay) blood was collected by tail-nick, and thin smear microscope slides were prepared and stained using Diff Quick®. Parasitized erythrocytes were counted and compared with the total number of erythrocytes per microscopic field to determine the percent parasitemia. A minimum of 350 erythrocytes were counted. Animals showing no detectable parasites on Day 4 were examined every 2-3 days to determine whether cure was sterile. Animals with no detectable parasites 28 days after cessation of dosing (Study Day 33) were considered cured.

Results (Table 4) show that selected aminoindoles are highly active against *P. berghei*, suppressing parasitemia on Study Day 5 by 81-100%. Compound 3, Compound 37, Compound 142 and Compound 267 all were able to affect cures at doses of 100-200 mg/kg/day.

TABLE 4

Efficacy of Aminoindoles against *P. berghei*

| Compound | Dose (mg/kg/day) b.i.d. p.o. | % Suppression Day 5 | Average Day of Recrudescence (no. animals/total) | No. Cured |
|---|---|---|---|---|
| 1 | 50 | 100% | D13 (5/5) | 0/5 |
| 2 | 50 | 80% | NA | 0/5 |
| 3 | 50 | 100% | D12 (3/5) | 2/5 |
| | 100 | 100% | NA | 5/5 |
| 37 | 100 | 100% | D17 (2/5) | 3/5 |
| | 200 | 100% | NA | 5/5 |
| 39 | 50 | 98% | D10 (3/5) | 0/5 |
| | 100 | 99% | D13 (3/5) | 0/5 |
| 146 | 100 | 99% | D6 (1/5) | 0/5) |
| 202 | 100 | 95% | NA | 0/5 |
| | 200 | 98% | D17 (2/5) | 0/5 |
| 142 | 100 | 99% | D11 (1/5) | 0/5 |
| | 200 | 99% | D13 (1/5) | 3/5 |
| 266 | 100 | 81% | NA | 0/5 |
| 267 | 100 | 95% | D14 (2/4) | 0/5 |
| | 200 | 100% | D12 (2/5) | 3/5 |

Table 4 legend:
Dose (mg/kg/day) b.i.d. p.o.: total daily dose in milligrams/kilogram administered orally in 2 split doses/day;
% Suppression Day 5: percent reduction in parasitemia compared with mean of untreated controls on Study Day 5, approximately 17 hr after the final dose. Values of 100% Suppression indicate that no parasites were detected upon microscopic examination; animals may still contain parasites below the limit of detection.
Average Day of Recrudescence: animals having no detectable parasites on Day 5 had blood smears examined every 2-3 days thereafter until parasites were again observed; the average of the Study Day on which parasites were again detected is recorded, preceded by the letter "D". The total number of animals with no detectable parasites on Day 5, but which subsequently regressed is given as a proportion of the total number of animals in the dosing group (in parentheses).
NA: not applicable. Either all animals were parasitemic on Day 5 or else all animals were cured.
No. cured: number of animals cured, as a proportion of all the animals in the dosing group, defined as animals with no detectable parasites at any time through at least 30 days after cessation of dosing.

In Vivo Efficacy Against *P. falciparum* in Mice:

Because rodent malaria species (such as *P. berghei*) are not necessarily identical to human species (such as *P. falciparum*) with respect to sensitivity to antimalarial compounds, a "humanized mouse" model has been developed that supports the erythrocytic cycle of *P. falciparum*. Compound 267 was tested for efficacy against *P. falciparum* Pf3D7$^{0087/N9}$ growing in NOD-scid IL-2Rγ$^{null}$ mice engrafted with human erythrocytes (Angulo-Barturen, I., et al. 2008. PLoS ONE 3:e2252). Briefly, groups of 3 animals were infected on Day 0 with $2 \times 10^7$ *P. falciparum* parasites and were treated orally once per day for 4 days with 5, 25 and 100 mg/kg/day formulated as described above beginning on Day 3 post infection. In parallel, groups of 3 animals were infected on Day 0 with $1 \times 10^7$ parasites on Day 0 and received the same doses beginning 1 hr after infection. Parasitemia was assessed by FACS as previously described (Jiménez-Díaz, M.-B., et al. 2009. Cytometry Part A 75:225-235. In the same humanized murine system, efficacy was also tested against *P. berghei*, with animals infected on Day 0 (Jimenez-Diaz, M. B., et al. 2005. Cytometry A 67:27-36). Results are shown in Table 5.

TABLE 5

Efficacy of Compound 267 in Different Rodent Models

| Compound No. | *P. berghei* N-clone | | *P. berghei* ANKA strain GFP MRA-865 | | *P. falciparum* Pf3D7$^{0087/N9}$ | |
|---|---|---|---|---|---|---|
| | ED$_{50}$ | ED$_{90}$ | ED$_{50}$ | ED$_{90}$ | ED$_{50}$ | ED$_{90}$ |
| 267 b.i.d. | 32 | 68 | 19 | 30 | 40 | 74 |
| 267 t.i.d. | 35 | 58 | ND | ND | ND | ND |

Table 5 legend:
Parasite species and strains are listed at the top.
ED$_{50}$: Effective
Dose at which 50% of parasitemia is suppressed. Values were calculated by non-linear regression analysis using GraphPad Prism and units are in mg/kg/day.
b.i.d: animals were dosed twice per day;
t.i.d.: animals were dosed three times/day.
Compound 267 was slightly more active against *P. berghei* than against *P. falciparum*, but efficacy was very similar against both parasite species.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method of treating a subject with malaria, comprising administering to the subject in need thereof an effective amount of a compound of Formula I:

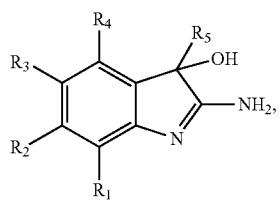

(I)

or a pharmaceutically acceptable salt thereof, wherein $R_1$, $R_2$, $R_3$ and $R_4$ are independently hydrogen, halogen, ($C_1$-$C_4$)alkyl, or ($C_1$-$C_4$)alkoxy;

$R_5$ is aryl, heteroaryl, cycloalkyl, heterocyclyl, aryl($C_1$-$C_3$)alkyl, aryl($C_3$-$C_{10}$)heterocyclyl, aryl($C_1$-$C_3$)alkoxy, heteroaryl($C_1$-$C_3$)alkyl, cycloalkyl($C_1$-$C_3$)alkyl, heterocyclyl($C_1$-$C_3$)alkyl, alkylheteroaryl, ($C_1$-$C_6$)alkyl, or ($C_1$-$C_4$)alkoxy, each optionally substituted with one to three groups represented by $R_6$;

each $R_6$ is independently halogen, nitro, cyano, hydroxy, ($C_1$-$C_4$)alkyl, halo($C_1$-$C_3$)alkyl, hydroxy($C_1$-$C_4$)alkyl, ($C_1$-$C_4$)alkoxy, halo($C_1$-$C_4$)alkoxy, aryl, haloaryl, cycloalkyl, aryl($C_1$-$C_3$)alkyl, aryl($C_1$-$C_4$)alkoxy, heterocyclyl, —N(R$_7$)$_2$, —C(=NOH)NH$_2$, —NR$_7$CON (R$_7$)$_2$, —CON(R$_7$)$_2$, —CO$_2$R$_7$, —COR$_8$, —OC(O)R$_8$, —SO$_2$N(R$_8$)$_2$, —SO$_2$R$_8$, —SR$_8$, —S(C$_1$-C$_3$)alkylcycloalkyl, —NR$_7$COR$_8$, —NR$_7$CO$_2$R$_8$, —NR$_8$SO$_2$R$_8$, —S(=O)R$_8$, —O-cycloalkyl, —O-heterocyclyl, adamantyl, —OC(=O)N(R$_7$)$_2$,

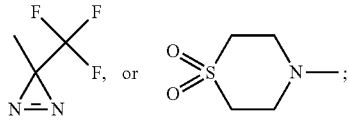

each $R_7$ is independently hydrogen, ($C_1$-$C_{10}$)alkyl, aryl, or aryl($C_1$-$C_3$)alkyl, each optionally substituted with halogen, ($C_1$-$C_3$)alkoxy, ($C_1$-$C_3$)alkyl, halo($C_1$-$C_3$)alkyl, halo($C_1$-$C_3$)alkoxy, cyano or nitro; and each $R_8$ is independently hydrogen, halogen, ($C_1$-$C_{10}$) alkyl, ($C_1$-$C_{10}$)alkoxy, aryl, aryl($C_1$-$C_3$)alkyl, cycloalkyl or aryl($C_1$-$C_3$)alkoxy, each optionally substituted with halogen, ($C_1$-$C_3$)alkoxy, ($C_1$-$C_3$)alkyl, halo ($C_1$-$C_3$)alkyl, halo($C_1$-$C_3$)alkoxy, cyano or nitro.

2. The method of claim 1, wherein $R_3$ is chlorine.

3. A method of treating a subject with malaria, comprising administering to the subject in need thereof an effective amount of a compound of Formula II:

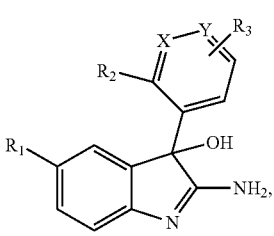

(II)

or a pharmaceutically acceptable salt thereof, wherein $R_1$ is chlorine, $R_2$ is ethoxy, $R_3$ is fluorine, X is carbon and Y is carbon.

4. A method of treating a subject with malaria, comprising administering to the subject in need thereof an effective amount of a compound of Formula II:

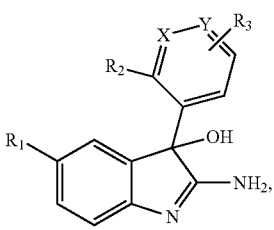

(II)

or a pharmaceutically acceptable salt thereof, wherein $R_1$ is chlorine, $R_2$ and $R_3$ are methoxy, X is nitrogen and Y is carbon.

5. A method of treating a subject with malaria, comprising administering to the subject in need thereof an effective amount of a compound of Formula II:

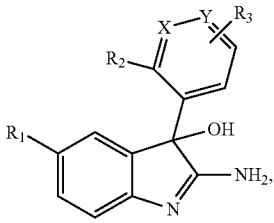

(II)

or a pharmaceutically acceptable salt thereof, wherein $R_1$ is chlorine, $R_2$ is hydroxy, $R_3$ is fluorine, X is carbon and Y is carbon.

6. A method of treating a subject with malaria, comprising administering to the subject in need thereof an effective amount of a compound of Formula IIa:

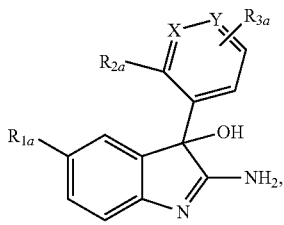

(IIa)

or a pharmaceutically acceptable salt thereof, wherein:

X is carbon or nitrogen;

Y is carbon or nitrogen;

$R_{1a}$ is hydrogen, halogen, nitro, cyano, hydroxy, $(C_1-C_6)$ alkyl, $(C_1-C_6)$alkenyl, $(C_1-C_6)$alkynyl, $(C_1-C_6)$alkoxy, aryl, heteroaryl, cycloalkyl, heterocyclyl, aryl$(C_1-C_3)$ alkyl, heteroaryl$(C_1-C_3)$alkyl, cycloalkyl$(C_1-C_3)$alkyl, heterocyclyl$(C_1-C_3)$alkyl, hydroxy$(C_1-C_3)$alkyl, $N(R_{5a})_2$, $C(=NOH)NH_2$, $NR_{5a}CON(R_{5a})_2$, $CON(R_{5a})_2$, $CO_2R_{5a}$, $COR_{6a}$, $OC(O)R_{5a}$, $SO_2N(R_{5a})_2$, $SO_2R_{6a}$, $NR_{5a}COR_{6a}$, $NR_{5a}CO_2R_{6a}$, $NR_{5a}SO_2R_{6a}$ or $OC(=O)N(R_{5a})_2$, each optionally substituted with one or more groups represented by $R_{4a}$;

$R_{2a}$ is $(C_1-C_6)$alkyl, $(C_1-C_6)$alkoxy, $S(C_1-C_6)$alkyl, $SO(C_1-C_6)$alkyl or $SO_2(C_1-C_6)$alkyl, each optionally substituted with one or more groups represented by $R_{4a}$;

$R_{3a}$ is halogen, $(C_1-C_6)$alkyl or $(C_1-C_6)$alkoxy, each optionally substituted with one or more groups represented by $R_{4a}$;

each $R_{4a}$ is independently selected from halogen, nitro, cyano, hydroxy, $(C_1-C_4)$alkyl, halo$(C_1-C_3)$alkyl, hydroxy$(C_1-C_4)$alkyl, $(C_1-C_4)$alkoxy, halo$(C_1-C_4)$ alkoxy, aryl, haloaryl, cycloalkyl, aryl$(C_1-C_3)$alkyl, aryl $(C_1-C_4)$alkoxy, heterocyclyl, $N(R_{5a})_2$, $C(=NOH)NH_2$, $NR_{5a}CON(R_{5a})_2$, $CON(R_{5a})_2$, $CO_2R_{5a}$, $COR_{6a}$, $OC(O)$ $R_{5a}$, $SO_2N(R_{5a})_2$, $SO_2R_{6a}$, $SR_{6a}$, $S(C_1-C_3)$alkylcycloalkyl, $NR_{5a}COR_{6a}$, $NR_{5a}CO_2R_{6a}$, $NR_{5a}SO_2R_{6a}$, $S(=O)R_{6a}$, —O-cycloalkyl, —O-heterocyclyl, adamantyl, $OC(=O)N(R_{5a})_2$,

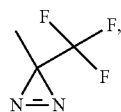

or

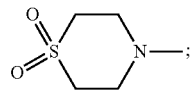

;

each $R_{5a}$ is independently selected from hydrogen, $(C_1-C_{10})$alkyl, aryl or aryl$(C_1-C_6)$alkyl, each optionally substituted with halogen, $(C_1-C_3)$alkoxy, $(C_1-C_3)$alkyl, halo $(C_1-C_3)$alkyl, halo$(C_1-C_3)$alkoxy, cyano or nitro; and each $R_{6a}$ is independently selected from hydrogen, halogen, $(C_1-C_{10})$alkyl, $(C_1-C_{10})$alkoxy, aryl$(C_1-C_3)$alkyl, cycloalkyl or aryl$(C_1-C_3)$alkoxy, each optionally substituted with halogen, $(C_1-C_3)$alkoxy, $(C_1-C_3)$alkyl, halo $(C_1-C_3)$alkyl, halo$(C_1-C_3)$alkoxy, cyano or nitro.

7. The method of claim 6, wherein $R_{1a}$ is halogen, $(C_1-C_4)$ alkyl or $(C_1-C_4)$alkoxy.

8. The method of claim 6, wherein $R_{2a}$ is $(C_1-C_6)$alkoxy.

9. The method of claim 6, wherein $R_{3a}$ is halogen.

10. The method of claim 6, wherein the compound has the structure of Formula IIIa:

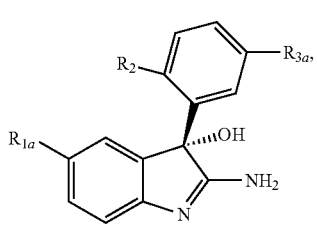

(IIIa)

or a pharmaceutically acceptable salt thereof.

11. The method of claim 6, wherein the compound has the structure of Formula XXIIIa:

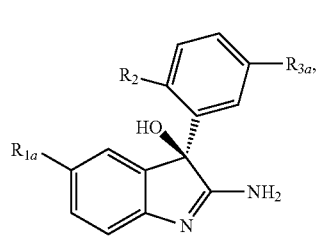

(XXIIIa)

or a pharmaceutically acceptable salt thereof.

12. A method of treating a subject with malaria, comprising administering to the subject in need thereof an effective amount of a compound represented by the following structural formula:

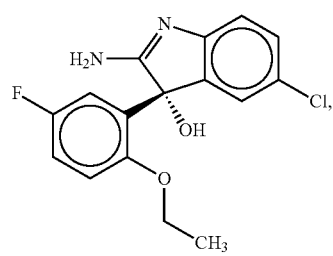

or a pharmaceutically acceptable salt thereof.

* * * * *

UNITED STATES PATENT AND TRADEMARK OFFICE
CERTIFICATE OF CORRECTION

PATENT NO. : 8,980,926 B2  
APPLICATION NO. : 13/504635  
DATED : March 17, 2015  
INVENTOR(S) : Ralph Mazitschek et al.

It is certified that error appears in the above-identified patent and that said Letters Patent is hereby corrected as shown below:

Title Page

On Page 1, Item (75), Inventor Urgaonkar, delete "Arlington, NC" and insert --Arlington, MA--

In the Claims

In Column 154, Claim 10, line 22, delete "Formula Ma" and insert --Formula IIIa--

Signed and Sealed this  
Fourteenth Day of July, 2015

Michelle K. Lee  
*Director of the United States Patent and Trademark Office*

UNITED STATES PATENT AND TRADEMARK OFFICE
CERTIFICATE OF CORRECTION

PATENT NO.        : 8,980,926 B2
APPLICATION NO.   : 13/504635
DATED             : March 17, 2015
INVENTOR(S)       : Ralph Mazitschek et al.

It is certified that error appears in the above-identified patent and that said Letters Patent is hereby corrected as shown below:

On the title page, item 56

On the page 2, in column 1, under "Other Publications", line 13, delete "Chemcial" and insert -- Chemical --, therefor.

On the page 2, in column 2, under "Other Publications", line 2, delete "(Arythydrazo)-," and insert -- (Arylhydrazo)-, --, therefor.

On the page 2, in column 2, under "Other Publications", line 3, delete "thianaphtenes"," and insert -- thianaphthenes", --, therefor.

On the page 2, in column 2, under "Other Publications", line 6, delete "Antimalaria" and insert -- Antimalarial --, therefor.

On the page 2, in column 2, under "Other Publications", line 17, delete "Indo1" and insert -- Indol --, therefor.

On the page 2, in column 2, under "Other Publications", line 20, delete "$5HT_1Receptor$" and insert -- $5HT_1$ Receptor --, therefor.

On the page 2, in column 2, under "Other Publications", line 21, delete "Radiopharmaceuticlas," and insert -- Radiopharmaceuticals, --, therefor.

In the specification

In column 10, line 19, delete "(C1-C6)" and insert -- $(C_1-C_6)$ --, therefor.

In column 10, line 20, delete "(C1-C6)" and insert -- $(C_1-C_6)$ --, therefor.

Signed and Sealed this
First Day of March, 2016

Michelle K. Lee
*Director of the United States Patent and Trademark Office*

CERTIFICATE OF CORRECTION (continued)
U.S. Pat. No. 8,980,926 B2

In the specification

In column 97, line 33, delete "glyceptate," and insert -- gluceptate, --, therefor.

In column 97, line 40, delete "teoclate," and insert -- theoclate, --, therefor.

In column 97, line 43, after "D-glucamine," insert -- D-Lysine, --.

In column 104, line 26, delete "$R_{1b}$" and insert -- $R_{4b}$ --, therefor.

In column 107, line 22, delete "(C1-C6)" and insert -- ($C_1$-$C_6$) --, therefor.

In column 108, line 6, delete "Spiro" and insert -- spiro --, therefor.

In column 108, line 48, delete "phthalzinyl," and insert -- phthalazinyl, --, therefor.

In column 116, line 63, delete "AR—H)," and insert -- Ar—H), --, therefor.

In column 118, line 19, delete "511.487" and insert -- 511.5478 --, therefor.

In column 122, line 18, delete "that that" and insert -- that --, therefor.

In column 131, line 14, delete "20 g," and insert -- 20 g --, therefor.

In column 134, line 18, delete "-75.deg" and insert -- -75° C. --, therefor.

In column 137, line 55, delete "gave" and insert -- give --, therefor.

In column 141, line 11, delete "$K_2CO_3$(2.3 g," and insert -- $K_2CO_3$ (2.3 g, --, therefor.

In column 143, line 11, delete "isomer." and insert -- isomer --, therefor.

In column 148, line 3, delete "500" and insert -- 50 μl --, therefor.

In column 149, line 57, delete "Chimie)" and insert -- Chemie) --, therefor.

In column 150, line 48, delete "0/5)" and insert -- 0/5 --, therefor.